(12) United States Patent
Am Ende et al.

(10) Patent No.: US 6,517,866 B1
(45) Date of Patent: Feb. 11, 2003

(54) SERTRALINE SALTS AND SUSTAINED-RELEASE DOSAGE FORMS OF SERTRALINE

(75) Inventors: Mary Tanya Am Ende, Griswold, CT (US); William John Curatolo, Niantic, CT (US); Hylar Lewis Friedman, Brattleboro, VT (US); Dwayne Thomas Friesen, Bend, OR (US); Scott Max Herbig, East Lyme, CT (US); Ravi Mysore Shankar, Groton, CT (US); James Blair West, Bend, OR (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/380,897

(22) PCT Filed: Jun. 15, 1998

(86) PCT No.: PCT/IB98/00934

§ 371 (c)(1),
(2), (4) Date: Sep. 7, 1999

(87) PCT Pub. No.: WO99/01121

PCT Pub. Date: Jan. 14, 1999

Related U.S. Application Data

(60) Provisional application No. 60/051,498, filed on Jul. 1, 1997, provisional application No. 60/051,420, filed on Jul. 1, 1997, provisional application No. 60/051,414, filed on Jul. 1, 1997, and provisional application No. 60/051,402, filed on Jul. 1, 1997.

(51) Int. Cl.[7] .............................. A61K 9/22; A61K 9/26; A61K 9/44; A61K 9/52; A61K 9/54

(52) U.S. Cl. ....................... 424/457; 424/458; 424/468; 424/469; 424/473; 424/474; 424/484; 424/490; 424/463

(58) Field of Search ............................... 424/451, 464, 424/456, 465, 468, 469, 472, 474, 475, 489, 463, 457, 484, 490, 473, 458

(56) References Cited

U.S. PATENT DOCUMENTS

| | | | |
|---|---|---|---|
| 4,536,518 A | 8/1985 | Welch, Jr. et al. | 514/647 |
| 4,777,288 A | 10/1988 | Quallich et al. | 562/491 |
| 4,792,448 A | 12/1988 | Ranade | 424/438 |
| 4,797,286 A | 1/1989 | Thakkar et al. | 424/456 |
| 4,803,076 A | 2/1989 | Ranade | 424/438 |
| 4,839,104 A | 6/1989 | Quallich et al. | 260/396 |
| 4,847,092 A | 7/1989 | Thakkar et al. | 424/456 |
| 4,855,500 A | 8/1989 | Spavins | 564/270 |
| 4,876,282 A | 10/1989 | Robertson et al. | 514/554 |
| 4,887,617 A | 12/1989 | Ruppert et al. | 131/70 |
| 4,940,731 A | 7/1990 | Bick | 514/657 |
| 4,962,128 A | 10/1990 | Doogan et al. | 514/647 |
| 4,971,998 A | 11/1990 | Wurtman et al. | 514/654 |
| 5,026,707 A | 6/1991 | Nixon et al. | 514/255 |

(List continued on next page.)

FOREIGN PATENT DOCUMENTS

| | | | |
|---|---|---|---|
| EP | 0080341 | 6/1983 | A61K/9/22 |
| EP | 0259113 | 3/1988 | A61K/9/22 |
| EP | 0259113 | 9/1988 | A61K/9/22 |

(List continued on next page.)

OTHER PUBLICATIONS

Remington's Pharmaceutical Sciences, 16th, Mack Publishers, Pennyslvania, 1980, pps. 1585–1594.

(List continued on next page.)

Primary Examiner—James M. Spear
(74) Attorney, Agent, or Firm—Peter C. Richardson; Gregg C. Benson; Carmella A. O'Gorman

(57) ABSTRACT

Sustained release dosage forms of sertraline which release sertraline at a rate between 1 mgA/hr and 40 mgA/hr. The dosage forms may exhibit an initial delay period during which sertraline is released at a rate less than 1 mgA/hr.

116 Claims, 6 Drawing Sheets

U.S. PATENT DOCUMENTS

| | | | |
|---|---|---|---|
| 5,061,728 A | 10/1991 | Koe | 514/520 |
| 5,104,899 A | 4/1992 | Young et al. | 514/646 |
| 5,112,619 A | 5/1992 | Thakkar et al. | 424/456 |
| 5,130,338 A | 7/1992 | Bacopoulos | 514/646 |
| 5,135,947 A | 8/1992 | Robrtson et al. | 514/466 |
| 5,196,607 A | 3/1993 | Quallich | 568/327 |
| 5,248,699 A | 9/1993 | Sysko et al. | 514/647 |
| 5,371,092 A | 12/1994 | Johnson | 514/321 |
| 5,597,826 A | 1/1997 | Howard et al. | 514/255 |
| 5,637,624 A | 6/1997 | Schaus et al. | 514/657 |
| 5,741,807 A | 4/1998 | Thomas | 514/400 |
| 5,945,416 A | 8/1999 | Shannon et al. | 514/220 |

FOREIGN PATENT DOCUMENTS

| | | | |
|---|---|---|---|
| EP | 0357369 | 3/1990 | A61K/9/22 |
| EP | 0415612 | 3/1991 | A61K/31/135 |
| EP | 0415613 | 3/1991 | A61K/31/135 |
| EP | 0429189 | 5/1991 | A61K/31/135 |
| EP | 0357369 | 5/1993 | A61K/9/22 |
| EP | 0712837 | 5/1996 | C07C/225/20 |
| EP | 0768083 | 4/1997 | A61K/31/135 |
| WO | WO9014077 | 11/1990 | A61K/9/52 |
| WO | WO9200103 | 1/1992 | A61K/45/06 |
| WO | WO9202212 | 2/1992 | A61K/9/32 |
| WO | WO9202215 | 2/1992 | A61K/31/135 |
| WO | WO9218005 | 10/1992 | A01N/43/62 |
| WO | WO9318755 | 9/1993 | A61K/9/16 |
| WO | WO9324154 | 12/1993 | A61L/15/62 |
| WO | WO9427589 | 12/1994 | A61K/31/135 |
| WO | WO9500154 | 1/1995 | A61K/33/00 |
| WO | WO9609047 | 3/1996 | A61K/31/485 |
| WO | WO9703670 | 2/1997 | A61K/31/445 |
| WO | WO9737640 | 10/1997 | A61K/9/22 |
| WO | WO0232918 | 4/2002 | C07H/17/08 |

OTHER PUBLICATIONS

The Merck Index, 12$^{th}$ Merck & Co., NJ, 1996, pp. 1455.
Drug Facts and Comparison, 1997, pp. 1564 and 1574.
Merck Index 12th Merck & Co. NJ 1996, p. 1455.
Rem. Pharm. Sciences, 16th Mack Publisher, Pennsylvania, 1980, pp. 1576, 1585.

SERTRALINE SALTS AND SUSTAINED-RELEASE DOSAGE FORMS OF SERTRALINE

This is a National Stage filing under 35 USC §371 based on PCT/IB98100934, which was filed internationally on Jun. 15, 1998 and which claims priority from U.S. provisional applications 60/051,498 filed Jul. 1, 1997; 60/051,420 filed Jul. 1, 1997; 60/051,414 filed Jul. 1, 1997; and 60/051,402 filed Jul. 1, 1997.

FIELD OF THE INVENTION

This invention relates to certain salts of sertraline, and to a sustained-release dosage form of sertraline having an improved side effect profile, and to a method of treating a psychiatric or other illness comprising administering sertraline in such a sustained-release dosage form to a mammal, including a human patient, in need of such treatment

BACKGROUND OF THE INVENTION

Sertraline is a selective serotonin reuptake inhibitor (SSRI), which is useful, inter alia, as an antidepressant and anorectic agent, and in the treatment of obsessive-compulsive disorder, premenstrual dysphoric disorder, post-traumatic stress disorder, chemical dependencies, anxiety-related disorders, panic and premature ejaculation. See U.S. Pat. No. 4,536,518, Published International Application WO 92/18005, U.S. Pat. No. 5,130,338, U.S. Pat. No. 4,971,998, Published International Application WO 92/00103, U.S. Pat. No. 5,061,728, U.S. Pat. No. 4,940,731, and U.S. Pat. No. 4,962,128, each of which is incorporated herein by reference. Sertraline is also known as (1S-cis)-(4-(-3,4-dichlorophenyl)-1,2,3,4-tetrahydro-N-methyl-naphthalenamine, has the empirical formula $C_{12}H_{17}NCl_2$, and has the structural formula

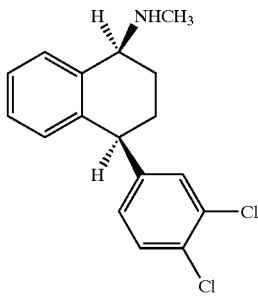

Sertraline is most commonly prescribed for therapy of depressive illness, in the general dose range 50–200 mg/day. Sertraline has an elimination half-life of 23 hr, and is dosed once daily.

Patients are generally initiated on sertraline at a dose of 50 mg/day. Patients who do not respond at the 50 mg dose are given higher doses. Initiation at doses greater than 50 mg is generally avoided, when possible, because side effects such as dizziness, tremor, and sweating, and gastrointestinal upset are generally believed to be more severe at higher doses. If necessary to achieve efficacy, higher doses may be reached by slow titration up from lower doses. Improved sertraline dosage forms which exhibited a lower incidence and/or severity of side effects would be advantageous because (1) patient comfort would be improved, and (2) dosing could be initiated at doses higher than 50 mg. without the need for dose titration. Initiation at higher starting doses would, in turn, be useful by potentially effecting a shorter onset of antidepressive action. Thus, such an improved sertraline dosage form which permitted oral dosing of high doses of sertraline (e.g., 200 mg and higher) with relatively reduced side effects would permit wider therapeutic application of sertraline therapy, and would accordingly provide a significant improvement in dosing compliance and convenience. Likewise, an improved dosage form which lowered the incidence and/or severity of side-effects at lower doses would also be of significant value.

SUMMARY OF THE INVENTION

This invention provides an oral, sustained release dosage form of sertraline which decreases, relative to currently marketed instant release sertraline tablet dosage forms which deliver an equivalent bolus dose, the incidence and/or severity of gastrointestinal and/or other side effects such as dizziness, tremor and sweating. The dosage form operates by effecting the release of sertraline at a rate sufficiently slow to ameliorate side effects.

Dosage forms which release more than 70% of their contained sertraline within one hour or less are not "sustained release", and form no part of this invention. This feature thus excludes from the invention immediate release dosage forms containing 40 mg of sertraline or less. Such dosage forms will technically release sertraline at a rate less than 40 mgA/hr, but are excluded because they do not do so in a sustained manner.

In one aspect this invention provides a sustained-release dosage form suitable for administration to a mammal, comprising sertraline, or a pharmaceutically salt thereof, and a pharmaceutically acceptable carrier, which dosage form releases sertraline into a use environment at a rate not exceeding 0.8 mgA/hr/kg, preferably at a rate not exceeding 0.7 mgA/hr/kg, provided said dosage form (1) releases not more than 70% of the sertraline contained therein within the first hour following entry into said use environment and (2) releases sertraline at a rate of at least 0.02 mgA/hr/kg. This aspect of the invention describes a dosage form without regard to the size of any particular mammal.

In another aspect this invention provides a sustained-release dosage form suitable for oral administration to a mammal, comprising sertraline, or a pharmaceutically acceptable salt thereof, and a pharmaceutically acceptable carrier, which dosage form releases sertraline into a use environment at a rate not exceeding 40 mgA/hr, provided said dosage form (1) releases not more than 70% of the sertraline contained therein within the first hour following entry into said use environment and (2) releases sertraline at a rate of at least 1 mgA/hr. This aspect of the invention describes a dosage form suitable for administration to mammals such as average size adult humans. A dosage form according to the invention thus releases sertraline at a rate of from 1 to 40 mgA/hr. Particular release rate ranges include rates of from 2 to 40 mgA/hr, 3 to 40 mgA/hr, 1 to 30 mgA/hr, 2 to 30 mgA/hr, and 3 to 30 mgA/hr. The ranges 1 to 30 mgA/hr and 2 to 30 mgA/hr are preferred. The ranges 1 to 25 mgA/hr and 2 to 25 mgA/hr are more preferred.

Reference to a dosage form which "releases" sertraline means (1) release of sertraline to a mammal's gastrointestinal (GI) tract following ingestion or (2) release of sertraline into an in vitro test medium for analysis by an in vitro test as described below. Reference to a "use environment" can thus be either to in vivo gastrointestinal fluids or to in vitro test medium.

Rates of sertraline release lower than 25, 30 or 40 mgA/hr are also within the scope of the invention and may produce even better side effect profiles, particularly for patients under 50 kg weight for example children. Thus a sertraline release rate of 7 mgA/hr after ingestion represents a release profile within the scope of the invention and may be even more efficacious for ameliorating side effects. The rate must, of course, be high enough to provide therapeutic efficacy, that is, a therapeutically sufficient amount of sertraline should be delivered from the dosage form before the dosage form is excreted with the feces. Accordingly, dosage forms according to the invention should release sertraline at a rate of at least 1 mgA/hr.

The unit "kg" as used herein in "mgA/hr/kg" refers to kilograms of body weight for the mammal being treated.

It is noted that the mouth-to-anus transit time of a non-disintegrating (e.g., tablet or multiparticulate) dosage form is approximately 24 hours. Dosage forms of this invention release at least 6%, preferably at least 70%, of their contained sertraline within 24 hour. Absorption of sertraline from the lower gastrointestinal (GI) tract, especially from the colon, is less efficient than absorption from the upper GI tract, i.e., from the small intestine, as shown in Example 3. It is accordingly therapeutically advantageous to deliver less sertraline in the lower GI tract and more sertraline in the upper GI tract. Accordingly, controlled release sertraline dosage forms according to the invention release at least 60%, preferably at least 70%, of their contained sertraline within 24 hours, preferably within 18 hours, most preferably within 16 hours.

Although dosage forms as defined above generally release at least 70% of their contained sertraline within 24 hours, a dosage form according to the invention can release substantially all of its sertraline well before 24 hours so long as it otherwise releases sertraline at a rate not exceeding 40 mgA/hr or 0.8 mgA/hr.

The term "ingestion" as used herein is essentially synonymous with "swallowing".

The invention is particularly useful for administering relatively large amounts of sertraline to a patient. The amount of sertraline contained within the dosage form is preferably at least 10 mgA, and can be as high as 500 mgA or more. The amount contained in the dosage form is more preferably 25 mgA to 400 mgA. The dosage form can be unitary or divided e.g., constituted by two or more units (such as capsules or tablets which, taken together, constitute the dosage form) which are taken at or about the same time.

Sertraline can be employed in the dosage forms of this invention in the form of its pharmaceutically acceptable salts, and also in anhydrous as well as hydrated forms. All such forms can be used within the scope of this invention. The sertraline employed is preferably the free base, hydrochloride, aspartate, acetate, or lactate salts. For convenience and consistency, reference to "sertraline" in terms of therapeutic amounts or in release rates in the claims is to active sertraline, abbreviated herein as "mgA", i.e., the non-salt, nor-hydrated free base having a molecular weight of 306.2. Amounts in mgA can conveniently be converted to equivalent weights for whatever salt form is desired.

The dosage forms which constitute the subject matter of the invention are, as mentioned, sustained release formulations. The dosage form can be in the form of a tablet, a capsule, a multiparticulate form, a multiparticulate form in a tablet or capsule, or a unit dose packet (sometimes referred to in the art as a "sachet"). Also included are combination dosage forms, for example those comprising one or more sustained release tablets contained within a capsule shell such as a gelatin capsule shell.

The term "tablet" is intended to embrace compressed tablets, coated tablets, matrix tablets, osmotic tablets, and other forms known in the art, and as more fully disclosed and described below, The term "capsule" is intended to embrace capsules in which the body of the capsule disintegrates after ingestion to release particulate contents which exhibit the desired sustained-release behavior, and also capsules for which the body of the capsule remains substantially intact during its residence in the GI tract.

In a further aspect this invention provides a method for treating a psychiatric or other illness, comprising administering to a mammal in need of such treatment, including a human patient, a therapeutically effective amount of sertraline in a sustained-release oral dosage form which releases the sertraline according to the release rate described above. Such illnesses include those known in the art as being treatable with sertraline, including those mentioned above.

In a further aspect, this invention provides a sustained release dosage form suitable for administration to a mammal, comprising sertraline or a pharmaceutically acceptable salt thereof and a pharmaceutically acceptable carrier, which dosage form releases sertraline in vitro at a rate less than 40 mgA/hr, when dissolution tested in a USP-2 apparatus containing a test medium comprising 900 ml of acetate buffer, pH 4.0, which is 0.075 M in NaCl, at 37° C., as follows:

(1) if said dosage form is a sustained release tablet or a non-disintegrating sustained release capsule, said USP-2 apparatus is equipped with a paddle stirring at 50 rpm; or (2) if said dosage form is a multiparticulate, said USP-2 apparatus is equipped with a paddle stirring at 100 rpm; provided said dosage form (a) releases not more than 70% of the sertraline contained therein within the first hour following initiation of testing and (b) releases sertraline at a rate of at least 1 mgA/hr.

Examples of dosage forms which fall into category (1) above include:

a. sustained release reservoir tablets such as coated diffusive tablets, osmotic tablets, and membrane coated swelling hydrogel tablets;

b. matrix tablets, both disintegrating and non-disintegrating; and c. non-disintegrating capsules; The capsule shell material should be a non-gelatin polymer such as ethylcellulose or cellulose acetate.

Examples of dosage forms which fall into category (2) above include unit dose packets (also known in the art as "sachets") and powders for oral suspension. Ideally, each particle in a multiparticulate constitutes a self-contained unit of sustained release. The particles can be formed into larger units as by being compressed into a larger tablet-like unit which is more convenient for swallowing. The larger units disintegrate rapidly upon swallowing to give rise to the multiparticulate form, however.

It is noted that the term "multiparticulate" means a plurality of particles wherein each particle is designed to yield controlled release of sertraline. Ideally, each particle in a multiparticulate constitutes a self-contained unit of sustained release. The particles can be formed into larger units. The multiparticulate particles each comprise sertraline and one or more excipients as needed for fabrication and performance. The size of individual particles is generally between about 50 $\mu$m and about 3 mm. A multiparticulate predominantly composed of particles toward the low end of this size range is sometimes referred to herein as a powder. Multiparticulates predominantly composed of particles toward the high end of the size range are sometimes referred to herein as beads. Beads having a size outside this range may also be useful.

Any of the dosage forms in (1) or (2) above can be incorporated into a gelatin capsule. If the dosage form is in a gelatin capsule or otherwise gelatin coated, then the dosage form is tested in a USP-2 paddle apparatus as described in (1) or (2), as appropriate depending on the exact dosage form, but with trypsin added to the acetate buffer to a concentration of 0.1 mg/mL. Generally, the amount of or size of the dosage form tested should contain or be equivalent to 200 mgA of sertraline or less. If the dosage form contains more than 200 mgA, then the amount of acetate buffer test medium should be increased proportionately.

The test solution employed above is an acetic acid/acetate buffer solution, pH 4.0, which buffer is 0.075 M in NaCl, and which is intended to simulate gastrointestinal fluids. The test solution is made by making a 0.13M solution of acetic acid in water and then making this solution into an acetic acid/acetate buffer by adding potassium hydroxide, typically as an 0.5M aqueous solution, until a pH of 4.0 has been attained. Sufficient sodium chloride is then added to make the solution 0.075M in NaCl. The temperature of the test solution is maintained at 37 C throughout the dissolution test.

The in vitro release rate is determined by multiplying the incorporated dose by 0.8, and dividing this number by the measured time at which 80% of the incorporated dose has been released and dissolved, as further discussed below. If 80% of the incorporated sertraline is not released in 24 hr, then the mgA sertraline released at 24 hr should be divided by 24 hr, to give the release rate. Further, no more than 40 mgA is released in any one hour. This aspect of the invention thus defines a sustained release dosage form by means of a conveniently performed in vitro test conducted in a standard, well known apparatus. As previously mentioned, not more than 40 mgA should be released in any one hour of the test. It is noted that a USP-2 apparatus, equipped with a paddle, is well known and described in United States Pharmacopoeia XXIII (USP) Dissolution Test Chapter 711, Apparatus 2.

A unitary dosage form is dissolution tested by placing it in a paddle-equipped USP-2 apparatus containing 900 ml of be test solution just described, the test solution having a temperature of 37 deg C, with the paddle stirring at 50 rpm. If the dosage form is a capsule, it is tested in the same manner except that the test solution is augmented to contain 0.1 mg/mL of trypsin. Filtered aliquots (typically 2 or 10 mL) of the dissolution medium are taken at various times, referred to herein as "pull points." The exact time at which an aliquot is removed is not particularly critical, although pull points may be standardized for convenience. The aliquot is filtered and assayed for sertraline content utilizing an HPLC assay or other suitable assay. The data is plotted as mgA sertraline (active sertraline) released (or % sertraline base released) on the y-axis vs time on the x-axis. The time at which 80% of the sertraline dose is released is noted.

To assure accuracy of results, more than one, for example three, or more preferably six, separate dissolution tests should be conducted and the rates determined and averaged.

As mentioned above, an in vitro release rate is calculated from the dissolution test by dividing the quantity of sertraline corresponding to 80% release (determined by multiplying the incorporated dose by 0.8) by the time it takes to effect the 80% release. For example, if a 100 mgA sertraline oral dosage form is tested in this fashion, and 80% of the incorporated sertraline is released in 8 hr, then the release rate is (100 mgA×0.8)/18 hr, or 10 mgA/hr. This dosage form is thus within the scope of this invention. As another example, if a 50 mgA sertraline oral dosage form is tested in vitro, and 80% of the incorporated sertraline (as sertraline base) is released in 0.4 hr, then the release rate is (50 mgA×0.8)/0.4 hr, or 100 mgA/hr, and the dosage form is not within the scope of the invention.

While there are many methods of describing the in vitro-rate of drug release from a dosage form (e.g. first-order rate constant zero-order rate constant, initial rate, etc.), the method described above provides a clear test which is independent of the mechanism of sertraline release from the dosage form.

It is noted that immediate release sertraline dosage forms are known and commercially available (ZOLOFT®, registered trademark of Pfizer Inc.) as 50 mgA and 100 mgA strength tablets. When 50 mgA ZOLOFT tablets were evaluated using the in vitro dissolution test described above, an average of 80% of the contained sertraline was released (i.e., dissolved in the test fluid) at 0.7 hr after the start of the dissolution test. Thus the immediate release 50 mgA tablet released sertraline at a rate of 57 mgA/hr, calculated by the method described above. When two 100 mgA ZOLOFT tablets (total dose 200 mgA) were evaluated by the above dissolution test, 80% of the contained sertraline was released at 1.2 hr after starting the test. Thus each 100 mg tablet released sertraline a rate of 67 mg/hr and release for the 200 mg dose was 134 mg/hr, calculated by the method described above. Thus as the above in vitro test illustrates, such dosage forms are outside the scope of this invention.

In a further aspect, this invention provides a sustained release dosage form of sertraline suitable for oral administration to a mammal, which results in a maximum sertraline plasma concentration, $C_{max}$, which is less than 80% of the $C_{max}$ determined when an equal dose of sertraline is orally administered in the form of an immediate release bolus (such as an immediate-release tablet). This aspect of the invention defines a sustained release dosage form according to the invention by means of an appropriate in vivo test which is conducted in the mammalian species of interest. For example, to test whether a sustained release oral sertraline dosage form ameliorates side effects in humans, the sertraline test dosage form is dosed to half of a group of 12 or more humans and, after an appropriate washout period (e.g. 1 week) the same subjects are dosed with an immediate-release bolus dose at the same strength. The other half of the group is dosed with the immediate-release bolus dose first, followed by the sertraline (sustained-release) test dosage form and the plasma sertraline levels are measured as a function of time. After determining $C_{max}$ for each individual on each treatment, an average $C_{max}$ is determined. If $C_{max}$ for the sustained release sertraline test dosage form is less than 80% of the $C_{max}$ for the bolus dose, then the test dosage form will provide a side effect improvement over the bolus dosage form and is within the scope of the invention. In this embodiment, the dosage form may be sustained release, engineered with or without an initial delay period, as disclosed below. It is noted that "immediate release" means the bolus has not been engineered to include a means for slowing disintegration or dissolution of the dosage form.

Dosage forms which pass either an in vitro test relating thereto as described herein, or an in vivo test relating thereto as described herein (including the $C_{max}$ test just described, are within the scope of the invention, as are dosage forms which pass all such tests relating thereto.

As stated above, sustained release sertraline dosage forms provide a decreased $C_{max}$ relative to the $C_{max}$ for immediate-release dosage forms containing equal amounts of sertraline. That is, sustained-release dosage forms exhibit a $C_{max}$ which is less than or equal to 80% of the $C_{max}$ provided by an equivalent immediate release dose. Preferred dosage forms additionally provide a total blood drug exposure which again, relative to equivalent immediate-release dosage forms, is not proportionately decreased as much as the sustained release $C_{max}$. A "total blood drug exposure" is determined as AUC, the area under the curve determined by plotting the concentration of drug in the plasma (Y-axis) vs. time (X-axis). AUC is generally an average value, and would for example be averaged over all the subjects in the crossover study described above. The determination of AUCs is a well known procedure, and is described, for example, in "Pharmacokinetics; Processes and Mathematics," by Peter Welling (ACS Monograph 185, Amer. Chem. Soc., Wash. D.C.: 1986). By way of example, suppose a sustained release 100 mgA sertraline dosage form A exhibits a $C_{max}$ that is 65% of the $C_{max}$ produced by a 100 mgA immediate release sertraline bolus. In a preferred embodiment, sustained release dosage form A will also exhibit an AUC that is higher than 65% of that provided by the bolus.

In a further aspect the invention provides a sertraline sustained release dosage form which exhibits an initial delay in sertraline release when the dosage form enters its environment of use, i.e. after ingestion, followed by sustained sertraline release as described above. During the delay period essentially no sertraline is released, although "essentially no sertraline" includes very small release rates less than 1 mgA/hr. This type of dosage form is sometimes referred to herein as a "delayed plus sustained releases" dosage form. The inventors have demonstrated that certain side effects of sertraline, namely nausea, regurgitation, and diarrhea, are partially or primarily mediated by direct contact of sertraline with the upper gastrointestinal tract, primarily the stomach, rather than mediated systemically, that is via exposure of sertraline to the bloodstream after absorption. Prior to the human clinical studies carried out by the inventors (presented as Example 6 below), the locally mediated nature of these three sertraline side effects was not known. Thus advantageous sertraline dosage forms of this invention include dosage forms which exhibit a spatial or temporal delay in sertraline release after ingestion. Sustained release sertraline dosage forms which exhibit a spatial delay include those which are sensitive to their position along the GI tract, which are independent of time, and which possess a mechanism that largely or completely prevents release of sertraline in the stomach, and which then commence sustained release after the dosage form has passed into the duodenum. Once having commenced sustained release of sertraline, the sustained release is restricted in rate and extent as closed above for "non-delayed" sustained release sertraline dosage forms. Spatially-delayed sustained release dosage forms of this invention commence sustained release of sertraline within approximately 30 minutes, preferably within approximately 15 minutes, of passing out of the stomach into the duodenum.

Temporally-delayed sustained release sertraline dosage forms according to the invention are those which, after ingestion, exhibit a temporal delay before commencing sustained sertraline release. By a temporal delay in this context is meant a delay following ingestion which is not related to the spatial location of the dosage form in the GI tract. Temporally-delayed sustained release sertraline dosage forms exhibit a delay of up to 3 hours after ingestion, preferably up to 2 hours, most preferably up to 1.5 hours. This temporal delay minimizes the exposure of the upper gastrointestinal tract, particularly the stomach, to sertraline after oral ingestion, thus ameliorating locally mediated side effects. After the delay, the dosage form releases sertraline in a manner restricted in rate and extent as disclosed above for "non-delayed" sustained release sertraline dosage forms.

It is noted that in the claims, reference to a "sustained release dosage form" is to a dosage form not having an initial delay period implemented therein. Reference in the claims to dosage forms having a period of delay implemented therein are specific in pointing this out, for example as to a "sustained release dosage form having an initial delay period", to a temporally or spatially "delayed plus sustained release dosage form", or similar language such as "said dosage form having an initial delay period."

It is noted that there is a natural lag period, usually not more than 15 minutes following ingestion, during which time the dosage form is wetted, hydrated, and otherwise affected by bodily (GI) fluids so that it can start to dissolve and release sertraline. This typical lag or induction period of about ten minutes during which wetting occurs is subsumed under the delay period engineered into the dosage form, such that the delay period can also be thought of as about 15 minutes up to 3 hours, preferably about 15 minutes up to 2 hours. If the induction or lag time is not more than 15 minutes, it is not considered to be delayed plus sustained release. Rather, it is simply sustained release.

Thus this invention provides a temporally delayed plus sustained release dosage form suitable for administration to a mammal, comprising sertraline or a pharmaceutically acceptable salt thereof and a pharmaceutically acceptable carrier, which dosage form, following ingestion by said mammal, releases sertraline into said mammal's GI tract at a rate less than 1 mgA/hr for an initial delay period of up to three hours, preferably of up to two hours, more preferably of up to 1.5 hr, and which thereafter releases sertraline at a rate of from 1 mgA/hr to 40 mgA/hr, provided said dosage form releases not more than 70% of the sertraline contained therein within the first hour after said delay period.

The dosage form can also be a spatially delayed plus sustained release dosage form suitable for oral administration to a mammal, comprising sertraline or a pharmaceutically acceptable salt thereof and a pharmaceutically acceptable carrier, which dosage form, following ingestion by said mammal, releases sertraline into said mammal's stomach at a rate less than 1 mgA/hr, and which, after having passed into said mammals duodenum; releases sertraline at a rate-of from 1 mgA/hr to 40 mgA/hr, provided said dosage form releases not more man 70% of the sertraline contained therein within the first hour after passing into said mammal's duodenum.

The following in vitro tests can be used to determine whether or not a particular dosage form falls within the scope of the invention, depending on whether the onset of the sustained release component is temporally or spatially delayed.

If the dosage form is temporally delayed, the in vitro test can be conducted exactly as previously described for sustained release dosage forms which do not have a temporal delay incorporated therein. The dosage form will release sertraline at a rate less than 1 mgA/hr for a period of up to three hours, or less, corresponding to the length of the delay period, followed by sustained sertraline release at a rate of from 1 mgA/hr to 40 mgA/hr thereafter. Conditions, test apparatus, and test medium can otherwise be the same as for pure sertraline sustained release dosage forms. As with other dosage forms, dosage forms with a temporal delay release not more than 70% of the remaining sertraline contained therein within the first hour following said delay.

If the dosage form is spatially delayed with a pH-trigger, the invention provides a sustained release pH-triggered dosage form suitable for oral administration to a mammal, said dosage form having an initial delay period prior to the onset of sustained release, comprising sertraline or a pharmaceutically acceptable salt thereof and a pharmaceutically acceptable carrier, which dosage form, when tested in vitro in a USP-2 apparatus, releases sertraline into 0.1 N HCl at a rate less than1 mgA/hr for at least 1 hour and, thereafter, releases sertraline into phosphate buffer, pH 6.8 containing 1% polysorbate 80 at a rate of from 1 mgA/hr to 40 mgA/hr, provided the dosage form releases not more than 70% of the remaining sertraline contained therein within the first hour following said delay.

If the dosage form is spatially-delayed with an enzyme-trigger, the invention provides an oral sustained release enzyme-triggered dosage form-suitable for administration to a mammal, said dosage form having an initial delay period prior to the onset of sustained release, comprising sertraline or a pharmaceutically acceptable salt thereof and a pharmaceutically acceptable carrier, which dosage form, when tested in vitro in a USP apparatus releases sertraline into 0.1 N HCl at a rate less than 1 mgA/hr for a period of at least 1 hour and, thereafter, releases sertraline at a rate of from 1 mgA/hr to 40 mgA/hr into phosphate buffer, pH 6.8, containing 1% polysorbate 80 and in the presence of an enzyme suitable for triggering the onset of said sustained release, provided the dosage form releases not more than 70% of the remaining sertraline contained therein within the fist hour following said delay.

In these in vitro tests, 1 mgA/hr is calculated as the average hourly quantity of sertraline released, calculated over the initial 1 hr or longer time period of the test corresponding to the delay period.

It is an object of this invention to decrease the incidence and severity of sertraline-induced side effects. This s particularly important at high doses, for example 100 mg and up, at which the incidence of side effects can be higher. This object is effected, inter alia, by controlling the rate and degree of exposure of the gastrointestinal tract and the systemic circulation to sertraline, in at least a portion of sertraline-dosed patients, thereby reducing the overall incidence and severity of sertraline-induced side effects.

It is noted that sustained-release dosage forms of various types are known and employed conventionally in the art to provide reduced dosing frequency for short half-life compounds and to reduce fluctuations in plasma concentrations, sometimes imparting an improved safety/efficacy profile due to avoidance of multiple plasma drug concentration peaks and troughs throughout the day. Because elimination of sertraline from the human body is characterized by a long half-life of about 23 hours, however, it is surprising that a sustained-release dosage form would offer any benefit.

The present invention further provides a new and useful acetate salt of sertraline, hereinafter referred to as "sertraline acetate," pharmaceutical compositions containing sertraline acetate; methods of using sertraline acetate and processes for preparing sertraline acetate.

The present invention further provides a new and useful L-lactate salt of sertraline, hereinafter referred to as "sertraline L-lactate," pharmaceutical compositions containing seine L-lactate, methods of using sertraline L-lactate and processes-for preparing sertraline L-lactate.

The present invention further provides a new and useful L-aspartate salt of sertraline, hereinafter referred to as "sertraline L-aspartate," pharmaceutical compositions containing sertraline L-aspartate, methods of using sertraline L-aspartate and processes for preparing sertraline L-aspartate.

The instant acetate salt of sertraline is highly water soluble and as such is particularly well-suited for use in a controlled release, for example, sustained release, encapsulated solution or delayed release, dosage form of sertraline. Further, sertraline acetate has advantageous mechanical properties and is chemically and physically stable. These properties permit easy handling of sertraline during formulation of dosage forms and result in tablets which are physically and chemically sable during storage and use.

The instant L-lactate salt of sertraline is highly water soluble and as such is particularly well-suited for use in a controlled release, for example, sustained release, encapsulated solution or delayed release, dosage form of sertraline. Further, sertraline L-lactate has advantageous mechanical properties and is chemically and physically stable. These properties permit easy handing of sertraline during formulation of dosage forms and result in tablets which are physically and chemically stable during storage and use.

The instant L-aspartate salt of sertraline is highly water soluble and as such is particularly well-suited for use in a controlled release, for example, sustained release, encapsulated solution or delayed release, dosage form of sertraline.

Thus the present invention is directed, inter alia, to sertraline acetate.

The present invention is particularly directed to sertraline acetate having the X-ray crystal structure depicted in FIG. 1 and the atomic coordinates recited in Table 40-2.

The present invention is still further directed to sertraline acetate·¼ hydrate.

The present invention is also directed to a method for treating anorexia in a subject suffering from anorexia or the symptoms of anorexia comprising administering to said subject an effective amount of sertraline acetate.

The present invention is also directed to methods for treating impulse disorders such as trichotillomania, pathological gambling, kleptomania and pyromania in a subject suffering from one of said impulse disorders comprising administering to said subject an effective amount of sertraline acetate.

The present invention is also directed to methods for treating onychophagia in a subject suffering from onychophagia comprising administering to said subject an effective amount of sertraline acetate.

The present invention is also directed to methods for treating premenstrual syndrome (also referred to herein as "premenstrual dysphoric disorder") in a subject suffering from premenstrual syndrome comprising administering to said subject an effective amount of sertraline acetate.

The present invention is also directed to methods for treating psychotic disorders of the schizophrenic type in a subject suffering from said psychotic disorders or suffering from such symptoms as anxiety, agitation, tension, excessive aggression, social withdrawal or emotional withdrawal comprising administering to said subject an effective amount of sertraline acetate.

The present invention is also directed to methods for treating inflammatory disorders such as psoriasis and arthritis in a subject suffering from an inflammatory disorder or inflammatory disorders comprising administering to said subject an effective amount of sertraline acetate.

The present invention is also directed to methods for treating conditions characterized by a hyperactive immune system such as rheumatoid arthritis and lupus in a subject suffering from said conditions comprising administering to said subject an effective amount of sertraline acetate.

The present invention is also directed to methods for treating mental depression in a mentally-depressed subject comprising administering to said subject an effective amount of sertraline acetate.

The present invention is also directed to methods for treating anxiety-related disorders such as panic disorder, generalized anxiety disorder, agoraphobia, simple phobias, social phobia, posttraumatic stress disorder, obsessive-compulsive disorder and avoidant personality disorder in a subject suffering from one or more of said anxiety-related disorders comprising administering to said subject an effective amount of sertraline acetate.

The present invention is particularly directed to methods for treating anxiety-related disorders as described in the previous paragraph wherein said anxiety-related disorder is obsessive-compulsive disorder.

The present invention is also directed to methods for treating chemical dependency in a subject suffering from chemical dependency comprising administering to said subject an effective amount of sertraline acetate.

The present invention is further directed to pharmaceutical compositions comprising sertraline acetate and a pharmaceutically acceptable carrier or diluent The present invention is still further directed to pharmaceutical compositions comprising sertraline acetate having the X-ray crystal structure depicted in FIG. 1 and a pharmaceutically acceptable carrier or diluent.

The present invention is also directed to processes for preparing sertraline acetate comprising reacting a salt of sertraline with a base in the presence of a suitable organic solvent to form sertraline free base, partitioning said sertraline free base into an organic solvent and reacting said sertraline free base with acetic acid in the presence of a suitable organic solvent.

The present invention is particularly directed to processes as described in the immediately preceding paragraph wherein said salt of sertraline is sertraline hydrochloride.

The present invention is more particularly directed to processes as described in the immediately preceding paragraph wherein said solvent is hexane.

The present invention is further directed to processes for preparing sertraline acetate comprising reacting sertraline free base with acetic acid in the presence of a suitable organic solvent The present invention is particularly directed to processes as described in the immediately preceding paragraph wherein said solvent is hexane.

The present invention is also directed to processes for preparing sertraline acetate comprising reacting a salt of sertraline with a base in the presence of a suitable organic solvent to form sertraline free base, partitioning said sertraline free base into an organic solvent and reacting said sertraline free base with acetic acid in the presence of a suitable organic solvent and isolating said sertraline acetate from said solvent.

The present invention is also directed to sertraline L-lactate.

The present invention is particularly directed to a form of sertraline L-lactate having the X-ray crystal structure depicted in FIG. 3 and the atomic coordinates recited in Table 48-2.

The present invention is also directed to methods for treating anorexia in a subject suffering from anorexia or the symptoms of anorexia comprising administering to said subject an effective amount of sertraline L-lactate.

The present invention is also directed to methods for treating impulse disorders such as trichotillomania, pathological gambling, kleptomania and pyromania in a subject suffering from one of said impulse disorders comprising administering to said subject an effective amount of sertraline L-lactate.

The present invention is also directed to methods for treating premenstrual syndrome in a subject suffering from premenstrual syndrome comprising administering to said subject an effective amount of sertraline L-lactate.

The present invention is also directed to methods for treating onychophagia in a subject suffering from onychophagia comprising administering to said subject an effective amount of sertraline L-lactate.

The present invention is also directed to methods for treating psychotic disorders of the schizophrenic type in a subject suffering from said psychotic disorders or suffering from such symptoms as anxiety, agitation, tension, excessive aggression, social withdrawal or emotional withdrawal comprising administering to said subject an effective amount of sertraline L-lactate.

The present invention is also directed to methods for treating inflammatory disorders such as psoriasis and arthritis in a subject suffering from an inflammatory disorder or inflammatory disorders comprising administering to said subject an effective amount of sertraline L-lactate.

The present invention is also directed to methods for treating conditions characterized by a hyperactive immune system such as rheumatoid arthritis and lupus in a subject suffering from said conditions comprising administering to said subject an effective amount of sertraline L-lactate.

The present invention is also directed to methods for treating mental depression in a mentally-depressed subject comprising administering to said subject an effective amount of sertraline L-lactate.

The present invention is also directed to methods for treating anxiety-related disorders such as panic disorder, generalized anxiety disorder, agoraphobia, simple phobias, social phobia, posttraumatic stress disorder, obsessive-compulsive disorder and avoidant personality disorder in a subject suffering from one or more of said anxiety-related disorders comprising administering to said subject an effective amount of sertraline L-lactate.

The present invention is particularly directed to methods for treating anxiety-related disorders as described in the previous paragraph wherein said anxiety-related disorder is obsessive-compulsive disorder.

The present invention is also directed to methods for treating chemical dependency in a subject suffering from chemical dependency comprising administering to said subject an effective amount of sertraline L-lactate.

The present invention is further directed to pharmaceutical compositions comprising sertraline L-lactate and a pharmaceutically acceptable carrier or diluent.

The present invention is still further directed to pharmaceutical compositions comprising sertraline L-lactate having the X-ray crystal structure depicted in FIG. 3 and a pharmaceutically acceptable carrier or diluent The present intention is also directed to processes for preparing sertraline L-lactate comprising reacting a salt of sertraline with a base in the presence of a suitable organic solvent to form sertraline free base, partitioning said sertraline free base into an organic solvent and reacting said sertraline free base with L-lactic acid in the presence of a suitable organic solvent.

The present invention is particularly directed to processes as described in the immediately preceding paragraph wherein said salt of sertraline is sertraline hydrochloride.

The present invention is more particularly directed to processes as described in the immediately preceding paragraph wherein said solvent is ethyl acetate.

The present invention is also particularly directed to processes for preparing sertraline L-lactate comprising reacting sertraline mandelate with a base in the presence of a suitable organic solvent to form sertraline free base, partitioning said sertraline base into an organic solvent and reacting said sertraline free base with L-lactic acid.

The present invention is more particularly directed to processes as described in the immediately preceding paragraph wherein said solvent is ethyl acetate.

The present invention is further directed to processes for preparing sertraline L-lactate comprising reacting sertraline free base with L-lactic acid in the presence of a suitable organic solvent.

The present invention is particularly directed to processes as described in the immediately-preceding paragraph wherein said solvent is ethyl acetate.

The present invention is also directed to processes for preparing sertraline L-lactate comprising reacting a salt of sertraline with a base in the presence of a suitable organic solvent to form sertraline free base, partitioning said sertraline free base into an organic solvent and reacting said sertraline free base with L-lactic acid in the presence of a suitable organic solvent and isolating said sertraline L-lactate from said solvent.

The present invention is also directed to sertraline L-aspartate.

The present invention is also directed to methods for treating anorexia in a subject suffering from anorexia or the symptoms of anorexia comprising administering to said subject an effective amount of sertraline L-aspartate.

The present invention is also directed to methods for treating impulse disorders such as trichotillomania, pathological gambling, kleptomania and pyromania in a subject suffering from one of said impulse disorders comprising administering to said subject an effective amount of sertraline L-aspartate.

The present invention is also directed to methods for treating onychophagia in a subject suffering from onychophagia comprising administering to said subject an effective amount of sertraline L-aspartate.

The present invention is also directed to methods for treating premenstrual syndrome in a subject suffering from premenstrual syndrome comprising administering to said subject an effective amount of sertraline L-aspartate.

The present-invention is also directed to methods for treating psychotic disorders of the schizophrenic type in a subject suffering from said psychotic disorders or suffering from such symptoms as anxiety, agitation, tension, excessive aggression, social withdrawal or emotional withdrawal comprising administering to said subject an effective amount of sertraline La-aspartate.

The present invention is also directed to methods for treating inflammatory disorders such as psoriasis and arthritis in a subject suffering from an inflammatory disorder or inflammatory disorders comprising administering to said subject an effective amount of sertraline L-aspartate.

The present invention is also directed to methods for treating conditions characterized by a hyperactive immune system such as rheumatoid arthritis and lupus in a subject suffering from said conditions comprising administering to said subject an effective amount of sertraline L-aspartate.

The present invention is also directed to methods for treating mental depression in a mentally-depressed subject comprising administering to said subject an effective amount of sertraline L-aspartate.

The present invention is also directed to methods for treating anxiety-related disorders such as panic disorder, generalized anxiety disorder, agoraphobia, simple phobias, social phobia, posttraumatic stress disorder, obsessive-impulsive disorder and avoidant personality disorder in a subject suffering from one or more of said anxiety-related disorders comprising administering to said subject an effective amount of sertraline L-aspartate.

The present invention is particularly directed to methods for treating anxiety-related disorders as described in the previous paragraph wherein said anxiety-related disorder is obsessive-compulsive disorder.

The present invention is also directed to methods for treating chemical dependency in a subject suffering from chemical dependency comprising administering to said subject an effective amount of sertraline L-aspartate.

The present invention is further directed to pharmaceutical compositions comprising sertraline L-aspartate and a pharmaceutically acceptable carrier or diluent.

The present invention is also directed to processes for preparing sertraline L-aspartate comprising reacting a salt of sertraline with a base in the presence of a suitable organic solvent to form sertraline free base, partitioning said sertraline free base into an organic solvent and reacting said sertraline free base wit aspartic acid in the presence of a suitable organic solvent.

The present invention is particularly directed to processes as described in the immediately preceding paragraph wherein said salt of sertraline is sertraline hydrochloride.

The present invention is more particularly directed to processes as described in the immediately preceding paragraph wherein said solvent is hexane.

The present invention is further directed to processes for preparing sertraline L-aspartate comprising reacting sertraline free base with aspartic acid in the presence of a suitable organic solvent.

The present invention is particularly directed to processes as described in the immediately preceding paragraph wherein said solvent is hexane.

The present invention is also directed to processes for preparing sertraline L-aspartate comprising reacting a salt of sertraline with a base in the presence of a suitable organic solvent to form sertraline free base, partitioning said sertraline free base into an organic solvent and reacting said sertraline free base with aspartic acid in the presence of a suitable organic solvent and isolating said sertraline L-aspartate from said solvent.

DETAILED DISCUSSION

Sustained Release

Figure 1:
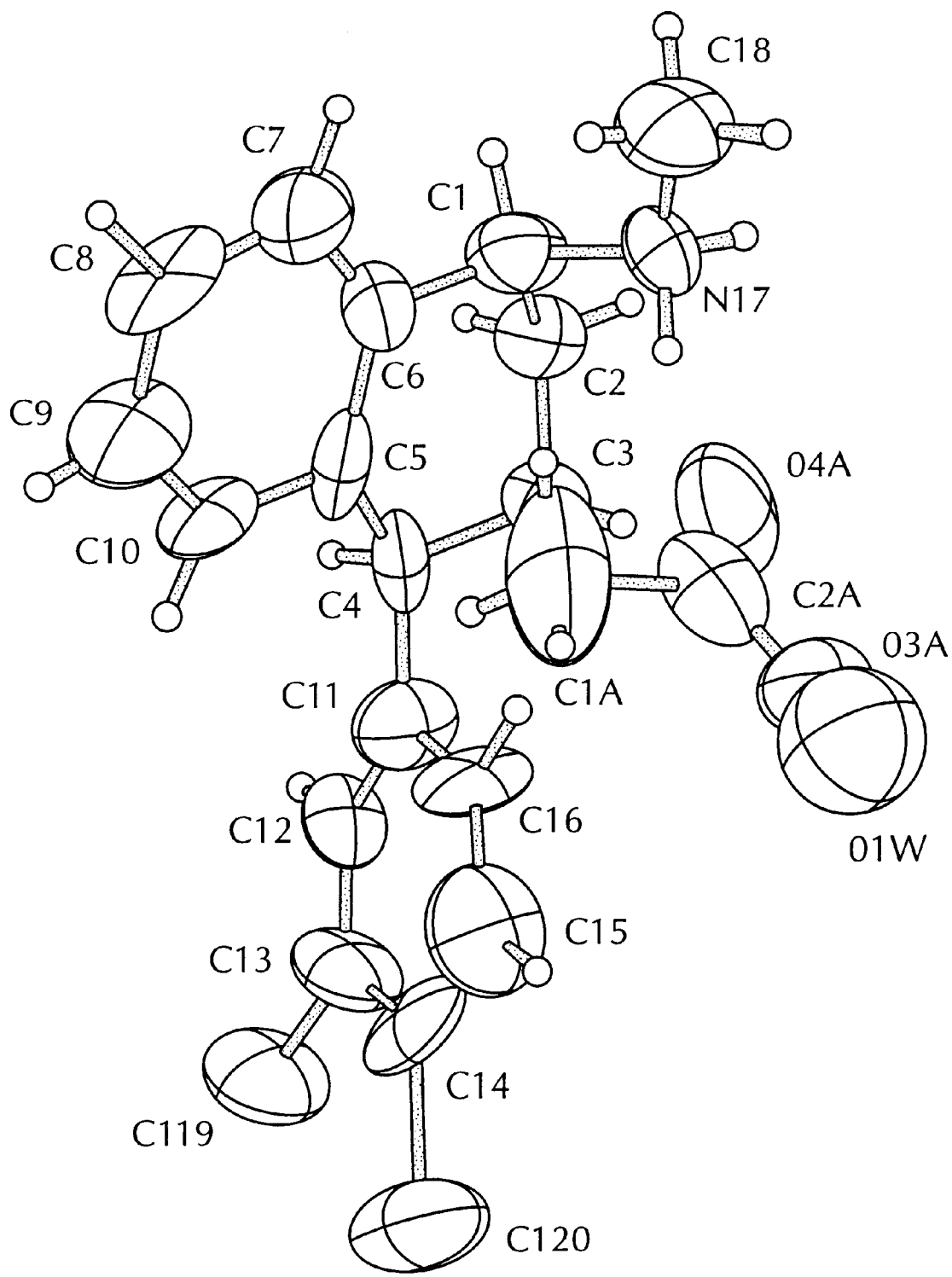
FIG. 1 is an X-ray crystal structure of sertraline acetate as derived from single crystal X-y crystallography. (Atomic coordinates).
Figure 2:
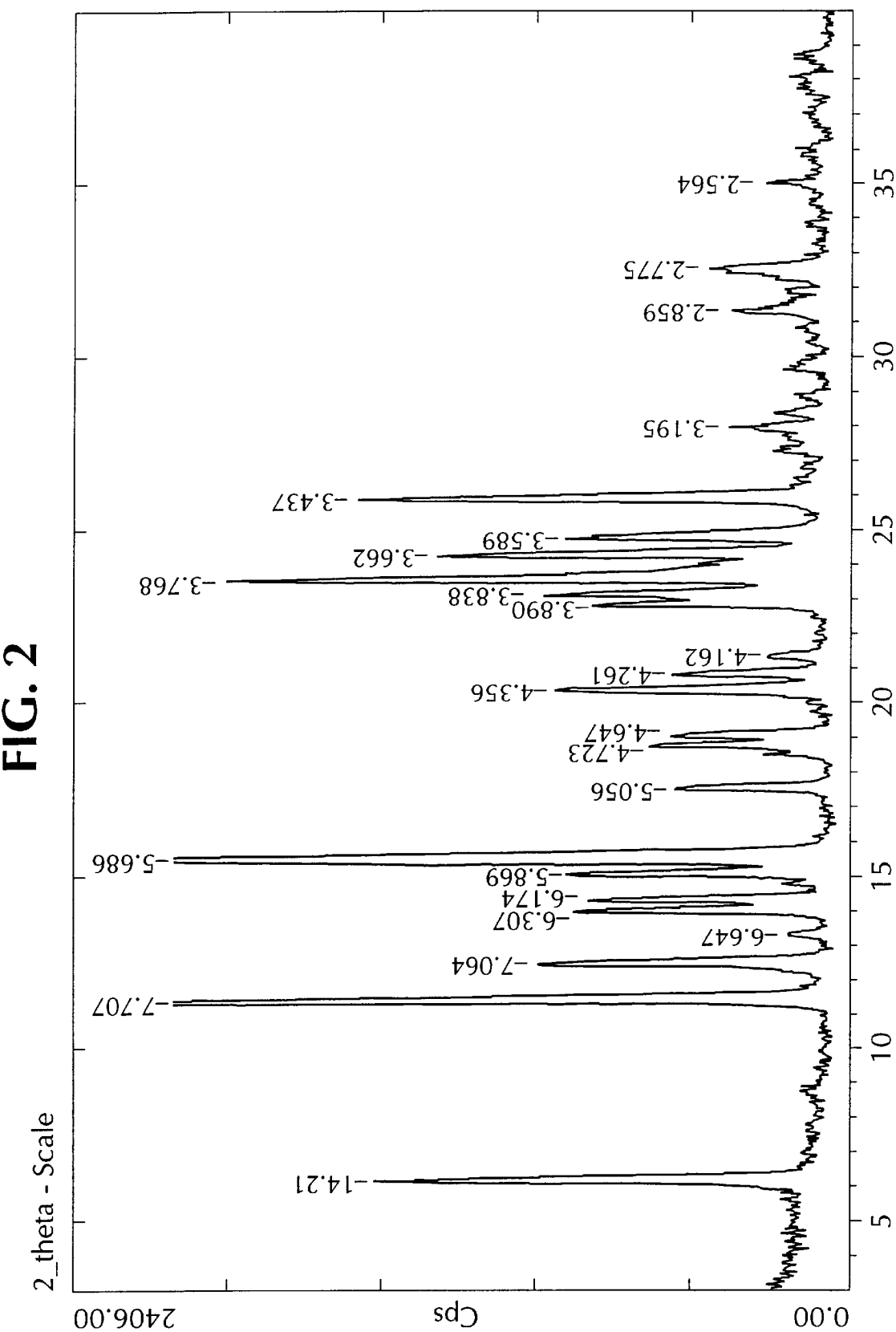
FIG. 2 is a characteristic X-ray diffraction pattern showing that sertraline acetate is crystalline. (Vertical Axis: Intensity (CPS); Horizontal Axis. Two theta (degrees)).

The sustained-release dosage forms of this invention can be widely implemented. For purposes of discussion, not limitation, the many embodiments hereunder can be grouped into classes according to design and principle of operation.

The first class of sustained release dosage forms described below is matrix systems which include but are not limited to 1) non-eroding matrices, tablets, multiparticulates, and hydrogel-based system; 2) hydrophilic eroding, dispersible or dissolvable matrix systems, tablets and multiparticulates; and 3) coated matrix systems. The second class consists of reservoir systems where release of the drug is modulated by a membrane, such as capsules, and coated tablets or multiparticulates. The third class consists of osmotic-based systems such as 1) coated bilayer tablets; 2) coated homogeneous tablet cores; 3) coated multiparticulates; and 4) osmotic capsules. The fourth class consists of swellable systems where drug is released by swelling and extrusion of the core components out through a passageway in a coating or surrounding shell or outer layer.

A first class includes matrix systems, in which sertraline is dissolved, embedded or dispersed in a matrix of another material that serves to retard the release of sertraline into an aqueous environment (i.e., the lumenal fluid of the GI tract). When sertraline is dissolved, embedded or dispersed in a matrix of this sort, release of the drug takes place principally from the surface of the matrix. Thus the drug is released from the surface of a device which incorporates the matrix after it diffuses trough the matrix into the surrounding fluid or when the surface of the device dissolves or erodes, exposing the drug. In some embodiments, both mechanisms can operate simultaneously. The matrix systems may be large, i.e., tablet sized (about 1 cm), or small (<0.3 cm). The system may be unitary, it may be divided as previously discussed by virtue of being composed of several sub-units (for example, several tablets-which constitute a single dose) which are administered substantially simultaneously, it may consist of several small tablets within a capsule, or it may comprise a plurality of particles, referred to herein as a multiparticulate. A multiparticulate can have numerous formulation applications. For example, a multiparticulate may be used as small beads or a powder for filling a capsule shell, it may be compressed into a tablet, or it may be used per se for mixing with food (for example ice cream) to increase palatability, or as a sachet that may be dispersed in a liquid, such as fruit juice or water.

The multiplicity of variables affecting release of sertraline from matrix devices permits abundant flexibility in the design of devices of different materials, sizes, and release times. Examples of modifications of sertraline release profiles from the specific embodiments of the examples within the scope of this invention are disclosed in detail below.

Non-eroding matrix tablets that provide sustained-release of sertraline can be made with sertraline free base and with a wide range of sertraline salts such as sertraline HCl, sertraline lactate, sertraline acetate and sertraline aspartate and water insoluble materials such as waxes, cellulose, or other water insoluble polymers. Matrix materials useful for the manufacture of these dosage forms include microcrystalline cellulose such as Avicel (rid trademark of FMC Corp., Philadelphia, Pa.), including grades of microcrystalline cellulose to which binders such as hydroxypropyl methyl cellulose have been added, waxes such as paraffin, modified vegetable oils, carnauba wax, hydrogenated castor oil, beeswax, and the like, as well as polymers such as cellulose, cellulose esters, cellulose ethers, poly(vinyl chloride), poly (vinyl acetate), copolymers of vinyl acetate and ethylene, polystyrene, and the like. Water soluble binders or release modifying agents which can optionally be formulated into the matrix include water-soluble polymers such as hydroxypropyl cellulose (HPC), hydroxypropyl methyl cellulose HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. In addition, materials which function as release-modifying agents include water-soluble materials such as sugars or salts. Preferred water-soluble materials include lactose, sucrose, glucose, and mannitol, as well as HPC, HPMC, and PVP. In addition solubilizing acid excipients such as malic acid, citric acid, erythorbic acid, ascorbic acid, adipic acid, glutamic acid, maleic acid, aconitic acid, and aspartic acid and solubilizing excipients such as partial glycerides, glycerides, glyceride derivatives, polyethylene glycol esters, polypropylene glycol esters, polyhydric alcohol esters, polyoxyethylene ethers, sorbitan esters, polyoxyethylene sorbitan esters, saccharide esters, phospholipids, polyethylene oxide-polypropylene oxide block co-polymers, and polyethylene glycols, can be incorporated into matrix tables to increase the release rate of sertraline, increase the total quantity of sertraline released, and potentially increase absorption and consequently the bioavailability of sertraline, particularly from matrix formulations that release sertraline over a period of six hours or longer.

In addition to components of the matrix system, the size of the matrix system can affect the rate of sertraline release, therefore, a large matrix system such as a tablet will, in general, have a different composition from a small one such as a multiparticulate to achieve similar release profiles. The effect of the size of the matrix system on the kinetics of sertraline release follows scaling behavior well known in the study of diffusion. By way of illustration, the following table shows the difussion coefficient of sertraline through the matrix required to achieve a characteristic time for release of 10 hours for matrix systems of different sizes that release sertraline by a diffusive-based mechanism (rather than an eroding or in combination with an eroding mechanism).

| radius (cm) | diffusion coefficient (cm$^2$/s) |
| --- | --- |
| 0.0025 (50 μm diameter) | $1.7 \times 10^{-10}$ |
| 0.1 (2 mm diameter) | $3 \times 10^{-7}$ |
| 0.5 (1 cm diameter) | $7 \times 10^{-6}$ |

The above table illustrates that diffusion-coefficients necessary to achieve the target characteristic time of release can change by orders of magnitude as the desired size of the device changes. Matrix materials which may be used to provide a sertraline diffusion coefficient at the low end of the diffusion coefficient scale are polymers such as cellulose acetate. Conversely, materials at the upper end of the scale are materials such as polymers which form hydrogels when hydrated. The rate of diffusion for any particular device can accordingly be tailored by the material or materials selected, and the structure of the matrix.

For purposes of further illustration, to obtain a sustained-release non-eroding matrix in a particle of about 50 µm in diameter, a matrix material of a polymer such as cellulose acetate or a similar material will likely be required, the slow diffusing matrix material tending to offset the short distances characteristic of small particle size. By contrast in order to obtain sustained-release in a large (e.g., 1 cm) device, a material which is more liquid-like (e.g., a hydrogel, see below) or with greater porosity will likely be red. For devices of an intermediate size, e.g., about 1 mm in diameter, a matrix composition of intermediate characteristics can be employed.

It is also noted tat the effective diffusion coefficient of sertraline in a matrix may be increased to the desired value by the addition of plasticizers, pores, or pore-inducing additives, as known in the art Slow-hydrating materials may also be used to effectively reduce the diffusion rates of sertraline, particularly at times shortly after administration. In addition to changing the effective diffusion coefficient, the release rate can also be altered by the inclusion of more soluble salt forms (relative to the free base) such as sertraline lactate, sertraline acetate, or sertraline aspartate, or excipients such as acids and/or surfactant-like compounds that solubilize sertraline and minimize gelation, particularly in the presence of chloride ions.

A further sustained release non-eroding matrix-system comprises sertraline dispersed in a hydrogel matrix. This embodiment differs from the hydrophilic matrix tablet discussed below in that the hydrogel of this embodiment is not a compressed tablet of soluble or erodible granular material, but rather a monolithic polymer network. As known in the art, a hydrogel is a water-swellable network polymer. Hydrogels can be made in many geometries, such as caplets, tablets, and multiparticulates. As an example, tablets can be prepared by standard techniques containing 10 to 80% of a crosslinkable polymer. Once tablets are formed the polymer can be crosslinked via a chemical crosslinking agent such as gluteraldehyde or via UV irradiation forming a hydrogel matrix. Hydrogels are preferred materials for matrix devices because they can absorb or be made to contain a large volume fraction of water, thereby permitting diffusion of solvated drug within the matrix. Diffusion coefficients of drugs in hydrogels are characteristically high, and for highly water-swollen gels, the diffusion coefficient of the drug in the gel may approach the value impure water. This high diffusion coefficient permits practical release rates from relatively large devices (i.e., it is not necessary to form microparticles). Although hydrogel devices can be prepared, loaded with sertraline, stored, dispensed and dosed in the fully hydrated state, it is preferred that they be stored, dispensed, and dosed in a dry state. In addition to stability and convenience, dry state dosing of hydrogel devices can provide good sertraline release kinetics due to Case II transport (i.e. combination of swelling of hydrogel and diffusion of drug out through the swollen hydrogel). Preferred materials for forming hydrogels include hydrophilic vinyl and acrylic polymers, polysaccharides such as calcium alginate, and poly(ethylene oxide). Especially preferred are poly(2-hydroxyethyl methacrylate), poly(acrylic acid), poly(methacrylic acid, poly(N-vinyl-2-pyrolidinone), poly(vinyl alcohol) and their copolymers with each other and with hydrophobic monomers such as methyl methacrylate, vinyl acetate, and the like. Also preferred are hydrophilic polyurethanes containing large poly(ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated.

Non-eroding matrix tablets can be made by tabletting methods common in the pharmaceutical industry. Preferred embodiments of non-eroding matrix tablets contain 10 to 80%/ sertraline, 5 to 50% insoluble matrix materials such as cellulose, cellulose acetate, or ethylcellulose, and optionally 5 to 85% plasticizers, pore formers or solubilizing excipients, and optionally about 0.25 to 2% of a tabletting lubricant, such as magnesium stearate, sodium stearyl fumarate, zinc stearate, calcium stearate, stearic acid, polyethyleneglycol-8000, talc, or mixtures of magnesium stearate with sodium lauryl sulfate. These materials can be blended, granulated, and tabletted using a variety of equipment common to the pharmaceutical industry.

A non-eroding matrix multiparticulate comprises a plurality of sertraline-containing particles, each particle comprising a mixture of sertraline with one or more excipients selected to form a matrix capable of limiting the dissolution rate of the sertraline into an aqueous medium. The matrix materials useful for this embodiment are generally water-insoluble materials such as waxes, cellulose, or other water-insoluble polymers. If needed, the matrix materials may optionally be formulated with water-soluble materials which can be used as binders or as permeability-modifying agents. Matrix materials useful for the manufacture of these dosage forms include microcrystalline cellulose such as Avicel (registered trademark of FMC Corp., Philadelphia, Pa.), including grades of microcrystalline cellulose to which binders such as hydroxypropyl methyl cellulose have been added, waxes such as paraffin, modified vegetable oils, carnauba wax, hydrogenated castor oil, beeswax, and the like, as well as synthetic polymers such as poly(vinyl chloride), poly(vinyl acetate), copolymer of vinyl acetate and ethylene, polystyrene, and the like. Water soluble release modifying agents which can optionally be formulated into the matrix include water-soluble polymers such as HPC, HPMC, methyl cellulose, PVP, PEO, PVA, xanthan gum, carrageenan, and other such natural and synthetic materials. In addition, materials which function as release-modifying agents include water-soluble materials such as sugars or salts. Preferred water-soluble materials include lactose, sucrose, glucose, and mannitol, as well as HPC, HPMC, and PVP. In addition any of the solubilizing acid or surfactant type excipients previously mentioned can be incorporated into matrix multiparticulates to increase the release rate of sertraline, increase the total quantity of sertraline released, and potentially increase absorption and consequently the bioavailability of sertraline, particularly from matrix formulations that release sertraline over a period of six hours or longer.

A preferred process for manufacturing matrix multiparticulates is the extrusion/spheronization process. For this process, the sertraline is wet-massed with a binder, extruded through a perforated plate or die, and placed on a rotating disks The extrudate ideally breaks into pieces which are rounded into spheres, spheroids, or rounded rods on the rotating plate. A preferred process and composition for this method involves using water to wet-mass a blend comprising about 20 to 75% of microcrystalline cellulose blended with, correspondingly, about 80 to 25% sertraline.

A preferred process for manufacturing matrix multiparticulates is the rotary granulation process. For this process sertraline and excipients such as microcrystalline cellulose are placed in a rotor bow in a fluid bed processor. The drug and excipient are fluidized, while spraying a solution that binds the drug and excipients together in granules or multiparticulates. The solution sprayed into the fluid bed can be water or aqueous solutions or suspensions of binding agents such as polyvynylpyrrolidone or hydroxypropylmethylcellulose. A preferred composition for this method can comprise 10 to 80% sertraline, 10 to 60% microcrystalline cellulose, and 0 to 25% binding agent.

A further preferred process for manufacturing matrix multiparticulates involves coating sertraline, matrix-forming excipients and if desired release-modifying or solubilizing excipients onto seed cores such as sugar seed cores known as non-pareils. Such coatings can be applied by many methods known in the pharmaceutical industry, such as spray-coating in a fluid bed coater, spray-drying, and granulation methods such as fluid bed or rotary granulation. Coatings can be applied from aqueous, organic or melt solutions or suspensions.

A further preferred process for manufacturing matrix multiparticulates is the preparation of wax granules. In this process, a desired amount of sertraline is stirred with liquid wax to form a homogeneous mixture, cooled and then forced through a screen to form granules. Preferred matrix materials are waxy substances. Especially preferred are hydrogenated castor oil and carnauba wax and stearyl alcohol.

A further preferred process for manufacturing matrix multiparticulates involves using an organic solvent to aid mixing of the sertraline with the matrix material. This technique can be used when it is desired to utilize a matrix material with an unsuitably high melting point that, if the material were employed in a molten state, would cause decomposition of the drug or of the matrix material, or would result in an unacceptable melt viscosity, thereby preventing mixing of sertraline with the matrix material. Sertraline and matrix material may be combined with a modest amount of solvent to form a paste, and then forced through a screen to form granules from which the solvent is then removed. Alternatively, sertraline and matrix material may be combined with enough solvent to completely dissolve the matrix material and the resulting solution (which may contain solid drug particles) spray dried to form the particulate dosage-form. This technique is preferred when the matrix material is a high-molecular weight synthetic polymer such as a cellulose ether or cellulose ester. Solvents typically employed for the process include acetone, ethanol, isopropanol, ethyl acetate, and mixtures of two or more.

A further process for manufacturing matrix multiparticulates involves using an aqueous solution or suspension of sertraline and matrix forming materials. The solution or suspension can be spray dried or sprayed or dripped into a quench bath or through a light chamber to initiate crosslinking of matrix materials and solidify the droplets. In this manner matrices can be made from latexes (e.g. dispersed ethylcellulose with a plasticizer such as oleic acid or with a volatile water miscible solvent such as acetone or ethanol) by spray-drying techniques. Matrices can also be made in this manner by crosslinking a water soluble polymer or gum. For example, sodium alginate can be crosslinked by spraying into a solution containing soluble calcium salts, polyvinyl alcohol can be crosslinked by spraying into a solution containing gluteraldehyde, and di- and tri-acrylates can be crosslinked by UV irradiation.

Once formed, sertraline matrix multiparticulates may be blended with compressible excipients such as lactose, microcrystalline cellulose, dicalcium phosphate, and the like and the blend compressed to form a tablet. Disintegrants such as sodium starch glycolate or crosslinked poly(vinyl pyrrolidone) are also usefully employed. Tablets prepared by this method disintegrate when placed in an aqueous medium (such as the GI tract), thereby exposing the multiparticulate matrix which releases sertraline therefrom. Sertraline matrix multiparticulates may also be filled into capsules, such as hard gelatin capsules.

A further embodiment of a matrix system has the form of a hydrophilic matrix tablet that eventually dissolves or disperses in water containing sertraline and an amount of hydrophilic polymer sufficient to provide a useful degree of control over the release of sertraline. Sertraline can be released from such matrices by diffusion, erosion or dissolution of the matrix, or a combination of these mechanisms. Hydrophilic polymers useful for forming a hydrophilic matrix include HPMC, HPC, hydroxy ethyl cellulose (HEC), PEO, PVA, xanthan gum; carbomer, carrageenan, and zooglan. A preferred material is HPMC. Other similar hydrophilic polymers may also be employed. In use, the hydrophilic material is swollen by, and eventually dissolves or disperses in, water. The sertraline release rate from hydrophilic matrix formulations may be controlled by the amount and molecular weight of hydrophilic polymer employed. In general, using a greater amount of the hydrophilic polymer decreases the release rate, as does using a higher molecular weight polymer. Using a lower molecular weight polymer increases the release rate. The release rate may also be controlled by the use of water-soluble additives such as sugars, salts, or soluble polymers. Examples of these additives are sugars such as lactose, sucrose, or mannitol, salts such as NaCl, KCl, $NaHCO_3$, and water soluble polymers such as PVP, low molecular weight HPC or HMPC or methyl cellulose. In general increasing the fraction of soluble material in the formulation increases the release rate. In addition any of the solubilizing acid excipients previously mentioned can be incorporated into matrix tablets to increase the release rate of sertraline, increase the total quantity of sertraline released, and potentially increase absorption and consequently the bioavailability of sertraline, particularly from matrix formulations that release sertraline over a period of six hours or longer. A hydrophilic matrix tablet typically comprises about 10 to 90% by weight of sertraline and about 80 to 10% by weight of polymer.

A preferred hydrophilic matrix tablet comprises, by weight, about 30% to about 80% sertraline, about 5% to about 35% HPMC, 0% to about 35% lactose, 0% to about 15% PVP, 0% to about 20% microcrystalline cellulose, and about 0.25% to about 2% magnesium stearate.

Mixtures of polymers and/or gums can also be utilized to make hydrophilic matrix systems. For example, homopolysaccharide gums such as galactomannans (e.g. locust bean gum or guar gum) mixed with heteropolyoacharide gums (e.g. xanthan gum or its derivatives) can provide a synergistic effect at in operation provides faster forming and more rigid matrices for the release of active agent (as disclosed in U.S. Pat Nos. 5,455,046 and 5,512,297). Optionally, crosslinking agents such as calcium salts can be added to improve matrix properties.

Hydrophilic matrix formulations that eventually dissolve or disperse can also be made in the form of multiparticulates. Hydrophilic matrix multiparticulates can be manufactured by the techniques described previously for non-eroding matrix multiparticulates. Preferred methods of manufacture are layering sertraline, a hydrophilic matrix material, and if desired release modifying agents onto sugar seed cores (e.g.

non-pareils) via a spray-coating process or to form multi-particulates by granulation, such as in a rotary granulation of sertraline, hydrophilic matrix material, and if desired release modifying agents.

The matrix systems as a class often exhibit non-constant release of the drug from the matrix. This result may be a consequence of the diffusive mechanism of drug release, and modifications to the geometry of the dosage form and/or coating or partially coating the dosage form can be used to advantage to make the release rate of the drug more constant as detailed below.

In a further embodiment, a sertraline matrix tablet is coated with an impermeable coating, and an orifice (for example, a circular hole or a rectangular opening) is provided by which the content of the tablet is exposed to the aqueous GI tract. These embodiments are along the lines of those presented in U.S. Pat. No. 4,792,448 to Ranade, and as described by Hansson et al., J. Pharm. Sci. 77 (1988) 322–324 herein incorporated by reference. The opening is typically of a size such that the area of the exposed underlying sertraline composition constitutes less than about 40% of the surface area of the device, preferably less than about 15%.

In another embodiment, a sertraline matrix tablet is coated with an impermeable material on part of its surface, e.g. on one or both tablet faces, or on the tablet radial surface.

In another embodiment, a sertraline matrix tablet is coated with an impermeable material and an opening for drug transport produced by drilling a hole through the coating. The hole may be through the coating only, or may extend as a passageway into the tablet.

In another embodiment, a sertraline matrix tablet is coated with an impermeable material and a passageway for drug transport produced by drilling a passageway through the entire tablet.

In another embodiment, a sertraline matrix tablet is coated with an impermeable material and one or more passageways for drug transport are produced by removing one or more strips from the impermeable coating or by cutting one or more slits through the coating, preferably on the radial surface or land of the tablet.

In another embodiment, a sertraline matrix tablet is shaped in the form of a cone and completely coated with an impermeable material. A passageway for drug transport is produced by cutting off the tip of the cone.

In another embodiment, a sertraline matrix tablet is shaped in the form of a hemisphere and completely coated with an impermeable material. A passageway for drug transport is produced by drilling a hole in the center of the flat face of the hemisphere.

In another embodiment, a sertraline matrix tablet is shaped in the form of a half-cylinder and completely coated with an impermeable material. A passageway for drug transport is produced by cutting a slit through (or removing a strip from) the impermeable coating along the axis of the half-cylinder along the centerline of the flat face of the half-cylinder.

Those skilled in the art will appreciate that the geometric modifications to the embodiments described above can be equivalently produced by more than one method. For example, cutting or drilling to make a passageway for drug transport can be achieved by other operations such as by a technique which produces the desired partial coating directly.

By "impermeable material" is meant a material having sufficient thickness and impermeability to sertraline such that the majority of sertraline is released through the passageway rather than the "impermeable material" during the time scale of the intended drug release (i.e., several hours to about a day). Such a coating can be obtained by selecting a coating material with a sufficiently low diffusion coefficient for sertraline and applying it sufficiently thickly. Materials for forming the impermeable coating of these embodiments include substantially all materials in which the diffusion coefficient of sertraline is less than about $10^{-7}$ cm$^2$/s. It is noted that the preceding diffusion coefficient can be amply sufficient to allow release of sertraline from a matrix device, as discussed above. However, for a device of the type now under discussion which has been provided with a macroscopic opening or passageway, a material with this diffusion coefficient is effectively impermeable to sertraline relative to sertraline transport through the passageway. Preferred coating materials include film-forming polymers and waxes. Especially preferred are thermoplastic polymers, such as poly(ethylene-co-vinyl acetate), poly(vinyl chloride), ethylcellulose, and cellulose acetate. These materials exhibit the desired low permeation rate of sertraline when applied as coatings of thickness greater than about 100 μm.

A second class of sertraline sustained-release dosage forms of this invention includes membrane-moderated or reservoir systems such as membrane-coated diffusion-based capsule, tablet, or multiparticulate. Capsules, tablets and multiparticulates can all be reservoir systems, such as membrane-coated diffusion-based. In this class, a reservoir of sertraline is surrounded by a rate-limiting membrane. The sertraline traverses the membrane by mass transport mechanisms well known in the art, including but not limited to dissolution in the membrane followed by diffusion across the membrane or diffusion through liquid-filled pores within the membrane. These individual reservoir system dosage forms may be large, as in the case of a tablet containing a single large reservoir, or multiparticulate, as in the case of a capsule containing a plurality of reservoir particles, each individually coated with a membrane. The coating can be non-porous, yet permeable to sertraline (for example sertraline may diffuse directly through the membrane), or it may be porous.

Sustained release coatings as known in the art may be employed to fabricate the membrane, especially polymer coatings, such as a cellulose ester or ether, an acrylic polymer, or a mixture of polymers. Preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotary bed coater.

If desired, the permeability of the coating may be adjusted by blending of two or more materials. A particularly useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores which facilitate release of the drug. The membrane coating can also be modified by the addition of plasticizers, as known in the art.

A particularly useful variation of the process for applying a membrane coating comprises dissolving the coating polymer in a mixture of solvents chosen such that as the coating dries, a phase inversion takes place in the applied coating solution, resulting in a membrane with a porous structure. Numerous examples of this type of coating system are given in European Patent Specification 0 357 369 B1, published Mar. 7, 1990, herein incorporated by reference.

The morphology of the membrane is not of critical importance so long as the permeability characteristics enumerated herein are met. However, specific membrane designs will have membrane morphology constraints in order to achieve the desired permeability. The membrane can be amorphous or crystalline. It can have any category of morphology produced by any particular process and can be, for example, an interfacially-polymerized membrane (which comprises a thin rate-limiting skin on a porous support), a porous hydrophilic membrane, a porous hydrophobic membrane, a hydrogel membrane, an ionic membrane, and other such membrane designs which are characterized by controlled permeability to sertraline.

A useful reservoir system embodiment is a capsule having a shell comprising the material of the rate-limiting membrane, including any of the membrane materials previously discussed, and filled with a sertraline drug composition. A particular advantage of this configuration is that the capsule may be prepared independently of the drug composition, thus process conditions that would adversely affect the drug can be used to prepare the capsule. A preferred embodiment is a capsule having a shell made of a porous or a permeable polymer made by a thermal forming process. An especially preferred embodiment is a capsule shell in the form of an asymmetric membrane; i.e., a membrane that has a thin dense region on one surface and most of whose thickness is constituted of a highly permeable porous material. A preferred process for preparation of asymmetric membrane capsules comprises a solvent exchange phase inversion, wherein a solution of polymer, coated on a capsule-shaped mold, is induced to phase by exchanging the solvent with a miscible non-solvent. Examples of asymmetric membranes useful in this invention are disclosed in the aforementioned European Patent Specification 0 357 369 B1.

Tablets can also be reservoir systems. Tablet cores containing sertraline can be made by a variety of techniques standard in the pharmaceutical industry. These cores can be coated with a rate-controlling coating as described above, which allows the sertraline in the reservoir (tablet core) to diffuse out through the coating at the desired rate.

Another embodiment of reservoir systems comprises a multiparticulate wherein each particle is coated with a polymer designed to yield sustained release of sertraline. The multiparticulate particles each comprise sertraline and one or more excipients as needed for fabrication and performance. The size of individual particles, as previously mentioned, is generally between about 50 $\mu$m and about 3 mm, although beads of a size outside this-range may also be useful. In general, the beads comprise sertraline and one or more binders. As it is generally desirable to produce dosage forms which are small and easy to swallow, beads which contain a high fraction of sertraline relative to excipients are preferred. Binders useful in fabrication of these beads include microcrystalline cellulose (e.g., Avicel®, FMC Corp.), HPC, HPMC, and related materials or combinations thereof. In general, binders which are useful in granulation and tabletting, such as starch, pregelatinized starch, and PVP may also be used to form multiparticulates.

Reservoir system sertraline multiparticulates may be prepared using techniques known to those skilled in the art, including, but not limited to, the techniques of extrusion and spheronization, wet granulation, fluid bed granulation, and rotary bed granulation. In addition, the beads may also be prepared by building the sertraline composition (drug plus excipients) up on a seed core (such as a non-pareil seed) by a drug-layering technique such as powder coating or by applying the sertraline composition by spraying a solution or dispersion of sertraline in an appropriate binder solution onto seed cores in a fluidized bed such as a Wurster coater or a rotary processor. An example of a suitable composition and method is to spray a dispersion of a sertraline/hydroxypropylcellulose composition in water. Advantageously, sertraline can be loaded in the aqueous composition beyond its solubility limit in water.

A preferred method for manufacturing the multiparticulate cores of this embodiment is the extrusion/spheronization process, as previously discussed for matrix multiparticulates. A preferred process and composition for this method involves using water to wet-mass a blend of about 5 to 75% of microcrystalline cellulose with correspondingly about 95 to 25% sertraline. Especially preferred is the use of about 5–30% microcrystalline cellulose with correspondingly about 95–70% sertraline.

A preferred process for making multiparticulate cores of this embodiment is the rotary-granulation process, as previously discussed for matrix multiparticulates.

A preferred process for making multiparticulate cores of this embodiment is the process of coating seed cores with sertraline and optionally other excipients, as previously discussed for matrix multiparticulates.

A sustained release coating as known in the art, especially polymer coatings, may be employed to fabricate the membrane, as previously discussed for reservoir systems. Suitable and preferred polymer coating materials, equipment, and coating methods also include those previously discussed.

The rate of sertraline release from the coated multiparticulates can also be controlled by factors such as the composition and binder content of the drug-containing core, the thickness and permeability of the coating, and the surface-to-volume ratio of the multiparticulates. It will be appreciated by those skilled in the art that increasing the thickness of the coating will decrease the release rate, whereas increasing the permeability of the coating or the surface-to-volume ratio of the multiparticulates will increase the release rate. If desired, the permeability of the coating may be adjusted by blending of two or more materials. A useful series of coatings comprises mires of water-insoluble and water-soluble polymers, for example, ethylcellulose and hydroxypropyl methylcellulose, respectively. A particularly useful modification to the coating is the addition of finely-divided water-soluble material, such as sugars or salts. When placed in an aqueous medium, these water soluble membrane additives are leached out of the membrane, leaving pores which facilitate delivery of the drug. The membrane coating may also be modified by the addition of plasticizers, as is known to those skilled in the art. A particularly useful variation of the membrane coating utilizes a mixture of solvents chosen such that as the coating dries, a phase inversion takes place in the applied coating solution, resulting in a membrane with a porous structure.

A preferred embodiment is a multiparticulate with cores comprising about 50 to 95% sertraline and 5 to 50% of one or more of the following: microcrystalline cellulose, PVP, HPC and HPMC. The individual cores-are-coated with either an aqueous dispersion of ethyl cellulose, which dries to form a continuous film, or a film of cellulose acetate containing PEG, sorbitol or glycerol as a release-modifying agent.

A third class of sertraline sustained-release dosage forms includes the osmotic delivery devices or "osmotic pumps" as they are known in the art. Osmotic pumps comprise a core containing an osmotically effective composition surrounded by a semipermeable membrane. The term "semipermeable" in this context means that water can pass through the membrane, but solutes dissolved in water permeate through the membrane at a rate significantly slower than water. In use, when placed in an aqueous environment, the device imbibes water due to the osmotic activity of the core composition. Owing to the semipermeable nature of the surrounding membrane, the contents of the device (including the drug and any excipients) cannot pass through the non-porous regions of the membrane and are driven by osmotic pressure to leave the device through an opening or passageway pre-manufactured into the dosage form or, alternatively, formed in situ in the GI tract as by the bursting of intentionally-incorporated weak points in the coating under the influence of osmotic pressure, or alternatively, formed in situ in the GI tract by dissolution and removal of water-soluble porosigens incorporated in the coating. The osmotically effective composition includes water-soluble species, which generate a colloidal osmotic pressure, and water-swellable polymers. The drug itself (if highly water-soluble) may be an osmotically effective component of the mixture. Sertraline acetate and lactate, having solubilities of 65 and 125 mg/ml, respectively, can provide an osmotic pressure in the me 2–4 atmospheres, enough to contribute some osmotic driving force. Because sertraline is a base, its solubility is generally higher at acidic pH. Therefore, the osmotic effectiveness of sertraline is aided by presence of acidic buffers in t formulation. The drug composition may be separated from the osmotically effective components by a movable partition or piston.

Materials useful for forming the semipermeable membrane include polyamides, polyesters, and cellulose derivatives. Preferred are cellulose ethers and esters. Especially preferred are cellulose acetate, cellulose acetate butyrate, and ethyl cellulose. Especially useful materials include those which spontaneously form one or more exit passageways, either during manufacturing or when placed in an environment of use. These preferred materials comprise porous polymers, the pores of which are formed by phase inversion during manufacturing, as described below, or by dissolution of a water-soluble component present in the membrane.

A class of materials which have particular utility for forming semipermeable membranes for use in osmotic delivery devices is that of porous hydrophobic polymers or vapor-permeable films, as disclosed by commonly assigned co-pending U.S. application Serial No. 08/096,144 filed Jul. 22, 1993 abandoned, herein incorporated by reference. These materials are highly permeable-to water, but highly impermeable to solutes dissolved in water. These materials owe their high water permeability to the presence of numerous microscopic pores (i.e., pores which are much larger than molecular dimensions). Despite their porosity, these materials are impermeable to molecules in aqueous solution because liquid water-does not wet the pores. Water in the vapor phase is easily able to pass across membranes made from these materials. Such membranes are also known as vapor permeable membranes.

A preferred embodiment of this class of osmotic delivery devices consists of a coated bi-layer tablet. The coating of such a tablet comprises a membrane permeable to water but substantially impermeable to sertraline and excipients contained within. The coating contains one or more exit passageways in communication with the sertraline-containing layer for delivering the drug composition. The tablet core consists of two layers: one layer containing the sertraline composition (including optional osmagents and hydrophilic water-soluble polymers) and another layer consisting of an expandable hydrogel, with or without additional osmotic agents. This type of delivery device is illustrated in Example 20.

When placed in an aqueous medium, the tablet imbibes water through the membrane, causing the sertraline composition to form a dispensible aqueous composition, and causing the hydrogel layer to expand and push against the sertraline composition, forcing the sertraline composition out of the exit passageway. The sertraline composition can swell aiding in forcing the sertraline out the passageway. Sertraline can be delivered from this type of delivery system either dissolved or dispersed in the composition forced out of the exit passageway.

The rate of sertraline delivery is controlled by such factors as the permeability and thickness of the coating, the osmotic pressure of the sertraline-containing layer, the water activity of the hydrogel layer, and the surface area of the device. Those skilled in the art will appreciate that increasing the thickness of the coating will reduce the release rate, whereas increasing the permeability of the coating or the water activity of the hydrogel layer or the osmotic pressure of the sertraline-containing layer or the surface area of the device will increase the release rate.

Exemplary materials which are useful to form the sertraline composition, in addition to the sertraline itself, include HPMC, PEO, and PVP, and other pharmaceutically-acceptable carriers. In addition, osmagents such as sugars or salts, especially sucrose, mannitol, or sodium chloride, may be added. Materials which are useful for forming the hydrogel layer include sodium carboxymethyl cellulose, poly (ethylene oxide), poly(acrylic acid), sodium (poly-acrylate) and other high molecular-weight hydrophilic materials. In addition, osmagents such as sugars or salts may be added. Particularly useful are poly (ethylene oxide)s having a molecular weight from about 5,000,000 to about 7,500,000.

Materials which are useful for forming the coating are cellulose esters, cellulose ethers, and cellulose ester-ethers. Preferred are cellulose acetate and ethylceollulose and optionally with PEG included as permeability modifying component.

The exit passageway must be located on the side of the tablet containing the sertraline composition. There may be more than one such exit passageway. The exit passageway may be produced by mechanical means or by laser drilling, or by creating a difficult-to-coat region on the tablet by use of special tooling during tablet compression or by other means. The rate of sertraline delivery from the device may be optimized so as to provide a method of delivering sertraline to a mammal for optimum therapeutic effect.

Osmotic systems can also be made with a homogeneous core surrounded by a semipermeable membrane coating. As illustrated in Examples 16, 17, and 18, sertraline can be incorporated into a tablet core that also contains other excipients that provide sufficient osmotic driving force and optionally solubilizing excipients such as acids or surfactant-type compounds. A semipermeable membrane coating can be applied via conventional tablet-coating techniques such as using a pan coater. A drug-delivery passageway can then be formed in this coating by drilling a hole in the coating, either by use of a laser or other mechanical means. Alternatively, the passageway may be formed by rupturing a portion of the coating or by creating a region on the tablet that is difficult to coat, as described above.

An embodiment of sertraline-sustained-release osmotic dosage forms of this invention comprises an osmotic sertraline containing tablet, which is surrounded by an asymmetric membrane, where said asymmetric membrane possesses one or more thin dense regions in addition to less dense porous regions. This type of membrane, similar to those used-in the reverse-osmosis industry, generally allows higher osmotic fluxes of water than can be obtained with a dense membrane. When applied to a drug formulation, e.g. a tablet, an asymmetric membrane allows high drug fluxes and well-controlled sustained drug release. This asymmetric membrane comprises a semipermeable polymeric material, that is, a material which is permeable to water, and substantially impermeable to salts and organic solutes such as drugs (e.g. sertraline).

Materials useful for forming the semipermeable membrane include polyamides, polyesters, and cellulose derivatives. Preferred are cellulose ethers and esters. Especially preferred are cellulose acetate, cellulose acetate butyrate and ethyl cellulose. Especially useful materials include those which spontaneously form one or more exit passageways, either during manufacturing or when placed in an environment of use. These preferred materials comprise porous polymers, the pores of which are formed by phase inversion during manufacturing, as described above, or by dissolution of a water-soluble component present in the membrane.

The asymmetric membrane is formed by a phase-inversion process. The coating polymer, e.g. ethylcellulose or cellulose acetate, is dissolved in a mixed solvent system comprising a mixture of solvents (e.g. acetone) and non-solvents (e.g. water) for the ethylcellulose or cellulose acetates. The components of the mixed solvent are chosen such that the solvent (e.g. acetone) is more volatile than the non-solvent (e.g. water). When a tablet is dipped into such a solution, removed and dried, the solvent component of the solvent mixture evaporates more quickly than the non-solvent. This change in solvent composition during drying causes a phase-inversion, resulting in precipitation of the polymer on the tablet as a porous solid with a thin dense outer region. This outer region possesses multiple pores through which drug delivery can occur.

In a preferred embodiment of an asymmetric membrane-coated tablet, the polymer/solvent/non-solvent mixture is sprayed onto a bed of tablets in a tablet-coating apparatus such as a Freund HCT-60 tablet coater. In this process, the tablet is coated with thick porous regions, and with a final outer thin dense region.

In the environment of use, e.g. the GI tract-water is imbibed through the semipermeable asymmetric membrane into the tablet core. As soluble material in the tablet core dissolves, an osmotic pressure gradient across toe membrane builds. When the hygrostatic pressure within the membrane enclosed core exceeds the pressure of the environment of use (e.g. the GI lumen), the sertraline-containing solution is "pumped" out of the dosage form through preformed pores in the semipermeable membrane. The constant osmotic pressure difference across the membrane results in a constant well-controlled delivery of sertraline to the use environment. A portion of the sertraline dissolved in the tablet also exits via diffusion.

Several illustrative formulations of this type of device are described in examples 16, 17, 18, and 19.

In this asymmetric-membrane-coated sertraline tablet embodiment, salts of sertraline are preferred due to their aqueous solubility. The hydrochloride, aspartate, acetate and lactate salts are especially preferred. Of these, thee acetate and lactate salts are most preferred. Also preferred are the inclusion of one or more solubilizing excipients, ascorbic acid, erythorbic acid, citric acid, glutamic acid, aspartic acid, partial glycerides, glycerides, glycerides derivatives, polyethylene glycol esters, polypropylene glycol esters, polyhydric alcohol esters, polyoxyethylene ethers, sorbitan esters, polyoxyethylene sorbitan esters, saccharide esters, phospholipids, polyethylene oxide-polypropylene oxide block co-polymers, and polyethylene glycols. Most preferred are solubilizing excipients ascorbic add, aspartic acid, glyceryl monocaprylate, glyceryl monostearate, glyceryl monolaurate, and C8–C10 partial glycerides.

Osmotic tablets can also be made with a core tablet containing osmagents and/or solubilizing excipients surrounded first by a drug containing layer and then second a semipermeable coating. The core tablet containing osmagents and/or solubilizing excipients can be made by standard tabletting methods known in the pharmaceutical industry. The drug containing layer may be applied around the core by spray-coating methods where a solution or slurry of drug and excipients is coated onto the tablet core. The drug and excipients may also be layered around the tablet core by making a "layered" type of configuration using a tablet press to form a second drug-containing layer around the tablet core as described in Example 19. This type of compression coating method can be used to apply a powder coating (without solvents) around a tablet-core. The semipermeable coating can then be applied to the layered core by many processes known in the art such as spray-coating or dip-coating methods described previously in these specifications.

Another embodiment of sustained release sertraline osmotic dosage forms of this invention consists of sertraline multiparticulates coated with an asymmetric membrane. Sertraline-containing multiparticulates are prepared by, for example, extrusion/spheronization or fluid bed granulation, or by coating non-pareil seeds with a mixture of sertraline and a water-soluble polymer, as described above. Sertraline-containing multiparticulates are then spray-coated with a solution of a polymer in a mixture of a solvent and a non-solvent, as described above, to form asymmetric-membrane-coated multiparticulates. This spray operation is preferably carried out in a fluid bed coating apparatus, e.g. a Glatt GPCG-5 fluid bed coater.

The polymer used for forming the semipermeable asymmetric membrane is chosen as described above for asymmetric membrane coated tablets. Likewise excipients for the multiparticulate cores can be chosen as described above for asymmetric-membrane coated tablets.

Osmotic capsules can be made using the same or similar components to those described above for osmotic tablets and multiparticulates. The capsule shell or portion of the capsule shell can be semipermeable and made of materials described above. The capsule can then be filled either by a powder or liquid consisting of sertraline, excipients that provide osmotic potential, and optionally solubilizing excipients. The capsule core can also be made such that it has a bilayer or multilayer composition a to the bilayer tablet described above.

A fourth class of sertraline sustained release dosage forms of this invention comprises coated swellable tablets and multiparticulates, as described in co-pending commonly assigned U.S. Serial No. 07/296,464, filed Jan. 12 1989 abandoned (published as EP 378404A2; Jul. 7, 1990), herein incorporated by reference. Coated swellable tablets comprise a tablet core comprising sertraline and a swelling material, preferably a hydrophilic polymer, coated with a membrane which contains holes or pores trough which, in the aqueous use environment, the hydrophilic polymer can extrude and carry out the-sertraline. Alternatively, the membrane may contain polymeric or low molecular weight water soluble porosigens which dissolve in the aqueous use environment, providing pores through which the hydrophilic polymer and sertraline may extrude. Examples of porosigens are water-soluble polymers such as hydroxypropylmethylcellulose, and low molecular weight compounds like glycerol, sucrose, glucose, and sodium chloride. In addition, pores may be formed in the coating by drilling holes in the coating using a laser or other mechanical means. In this fourth class of sertraline sustained release dosage forms, the membrane material may comprise any film-forming polymer, including polymers which are water permeable or impermeable, providing that the membrane deposited on the tablet core is porous or contains water-soluble porosigens or possesses a macroscopic hole for water ingress and sertraline release. Multiparticulates (or beads) may be similarly prepared, with a sertraline/swellable material core, coated by a porous or porosigen-containing membrane. Embodiments of this fourth class of sertraline sustained release dosage forms may also be multilayered, as described in EP 378 404 A2.

Sustained release formulations may also be prepared with a small portion of the dose released initially rapidly, followed by sustained release of the remaining majority portion of the dose. The combined sertraline release profile in this case is within the scope of sustained release dosage forms of this invention, i.e. sertraline is released at a rate less ton 40 mgA/hr, provided said dosage form (1) releases not more than 70% of the sertraline contained therein within the first hour following ingestion (or initiation of testing, and (2) releases sertraline at a rate of at least 1 mgA/hr.

When formulating sertraline, it may be advantageous to employ a high solubility salt, a formulation which otherwise increases sertraline solubility, or a combination of both collectively e to as a "high solubility form". The following is a discussion of the reasons and advantages accruing, from a formulations standpoint, from the use of high solubility forms of sertraline. Whether due to the salt form employed or the particular excipients employed in the dosage form, the high solubility form should effect a sertraline solubility of at least 10 mgA/ml.

Salts of sertraline or excipients that in combination with sertraline aid in solubilizing sertraline can be beneficial to almost all types of sustained-release dosage forms. Solubilized sertraline can enhance release from the dosage form by increasing the concentration gradient for diffusive based systems such as matrix dosage forms and reservoir dosage forms. Solubilized sertraline can also enhance delivery from osmotic dosage forms in that a more soluble sertraline can increase the osmotic pressure in the core and increase the sertraline concentration in the fluid that is pumped or extruded out of the dosage form. In addition, solubilized-sertraline can benefit sustained-release formulations by aiding absorption of drug from the G.I. tract. For example, higher concentrations of drug in the colon can increase absorption due to a higher concentration gradient across the colonic wall.

Solubilization can be particularly important for sustained-release sertraline formulations, since sertraline tends to form gels in many aqueous solutions, including solutions such as the intestinal fluids which contain chloride ions. Sertraline gels can be formed by simply introducing chloride ions into solutions of sertraline lactate or sertraline acetate. Similarly gels can be formed by introducing acids such as tartaric acid or combinations of acids and surfactants such as succinic acid and sodium lauryl sulfate to sertraline solutions. However, other acids and/or surfactant-like compounds can provide solubilizing effects, minimizing gel formation and providing a formulation basis for delivering sertraline in aqueous solutions containing chloride ions, such as intestinal fluids.

The gelling of sertraline is surprising, and the ability of certain additives to prevent this gelling is both surprising and unpredictable.

Gelling of sertraline in sustained release dosage forms can be particularly detrimental in non-eroding matrix systems, reservoir systems, and osmotic systems. In each of these types of sustained release formulations release of the drug is dependent on transport of the drug across a distance within the device (matrix or coating layer) to the surrounding fluid. This drug transport can occur by diffusive or convective mechanisms. In both mechanisms, formation of a gel can reduce transport by an order of magnitude or more and in many cases will result in devices that exhibit incomplete drug release (e.g., less than 70% of the total drug in the formulation).

Thus, it is advantageous to utilize methods to solubilize sertraline in sustained release formulations. One-method of solubilizing sertraline is to make sertraline salts that have higher solubility, such as sertraline lactate, sertraline acetate, and sertraline aspartate. Preferred salts exhibit solubilities in water that are over 3 times greater than the sertraline HCl sat, which has a solubility of about 3 mgA/ml.

Another method of solubilizing sertraline is to use an agent, referred to herein as a "solubilizing agent", which actually functions to increase and preferably maintain the solubility of sertraline (or a salt thereof) in a use environment relative to the solubility of sertraline in the same use environment when the solubilizing agent is not present.

Many solubilizing agents useful herein can be grouped into several broad categories:
1. Organic acids and organic acid salts;
2. Partial Glycerides, i.e., less than fully esterified derivatives of glycerin, including monoglycerides and diglycerides;
3. Glycerides;
4. Glyceride derivatives;
5. Polyethylene glycol esters;
6. Polypropylene glycol esters;
7. Polyhydric alcohol esters;
8. Polyoxyethylene ethers;
9. Sorbitan esters; and
10. Polyoxyethylene sorbitan esters.
11. Carbonate salts.

The amount of solubilizing agent which should be employed depends on the particular solubilizing agent.

In the case of solubilizing agents which are organic acids the preferred amount of solubilizer can be calculated as a ratio multiplied by the quantity of sertraline to be used, wherein the ratio is of organic acid solubility to solubility of sertraline salt (organic acid or salt solubility/sertraline or sertraline salt solubility)×quantity of sertraline where the solubilities referred to are in mg/ml. The above expression is approximate, and some adjustment may be advantageous for optimization. Generally the above expression will give a quantity which is plus or minus 25% of the final value employed, although higher quantities of solubilizing agent can be incorporated without any particular additional advantage. In addition, organic acid salts can be added to modify the pH and/or solubility of the organic acid, effectively optimizing the solubilization effect of the agents.

For other types of solubilizing agents listed, typically the amount of solubilizing agent employed in the dosage form will be 1 to 150%/ by weight of the amount of sertraline employed therein, preferably 1 to 100%, more preferably 3 to 75%. Amounts of solubilizing agent higher than 150% may be employed, although it is believed that in most cases no particular advantage would be provided.

Examples of organic acids useful in the invention include malic, citric, erythorbic, adipic, glutamic, aspartic, maleic, aconitic, and ascorbic acid. Preferred acids are citric, erythorbic ascorbic, glutamic, and aspartic. Salts of organic acids such as alkaline earth metal (magnesium, calcium) salts and alkali metal (lithium, potassium, sodium) salts are also effective as well as mixtures of organic acids and their salts. Calcium salts such as calcium carbonate, calcium acetate, calcium ascorbate, calcium citrate, calcium gluconate monohydrate, calcium lactobionate, calcium gluceptate, calcium levulinate, calcium pantothenate, calcium proprionate, calcium phosphate dibasic, and calcium saccharate are preferred organic acid salts.

Examples of compounds within the other categories mentioned above are summarized in Table 1.

TABLE 1

Solubilizing Agents

| Class | Examples, Chemical Name | Examples, Trade Designation, (Vendor) |
|---|---|---|
| Partial Glycerides | Glyceryl Monocaprylate | Monocaprylin ® (Sigma), Capmul ® MCM(Abitec), Imwitor ® 308 (Hüls) |
| | C8–C10 Partial Glycerides | Capmul ® MCM (Abitec), Imwitor ® 742 (Hüls), Imwitor ® 988 (Hüls) |
| | Glyceryl Monooleate | Myverol ® 18–99 (Eastman), Calgene ® GMO (Calgene), Capmul ® GMO(Abitec) |
| | Glyceryl Monolinoleate | Myverol ® 18–92 (Eastman) |
| | Glyceryl Monostearate | Imwitor ® 191 (Hüls) Calgene ® GSO(Calgene) |
| | Glyceryl Monolaurate | Imwitor ® 312 (Hüls) Calgene ® GLO (Calgene) |
| | Glyceryl Dilaurate | Capmul ® GDL (Abitec) |
| Glycerides | Triacetin | Triacetin (Sigma) |
| Glyceride Derivatives | PEG-Derivitized Glycerides | Cremophor ® RH40, Cremophor ® RH60 (BASF), Acconon ® CA5, CA-9, CA-15, W230, TGH (Abitec) |
| | Polyglycolized Glycerides | Gelucire ® 44/14, 42/12, 50/13, 53/10, 35/10, 48/09, 46/07, 62/05, 50/02; Labrasol ® (Gattefosse); Capmul ® 3GO; 3GS, 6G2O, 6G2S, 10G4O, 10G10O (Abitec) |
| Polyethylene glycol Esters | PEG 200 Monolaurate, PEG 400 Monolaurate, PEG 600 Monolaurate | Calgene ® 20-L, Calgene ® 40-L, Calgene ® 60-L |
| | PEG 200 Monostearate, PEG 400 Monostearate, PEG 600 Monostearate | Calgene ® 20-S, Calgene ® 40-S, Calgene ® 60-S |
| | PEG 200 Dilaurate, PEG 400 Dilaurate, PEG 600 Dilaurate | Calgene ® 22-L, Calgene ® 42-L Calgene ® 62-L |
| Polypropylene Glycol Esters | Propylene Glycol Dicaprylate | Captex ® 200 (Abitec) |
| Polyhydric Alcohol Esters | Diethylene Glycol Monolaurate | Calgene ® DGL |
| | Propylene Glycol Monolaurate | Calgene ® PGML |
| | Ascorbyl Palmitate | Ascorbyl Palmitate (Sigma) |
| Polyoxyethylene Ethers | PEG Lauryl Ether | Nonionic L-4 (Calgene) |
| | PEG Stearyl Ether | Nonionic S-20 (Calgene), Myrj 45, 52, 53, 59 (Sigma) |
| Sorbitan Esters | Sorbitan Monolaurate | Calgene ® SML, Span ® 20 (Sigma) |
| | Sorbitan Monooleate | Calgene ® SMO, Span ® 80 (Sigma) |
| Polyoxyethylene Sorbitan Esters | POE-20 Sorbitan Monolaurate | Calgene ® PSML-20, Span ® 20(Sigma), Tween ® 20 (Sigma), Capmul ® POE-L (Abitec) |
| | POE-20 Monooleate | Tween ® 80, PSMO-20 |
| Saccharide Esters | Sucrose Monolaurate | Ryoto LW-1540 (Chem Service) |
| Phospholipids | Phosphatidyl choline | Lecithin (Sigma) |
| | Mixed phospholipids | Emphos D70-30C (Witco) |
| Block Co-polymers | PEO-PPO Block Copolymers | Pluronic ® F-68, F127, L-62 (BASF) |
| Polyethylene Glycols | PEG 3350 | Various sources |

In addition other compounds useful as solubilizing agents in the invention are ethyl propionate, methyl paraben, propyl paraben, propyl galiate, niacinamide, ethyl vanillin, paraaminobenzoic acid, butylated hydroxyanisole, imidurea, and glycine. It is also noted that preferred compositions include mixtures of an organic acid with or without a corresponding organic acid salt, and one or more of the non-organic solubilizers listed above or in Table 1. It is also noted that it has generally been observed that in order to be most effective the solubilizer should have a solubility in the aqueous chloride-ion containing use environment of at least 1 mg/ml, and preferably greater than 5 mg/ml.

A preferred group of solubilizing agents, in addition to the preferred organic acids previously mentioned, includes those in Table 2.

TABLE 2

Preferred Solubilizing Agents

| Class | Examples, Chemical Name | Examples, Trade Names (source) |
| --- | --- | --- |
| Partial Glycerides | Glyceryl monocaprylate | Monocaprylin (sigma), Capmul ® MCM(Abitec), Imwitor ® 308 (Hüls) |
| | C8–C10 Partial Glycerides | Capmul ® MCM (Abitec), Imwitor ® 742 (Hüls), Imwitor ® 988 (Hüls) |
| | Glyceryl Monostearate | Imwitor ® 191 (Hüls) Calgene ® GSO(Calgene) |
| | Glyceryl Monolaurate | Imwitor ® 312 (Hüls) Calgene ® GLO (Calgene) |
| Glycerides | Triacetin | Triacetin (Sigma) |
| Sorbitan Esters | Sorbitan Monolaurate | Calgene ® SML, Span ® 20 (Sigma) |
| | Sorbitan Monooleate | Calgene ® SMO, Span ® 80 (Sigma) |
| Phospholipids | Phosphatidyl choline | Lecithin (Sigma) |
| | Mixed phospholipids | Emphos D70-30C (Witco) |
| Block Co-polymers | PEO-PPO Block Copolymers | Pluronic ® F-68, F127, L-62 (BASF) |
| Polyethylene Glycols | PEG 3350 | Various sources |

Note: Commercial vendors shown above are as follows:
Abitec Corp. Janesville, WI
BASF, Parsippany, NJ
Calgene Chemical Inc. Skokie, IL
Chem Service, Inc., West Chester, PA
Hüls America, Piscataway, NJ
Sigma, St. Louis, MO
Witco, Houston, Tx Preferred combinations of solubilizing agents include (1) an organic acid plus a salt of the same or a different organic acid, (2) an organic acid plus a non-ionic solubilizing agent such as any of those listed in Table 1, and (3) an organic acid plus a salt of the same or a different organic acid plus a non-ionic solubilizing agent Particularly preferred individual solubilizing agents include aspartic acid, glyceryl monocaprylate, glyceryl monolaurate, calcium acetate, ascorbic acid, citric acid, glutamic acid, and calcium carbonate. Aspartic acid, glyceryl monocaprylate, and calcium acetate are most preferred.

Also preferred are combinations of the preferred acids and preferred solubilizing surfactant-like compounds. A screening test useful for testing candidate solubilizers for use together with low solubility sertraline salts, such as sertraline hydrochloride, is set forth in the examples.

Preferred embodiments of sustained release formulations are osmotic systems comprising a core containing sertraline lactate or sertraline acetate or sertraline aspartate, an acid such as ascorbic, erythorbic, citric, glutamic, or aspartic acid, and if needed, a soluble sugar as an osmogent, binder material such as microcrystalline cellulose, swellable hydrophilic polymers, and a lubricant such as magnesium stearate. More preferred embodiments incorporate sertraline lactate or sertraline acetate.

Another preferred embodiment of sustained release formulations are osmotic systems comprising a core containing sertraline lactate or sertraline acetate, an acid such as ascorbic, erythorbic, citric, glutamic, or aspartic acid, a surfactant-like material such as partial glycerides, glycerides, sorbitan esters, phospholipids, polyethylene oxide-polypropylene oxide block co-polymers, and polyethylene glycols, and if needed, a soluble sugar to increase the osmotic pressure within the core, swellable hydrophilic polymers, binder material such as microcrystalline cellulose, and a lubricant such as magnesium stearate.

Another preferred embodiment of sustained release formulations are osmotic systems comprising a core containing sertraline-lactate or sertraline-acetate, a surfactant-like material such as partial glycerides, glycerides, sorbitan esters, phospholipids, polyethylene oxide-polypropylene oxide block co-polymers, and polyethylene glycols, a soluble sugar to increase the osmotic pressure within the core, and if needed, swellable hydrophilic polymers, binder material such as microcrystalline cellulose, and a lubricant such as magnesium stearate.

Preferred embodiments of sustained release formulations are osmotic systems such as any of the three osmotic systems discussed immediately above, and further coated with an asymmetric membrane coating made by a phase-inversion process. For use in these membrane systems sertraline lactate is especially preferred, as are ascorbic and aspartic acids, and partial glycerides.

Delayed Plus Sustained Release

As it is an additional object of this invention to reduce the exposure of the upper GI tract to high concentrations of sertraline in order to alleviate certain side effects (e.g. nausea, diarrhea, and regurgitation), an additional class of dosage forms includes those forms which incorporate a delay before the onset of sustained release of sertraline. Such dosage forms may be described as spatially-delayed plus sustained release sertraline dosage forms or temporally-delayed plus sustained release sertraline dosage forms, as described above. In principle, any sustained release device, including any of the numerous embodiments disclosed above, can be coated with an exterior, usually all-covering, coating which provides delayed release (i.e., of less than 1 mgA/hr) prior to the onset of sustained release. The coating can be of the type which provide a temporal delay or a spatial delay.

A first embodiment can be illustrated by a tablet comprising an immediate-release core comprising sertraline coated with a first coating of a polymeric material of the type useful for providing sustained release of sertraline from the core and a second coating of the type useful for delaying release of drugs once the dosage form is ingested. The second coating breaks down and becomes permeable once the tablet has left the stomach or after a preset time. The first (inner) coating is applied over and surrounds the tablet. The second (exterior or outer) coating is applied over and surrounds the first coating.

The tablet can be prepared by techniques well known in the art and contains a therapeutically useful amount of sertraline plus such excipients as are necessary to form the tablet by such techniques. The second coating is a delay coating, either spatially delayed or temporally delayed.

The first coating may be a sustained release coating as known in the art, especially polymer coatings, to fabricate the membrane, as previously discussed for reservoir systems. Suitable and preferred polymer coating materials, equipment, and coating methods also include those previously discussed.

Materials useful for preparing the second (delay) coat on the tablet include polymers known in the art as enteric coatings for pH-triggered delayed-release of pharmaceuticals. Such coatings are impermeable to sertraline at the pH of the stomach, but become permeable in the small intestinal environment, whether by dissolving, disintegrating, or otherwise breaking down, so that sertraline can freely pass through the coating. pH-sensitive polymers which are relatively insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, cellulose acetate trimellitate, styrene-maleic acid polyvinylacetate phthalate copolymer, styrene and maleic acid copolymers, polyacrylic add derivatives such as acrylic acid and acrylic ester copolymers, polymethacrylic acid and esters thereof, poly acrylic methacrylic acid copolymers, shellac, and vinyl acetate and crotonic add copolymers.

Preferred pH-sensitive polymers include shellac, phthalate derivatives, particularly cellulose acetate phthalate, polyvinylacetate phthalate, and hydroxypropylmethylcellulose phthalate; cellulose acetate trimellitate; polyacrylic acid derivatives, particularly copolymers comprising acrylic acid and at least one acrylic acid ester, polymethyl methacrylate blended with acrylic acid and acrylic ester copolymers; and vinyl acetate and crotonic acid copolymers.

A particularly preferred group of pH-sensitive polymers includes cellulose acetate phthalate, polyvinylacetate phthalate, hydroxypropylmethylcellulose phthalate, cellulose acetate trimellitate, anionic acrylic copolymers of methacrylic acid and methylmethacrylate, and copolymers comprising acrylic acid and at least one acrylic acid ester.

The thickness of the delayed release coating is adjusted to give the desired delay property. In general, thicker coatings are more resistant to erosion and, consequently, yield a longer delay. Preferred coatings range in thickness from about 20 $\mu$m to about 1 mm.

When ingested, the twice-coated tablet passes through the stomach, where the second coating prevents release of the sertraline (i.e. maintains a release rate less than 1 mg/hr) under the acidic conditions prevalent there. When the tablet passes out of the stomach (wherein certain side effects may be mediated) and into the small intestine, where the pH is higher, the second coating erodes or dissolves according to the physicochemical properties of the chosen material. Upon erosion or dissolution of the second coating, the first coating prevents immediate or rapid release of the sertraline and modulates the release so as to prevent the production of high concentrations, thereby minimizing side-effects.

A second embodiment of a delayed plus sustained release sertraline dosage form comprises a multiparticulate wherein each particle is dual coated as described above for tablets, first with a polymer designed to yield sustained release of the sertraline and then coated with a polymer designed to delay onset of release in the environment of the GI tract when the dosage form is ingested. The beads contain sertraline and may contain one or more excipients as needed for fabrication and performance. Multiparticulates which contain a high fraction of sertraline relative to binder are preferred. The multiparticulate may be of a composition and be fabricated by any of the techniques previously disclosed for multiparticulates used to make reservoir systems (including extrusion and spheronization, wet granulation, fluid bed granulation, and rotary bed granulation, seed building, and so forth).

The sustained release coating may be applied as known in the art. Suitable and preferred polymer coating materials, equipment, and coating methods also include those previously discussed.

The rate of sertraline release from the sustained-release-coated multiparticulates (i.e., the multiparticulates before they receive the delayed-release coating) and methods of modifying the coating are also controlled by the factors previously discussed for system sertraline multiparticulates.

The second membrane or coating for dual coated multiparticulates is a delayed-release coating which is applied over the first sustained-release coating, as disclosed above for tablets, and may be formed from the same materials. However, it is preferred to effect a sustained or controlled delivery of sertraline after the delayed-release coating has dissolved or eroded, therefore the benefits of this embodiment may be realized with a proper combination of delayed-release character with sustained-release character, and the delayed-release part alone may or may not necessarily conform to standard USP enteric criteria. The thickness of the delayed-release coating is adjusted to give the desired delay property. In general, thicker coatings are more resistant to erosion and, consequently, yield a longer delay.

A third embodiment of a delayed plus sustained release sertraline dosage form comprises eroding or non-eroding sertraline matrix cores, usually tablets or multiparticulates, as described above, coated with a coating which delays the commencement of sertraline sustained release until the coated tablet passes from the stomach to the duodenum or more distally. Polymers useful for the delay-release coating are pH-sensitive polymers described previously for coated reservoir tablets and multiparticulates.

pH-Triggered delayed plus sustained release sertraline dosage forms also may be formed by coating a matrix tablet or multiparticulate, or an osmotic tablet core or multiparticulate core with a single membrane comprising a mixture of a water-insoluble film-forming polymer, preferably a semipermeable polymer such as celluose acetate or ethylcellulose, and a pH sensitive polymer chosen from the list presented above. Preferred and particularly preferred pH-sensitive polymers for this embodiment are those preferred and particularly preferred pH-sensitive polymers described above. Preferred coating membranes of this embodiment comprise 10–70% pH-sensitive polymer. In general, thicker coating membranes will give a longer delay. In general, a lower pH-sensitive polymer content in the coating membrane will give a longer delay. The delay may be further controlled by incorporation, to a lesser or greater degree, of water-soluble polymers such as HPMC, and low molecular weight compounds like glycerol, sucrose, glucose, sodium chloride, citric acid, and fumaric acid. The delay time may be increased by choosing water-soluble membrane porosigens which have lower solubility or slower hydration. For example, citric acid as a membrane coating porosigen, relative to fumaric acid as a membrane coating porosigen, will cause a shorter delay, due to citric acid's higher solubility.

A fourth embodiment includes the osmotic dosage forms, as previously discussed in the section relating to "Sustained Release", but which are engineered to have a delay period longer than 15 minutes. Included in the osmotic embodiments are bilayer tablets comprising (1) a sertraline and osmogent-containing layer, wherein the osmogent may be lactose, sucrose, an organic acid or base, a salt, or the like, (2) a second layer containing a swelling polymer, for example polyethyleneoxide, and (3) a polymeric coating around the entire bilayer tablet, said coating comprising preferably a semipermeable polymer such as cellulose acetate along with one or more sertraline exit ports located on the sertraline-containing side of the tablet. The delay period can suitably be engineered into the osmotic dosage form by increasing the thickness of the membrane or by decreasing its porosity. Such a delay may have therapeutic advantages such as decreased side effects and decreased metabolic interactions with co-administered drugs.

Osmotic dosage forms which are delayed plus sustained release dosage forms of this invention include sertraline-containing core tablets and multiparticulates surrounded by a semipermeable asymmetric membrane. The core tablet contains sertraline, an osmotically effective solute, and optionally acidic sertraline solubilizers, surfactant-like inhibitors of sertraline gel formation, swelling polymers, viscosity altering polymers, and other common pharmaceutical excipients as needed. The drug itself, if highly water soluble, may be an osmotically effective component of the mixture. Salts of sertraline are preferred. The hydrochloride, aspartate, acetate, and lactate salts are especially preferred. Of these, the acetate and lactate are most preferred. Sertraline acetate and lactate, having solubilities of 64 and 125 mg/ml, respectively, can provide an osmotic pressure in the range 2–4 atmospheres, enough to contribute some osmotic driving force.

Materials useful for forming the semipermeable membrane include polyamides, polyesters, and cellulose derivatives. Preferred are cellulose ethers and esters. Especially preferred are cellulose acetate, cellulose acetate butyrate, and ethyl cellulose. Especially useful materials include those which spontaneously form one or more exit passageways, either during manufacture or when placed in an environment of use. These preferred materials are used to make porous coatings, the pores of which are formed by phase inversion during manufacturing, or by dissolution of a water-soluble component present in the membrane. Preparation of phase-inversion asymmetric semipermeable membranes has been described above in this disclosure.

In a preferred embodiment of an asymmetric-membrane-coated tablet, a polymer/solvent/non-solvent mixture is sprayed onto a bed of tablets in a tablet-coating apparatus such as a Freund HCT-60 tablet coater. In this embodiment, the tablet is coated with thick porous regions, and with a final outer thin dense region. To form a dense region that causes a delay, the spray solution is sprayed under conditions farther away from the conditions causing phase inversion than would be used to make asymmetric membrane-coated tablets without a delay period.

In the environment of use, e.g. in the GI tract, water is imbibed through the semipermeable asymmetric membrane into the tablet core. As soluble material in the tablet core dissolves, an osmotic pressure gradient across the membrane builds. When the hydrostatic pressure within the membrane-enclosed core exceeds the pressure of the environment of use (e.g. the GI lumen), the sertraline-containing solution is "pumped" out of the dosage form though the preformed pores in the semipermeable membrane.

It is preferred to include in the tablet or multiparticulate core one or more sertraline-solubilizing excipients, including ascorbic acid, erythorbic acid, citric acid, glutamic acid, aspartic acid, partial glycerides, glycerides, glyceride derivatives, polyethylene glycol esters, polypropylene glycol esters, polyhydric alcohol esters, polyoxyethylene ethers, sorbitan esters, polyoxyethylene sorbitan esters, saccharide esters, phospholipids, polyethylene oxide-polypropylene oxide block co-polymers, and polyethylene glycols. Most preferred are solubilizing excipients ascorbic acid, aspartic acid, glyceryl monocaprylate, glyceryl monostearate, glyceryl monolaurate, and C8–C10 partial glycerides.

The delay period may be engineered to be up to 3 hours or more by selection of the composition of the asymmetric membrane, e.g. by the selection of the ratio of membrane polymer (such as cellulose acetate or ethylcellulose) to plasticizer (such as PEG-3350 or other water-soluble plasticizer). Increasing the membrane thickness or the membrane polymer to plasticizer ratio results in a longer delay time. The delay may be further controlled by incorporation, to a lesser or greater degree, of water-soluble polymers such as HPMC, and low molecular weight compounds like glycerol, sucrose, glucose, sodium chloride, citric acid, and fumaric acid. The delay time may be increased by choosing water-soluble membrane porosigens which have lower solubility or slower hydration. For example, citric acid as a membrane coating porosigen, relative to fumaric acid as a membrane coating porosigen, will cause a shorter delay, due to citric acid's higher solubility. The delay time may be increased by incorporating a lower proportion of non-solvent in the coating solution to move slightly away from ideal phase inversion conditions. The delay time may be decreased by incorporating a larger proportion of osmotic excipients, or excipients with higher osmotic pressure, or solubilizers into the core formulation. Asymmetric membrane-coated osmotic tablet delayed plus sustained release sertraline dosage forms of this invention are exemplified in Examples 17 and 18.

A fifth embodiment of delayed plus sustained release dosage forms comprises coated swelling hydrogel tablets and multiparticulates, as described in copending commonly assigned U.S. Ser. No. 07/296,464, filed Jan. 12, 1989, abandoned, (published as EP 378404 A2; Jul. 7, 1990), herein incorporated by reference. Coated swellable tablets comprise a tablet core comprising sertraline and a swelling material, preferably a hydrophilic polymer, coated with a membrane which contains holes or pores through which, in the aqueous use environment, the hydrophilic polymer can extrude and carry out the sertraline. Alternatively, the membrane may contain polymeric or low molecular weight water soluble porosigens which dissolve in the aqueous use environment, providing pores through which the hydrophilic polymer and sertraline may extrude. Examples of porosigens are water-soluble polymers such as HPMC, and low molecular weight compounds like glycerol, sucrose, glucose, sodium chloride, citric acid, and fumaric acid. In addition, pores may be formed in the coating by drilling holes in the coating using a laser or other mechanical means. In this fifth embodiment of delayed plus sustained release sertraline dosage forms, the membrane material may comprise any film-forming polymer, including polymers which are water-permeable or impermeable, provided that be membrane deposited on the tablet core is porous or contains water-soluble porosigens, or possesses a macroscopic hole for water ingress and sertraline release.

For coated swelling hydrogel tablets and multiparticulates, preferred swelling polymers for the core include polyethylene oxide of molecular weights from 3000 to 500,000, and carboxymethylcelluose. Preferred coating polymers include cellulose acetate and ethylcellulose, and hydrophobic polymers such as ethylene vinyl acetate.

For coated swelling hydrogel and multiparticulates, the delay period may be engineered to be up to 3 hours or more by selection of the composition of the membrane, i.e. by the selection of the ratio of membrane to porosigen. Increasing the membrane thickness or the membrane polymer to porosigen ratio results in a longer delay time. The delay time may be increased by choosing water-soluble membrane porosigens which have lower solubility or slower hydration. For example, citric acid as a membrane coating porosigen, relative to fumaric acid as a membrane coating porosigen, will cause a shorter-delay, due to citric acid's higher solubility. The delay time may be decreased by incorporating a larger proportion of lower molecular weight (e.g. less than 20,000 daltons) swelling polymer into the core formulation.

A sixth embodiment is an enzyme-triggered system such as an enzyme-triggered supported liquid membrane coating of the type described in International Application PCT/US93/07463, published as WO 94/12159 on Jun. 9, 1994, herein incorporated by reference. The coating is a microporous hydrophobic membrane possessing a hydrophobic liquid entrained within the pores of the membrane. This membrane encloses a diffusive matrix core or an osmotically active core which contributes to the control of sertraline release after the dosage form has exited the stomach. The hydrophobic liquid is substantially impermeable to both the aqueous environment and the underlying sustained release formulation. The hydrophobic liquid is capable of change such that it becomes permeable to the aqueous environment. After ingestion of the dosage form by a mammal, sertraline release into the gastrointestinal system is delayed until the dosage form has exited the stomach and moved into the duodenum. The entrained hydrophobic liquid undergoes change which is enzymatically catalyzed in the lumen of the small intestine, and not in the stomach, such that the hydrophobic liquid in the delay coating pores breaks down so the membrane becomes permeable to water and saline. Exemplary hydrophobic liquids are triglycerides, fatty anhydrides, fatty acid esters of cholesterol, hydrophobic amino acid esters, and the like. Preferred triglycerides include triolein, trycaprylin, trilaurin, olive oil, palm oil, coconut oil, sesame seed oil, corn oil, peanut oil, soybean oil, and the like. Preferred fatty acid anhydrides include caprylic anhydride, lauric anhydride, myristic anhydride and the like. Mixtures of hydrophobic liquids may be used. Exemplary materials for the microporous hydrophobic support delay membrane or coating include cellulose esters, polycarbonates, polyalkenes, polystyrenes, polyvinyl esters, polysiloxanes, polyacrylates and polyethers. Preferably the hydrophobic microporous membrane with entrained hydrophobic liquid is impermeable to sertraline, until gastrointestinal enzymes have catalyzed a change in the hydrophobic oil, as described below.

In the environment of use, i.e., the small intestinal lumen, lipases and esterases degrade the aforementioned hydrophobic oils, forming surfactant products in the pores of the microporous membrane of this embodiment, thus producing aqueous channels through which the sertraline in the device core may exit through the microporous hydrophobic support membrane. Once the delay membrane becomes porous, release of the sertraline is controlled by the sustained release limitations of the underlying device or the porosity and thickness of the porous hydrophobic coating.

In an enzyme-triggered supported liquid delay membrane as disclosed above, hydrophobic oils may be used which are substrates for small intestinal proteases such as trypsin, carboxypeptidase and chymotrypsin. Exemplary oils are hydrophobic esters of amino acid derivatives.

In a further embodiment of a spatially-delayed plus sustained release sertraline dosage form, sustained release sertraline tablets, capsules, beads, or powders are coated with a coating which contains components which are enzymatically degraded by enzymes in the rumen of the small intestine, but not in the gastric lumen. The coating comprises waxes or triglycerides of natural or synthetic origin which are solid at body temperature. In preferred embodiments, 2–20% of a material which is liquid at body temperature, and which is degraded by small intestinal enzymes (e.g. trypsin, chymatrypsin, elastase, lipase), is included. Suitable enzymatically-labile liquids are those described above for "enzyme triggered supported liquid membrane devices". Preferred waxy coatings are applied at 3–20% of the weight of the uncoated sertraline tablet, capsule, bead, or powder.

In a seventh embodiment, a temporally-delayed sertraline dosage form, sustained release sertraline tablets, beads, or particles are prepared and are further coated with a water-soluble and/or water-disintegrable delay layer. In preferred embodiments, disintegrating and non-disintegrating sertraline matrix tablets or beads are coated with a temporal delay layer. Preferred delay coatings include hydoxypropylcellulose (HPC), hydroxypropylmethylcellulose (HPMC), polyethylene oxide (PEO), and polyvinyl pyrrolidone (PVP). For tablets this coating may be applied in a tablet coating apparatus such as an HCT-30, HCT-60, or HCT-130 Coater; available from Freund Inc. The tablets are coated with an aqueous solution of HPMC or other appropriate polymer to a final coating weight of 5–50% of the final of the coated tablet. Heavier coating weights give longer delays before the onset of sertraline release into a use environment such as the GI lumen. The delay time may also be increased by incorporating small to moderate quantities of poorly water-soluble polymers, including but not limited to ethylcellulose (EC), cellulose acetate (CA), and celluose acetate butyrate, into the coating formulation. For example, the coating formulation may consist of 95:5 HPMC/EC to 50:50 HPMC/EC, or 95:5 HPMC/CA to 50:50 HPMC/CA. In the case of such mixed polymer coating systems, it may be necessary to adjust the solvent composition to dissolve the mixture of water-soluble and poorly water-soluble polymers. For example, mixtures of acetone and water, or ethanol and water, may be used as needed. Beads and particles may be similarly coated using a fluid bed coating apparatus, such as a Glatt GPCG-5 coater. For beads, the coating comprises from about 10% to about 100% of tee weight of the uncoated bead core. For sertraline powders, the coating comprises from about 15% to about 200% of the weight of the uncoated bead core.

Salts

This invention relates to sertraline acetate, which can be prepared according to the following procedure.

The free base of sertraline is dissolved in a suitable organic solvent such as ethyl acetate; an unsaturated hydrocarbon such as hexane or pentane; an aromatic hydrocarbon, such as benzene or toluene; or a cyclic or acyclic ether such as dioxane, tetrahydrofuran, diethyl ether or methoxymethyl ether or a combination thereof or a combination of any of those solvents with water. A suitable organic solvent is any solvent in which the free base of sertraline is freely soluble, in which the acetate salt of sertraline is particularly insoluble and which facilitates the formation of the desired crystalline form. Hexane is preferred due to its ability to dissolve sertraline, its inability to dissolve sertraline acetate and for the quality of the crystals obtained upon granulation therewith. The temperature of the solution is maintained at room temperature or is raised to the boiling point of the solvent being used. It is preferred to raise the temperature to slightly below the boiling point of the solvent being used, generally between 30° C. and 60° C. When hexane is used, it is preferred to raise the temperature to approximately 40° C. An excess of acetic acid is then added to the reaction mixture. It is generally preferable to add one to two equivalents of acetic acid for every equivalent of sertraline. Typically, 1.1 equivalents of acetic acid is added. When the reaction is complete, sertraline acetate generally precipitates. Occasionally, to obtain a better yield of said sertraline acetate, the reaction mixture is cooled, generally to about room temperature or about 0° C. After precipitation of the salt, it is generally advantageous to continue to stir or granulate the precipitate. When granulating, it is ordinarily preferable to do so at room temperature or slightly above room temperature and no greater than 35° C. The crystals which form are isolated by filtration. The crystals of the acetate salt of sertraline are washed with hexane and are dried at elevated temperature and reduced pressure, generally 30–60° C. for 24 to 48 hours or a period of time sufficient to remove substantially all traces of hexane and any unreacted acetic acid.

Alternatively, sertraline acetate can be prepared directly from a salt of sertraline, for example, sertraline hydrochloride or sertraline mandelate, without isolation of the free base form of sertraline. Typically, sertraline hydrochloride is used in this preparation. When using this procedure, said salt of sertraline is slurried in water and dilute aqueous base is added dropwise or in small portions. The pH of the solution is monitored during the addition of base to prevent the addition of an excessive amount of base. Typically, the pH is maintained between about 6.5 to 9.5. Preferably, the pH is maintained at 8.5. Suitable aqueous bases which can be used in this reaction include sodium hydroxide, sodium carbonate, sodium bicarbonate, potassium carbonate and potassium bicarbonate. Preferably, aqueous sodium hydroxide is used. The free base of sertraline thus formed is partitioned into an immiscible organic solvent such as hexane, ethyl acetate, benzene, toluene or ethers such as diethyl ether, dioxane or methoxymethyl ether. Generally, hexane is preferred. The immiscible organic phase is separated from the aqueous phase and the organic phase is washed with water to remove chloride ions. The organic phase containing the free base form of sertraline is then treated as disclosed in the previous paragraph to afford sertraline acetate.

This invention also relates to sertraline L-acetate, which can be prepared according to the following procedure.

The free base of sertraline is dissolved in a suitable organic solvent such as ethyl acetate; an unsaturated hydrocarbon such as hexane or pentane; an aromatic hydrocarbon, such as benzene or toluene; or a cyclic or acyclic ether such as dioxane, tetrahydrofuran, diethyl ether or methoxymethyl ether or a combination thereof or a combination of any of those solvents with water. A suitable organic solvent is any solvent in which the free base of sertraline is freely soluble, in which the L-lactate salt of sertraline is particularly insoluble and which facilitates the formation of the desired crystalline form. Ethyl acetate is preferred due to its ability to dissolve sertraline, its inability to dissolve the sertraline L-lactate and for the quality of the crystals obtained upon granulation therewith. The temperature of the solution is maintained at room temperature or is raised to the boiling point of the solvent being used. It is preferred to raise the temperature to slightly below the boiling point of the solvent being used, generally between 30° C. and 60° C. When ethyl acetate is used, it is preferred to raise the temperature to approximately 40° C. An excess of L-lactic acid is then added to the reaction mixture. It is generally preferable to add one to two equivalents of L-lactic acid for every equivalent of sertraline. Typically, 1.1 equivalents of L-lactic acid is added. When the reaction is compete, sertraline L-lactate generally precipitates. Occasionally, to obtain a better yield of sertraline L-lactate, the reaction mixture is cooled, generally to about room temperature or about 0° C. After precipitation of the salt, it is generally advantageous to continue to stir or granulate the precipitate. When granulating, it is ordinarily preferable to do so at room temperature or slightly above room temperature and no greater than 35° C. The crystals which form are collected by filtration. The crystals of the L-lactate salt of sertraline are washed with ethyl acetate or hexane and are dried at elevated temperature and reduced pressure, generally 30–60° C. for 24 to 48 hours or a period of time sufficient to remove substantially all traces of solvent and any unreacted L-lactic acid.

Alternatively, sertraline L-lactate can be prepared directly from a salt of sertraline, for example, sertraline hydrochloride or sertraline mandelate, without isolation of the free base form of sertraline. Typically, sertraline hydrochloride is used in this preparation. When using this procedure, sertraline hydrochloride is slurried in water and dilute aqueous base is added dropwise or in small portions. The pH of the solution is monitored during the addition of base to prevent the addition of an excessive amount of base. Typically, the pH is maintained between about 6.5 to 9.5. Preferably, the pH is maintained at 8.5. Suitable aqueous bases which can be used in this reaction include sodium hydroxide, sodium carbonate, sodium bicarbonate, potassium carbonate and potassium bicarbonate. Preferably, aqueous sodium hydroxide is used. The free base of sertraline thus formed is partitioned into an immiscible organic solvent such as hexane, ethyl acetate, benzene, toluene or ethers such as diethyl ether, dioxane or methoxymethyl ether. Generally, ethyl acetate is preferred. The immiscible organic phase is separated from the aqueous phase and the organic phase is washed with water to remove chloride ions. The organic phase containing the free base form of sertraline is then treated as disclosed in the previous paragraph to afford sertraline L-lactate.

Sertraline L-lactate may also be prepared directly from sertraline mandelate. When using this procedure, sertraline mandelate, which is prepared by the method described in U.S. Pat. No. 4,536,518, is slurried in a mixture of water and a suitable organic solvent. Suitable organic solvents for this reaction include ethyl acetate; unsaturated hydrocarbons such as hexane or pentane; aromatic hydrocarbons, such as benzene or toluene; and cyclic or acyclic ethers such as dioxane, tetrahydrofuran, diethyl ether and methoxymethyl ether. The slurry is generally cooled to a temperate below room temperature such as 0° C. to 20° C. Typically the reaction mixture is cooled to about 15° C. The free base of sertraline is then generated by the addition of a suitable base. Suitable bases for this reaction include sodium hydroxide, sodium carbonate, sodium bicarbonate, potassium carbonate and potassium bicarbonate. Preferably aqueous sodium hydroxide is used. Enough base is added to the reaction mixture to ensure complete conversion of the sertraline mandelate to sertraline free base. Typically this conversion is complete when the pH of the aqueous layer is at about 9.6. The organic layer, containing sertraline free base, is separated from the aqueous portion and the aqueous portion is generally extracted with additional portions of organic solvent. The organic layers are combined and concentrated. Filtration may occasionally be necessary to clarify the solution. L-lactic acid is added directly to this solution and the reaction mixture is generally stirred for an extended period to granulate the sertraline L-lactate which forms. Typically the stirring is continued for 8 to 48 hours and preferably for about 16 to 24 hours. The sertraline L-lactate is then isolated and purified as disclosed hereinabove.

This invention also relates to crystalline sertraline L-aspartate, which can be prepared according to the flowing procedure.

The free base of sertraline is dissolved in a suitable organic solvent such as ethyl acetate; an unsaturated hydrocarbon such as hexane or pentane; an aromatic hydrocarbon such as benzene or toluene; or a cyclic or acyclic ether such as dioxane, tetrahydrofuran, diethyl ether or methoxymethyl ether or a combination thereof or a combination of any of those solvents with water. A suitable solvent is any solvent or combination of solvents in which the free base of sertraline is freely soluble, in which the L-aspartate salt of sertraline is particularly insoluble and which facilitates the formation of the desired crystalline form. Ethyl acetate in combination with a small amount of water is preferred due to its ability to dissolve sertraline and L-aspartic acid, its inability to dissolve the sertraline L-aspartate and for the quality of the crystals obtained upon granulation therewith. It is preferred to use a solution of ethyl acetate containing two to three percent water. It is especially preferred to use a solution of ethyl acetate containing three percent water. The temperature of the solution is maintained at room temperature or is raised to the boiling point of the solvent being used. It is preferred to maintain the temperature at room temperature. An excess of aspartic acid is then added to the reaction mixture. It is generally preferable to add one to two equivalents of aspartic acid for every equivalent of sertraline. Typically, 1.1 equivalents of aspartic acid is added. When reaction is complete, sertraline L-aspartate generally precipitates. Occasionally, to obtain a better yield of sertraline L-aspartate, the reaction mixture is cooled, generally to about room temperature or about 0° C. After precipitation of the salt, it is generally advantageous to continue to stir or granulate the precipitate. When granulating, it is ordinarily preferable to do so at room temperature or slightly above room temperature and no greater than 35° C. The crystals which form are collected by filtration. The crystals of the L-aspartate salt of sertraline are washed with ethyl acetate saturated with water and are dried at elevated temperature and reduced pressure, generally 30–60° C. for 24 to 48 hours or a period of time sufficient to remove substantially all traces of ethyl acetate, water and any unreacted aspartic acid.

Alternatively, sertraline L-aspartate can be prepared directly from a salt of sertraline, for example, sertraline hydrochloride or sertraline mandelate, without isolation of the free base form of sertraline. Typically, sertraline hydrochloride is used in this preparation. When using this procedure, sertraline hydrochloride is slurried in water and dilute aqueous base is added dropwise or in small portions. The pH of the solution is monitored during the addition of base to prevent the addition of an excessive amount of base. Typically, the pH is maintained between 6.5 to 9.5. Preferably, the pH is maintained at 8.5. Suitable aqueous bases which can be used in this reaction include sodium hydroxide, sodium carbonate, sodium bicarbonate, potassium carbonate and potassium bicarbonate. Preferably, dilute sodium hydroxide is used. The free base of sertraline thus formed is partitioned into an immiscible organic solvent such as hexane, ethyl acetate, benzene, toluene or ethers such as diethyl ether, dioxane or methoxymethyl ether. Generally, two to three percent aqueous ethyl acetate is preferred. The immiscible organic phase is separated from the aqueous phase and the organic phase is washed with water to remove chloride ions. The organic phase containing the free base form of sertraline is then treated as disclosed in the previous paragraph to afford sertraline L-aspartate.

The free base of sertraline is prepared as disclosed in U.S. Pat. No. 4,536,518 or by neutralizing an aqueous solution of a salt of sertraline such as; for, example, sertraline hydroxide or sertraline mandelate with an aqueous base such as sodium hydroxide, sodium carbonate, sodium bicarbonate, potassium carbonate or potassium bicarbonate. The free base of sertraline can be used in solution or can be isolated as a crystalline solid.

Sertraline hydrochloride and sertraline mandelate are prepared by the methods disclosed in U.S. Pat. No. 4,536,518.

The hygroscopicities of sertraline acetate, sertraline L-lactate and sertraline aspartate are measured using a moisture microbalance such as the VTI moisture balance (VTI Moisture Microbalances, MB 300 G and MB 300 W, VTI Corporation, Hialeah, Fla., USA). sertraline acetate, sertraline L-lactate and sertraline acetate are exposed to atmospheres having a range of humidity from 10% to 90% humidity. A temperature of 25° C. is maintained during all hygroscopicity measurements. The moisture adsorption and desorption isotherms of sertraline acetate, sertraline L-lactate and sertraline aspartate in those atmospheres are determined using the VTI moisture microbalance. Sertraline acetate, sertraline L-lactate and sertraline aspartate are not hygroscopic over the range of humidities studied.

The mechanical properties of sertraline acetate and sertraline L-lactate are determined by testing the compression stress, solid fraction, dynamic indentation, reduced elastic modulus, quasistatic indentation, elastic modulus, shear modulus and tensile strength thereof. Table 1 displays the results of the testing of mechanical properties of sertraline acetate.

TABLE 1

Mechanical Properties of Sertraline Acetate

| Property | Test | Sertraline acetate |
| --- | --- | --- |
| Compression Stress, Mpa | Compact Preparation | 36.7 (2.5) |
| Solid Fraction | Compact Preparation | 0.831 |
| Dynamic Indentation Hard., Mpa | Dynamic Indentation | 60.0 (0.4) |
| Reduced Elastic Modulus, GPa | Dynamic Indentation | 5.1 (0.5) |
| Quasistatic Indentation Hard., Mpa | Quasistatic Indentation | 25.1 (1.3) |
| Elastic Modulus, Gpa | Quasistatic Indentation | 2.2 (0.2 |
| Shear Modulus, Mpa | Quasistatic Indentation | 99.9 (19.1) |
| Tensile Strength, Mpa | Tensile Fracture | 0.52 (0.03) |

Table 1a displays the results of the testing of mechanical properties on sertraline L-lactate.

TABLE 1a

Mechanical Properties of Sertraline L-lactate

| Property | Test | Sertraline-L-lactate |
| --- | --- | --- |
| Compression Stress, Mpa | Compact Preparation | 52.8 (0.7) |
| Solid Fraction | Compact Preparation | 0.862 |
| Dynamic Indentation Hard., Mpa | Dynamic Indentation | 81.6 (1.6) |
| Reduced Elastic Modulus, GPa | Dynamic Indentation | 7.4 (0.6) |
| Quasistatic Indentation Hard., Mpa | Quasistatic Indentation | 31.1 (1.4) |
| Elastic Modulus, Gpa | Quasistatic Indentation | 2.0 (0.2) |
| Shear Modulus, Mpa | Quasistatic Indentation | 113.9 (4.6) |
| Tensile Strength, Mpa | Tensile Fracture | 0.56 (0.02) |

Mechanical properties such as tensile strength, elastic modulus and hardness of pharmaceutical compacts (of drug, excipient as well as drug and excipient) cannot be estimated by standard methods used in metallurgy because pharmaceutical solids cannot be compressed into homogeneous fully dense bodies. In general the following four categories of mechanical properties are routinely evaluated: elastic, viscoelastic, plastic and fracture. All four categories contribute towards the three events of a compaction process, i.e., compression, dwell and decompression. The estimation of mechanical properties of pharmaceutical powders is difficult because critical parameters which influence the measurement of mechanical properties such as particle size distribution, crystal habit surface texture, degree of crystallinity and crystallographic symmetry vary considerably in these materials. However, indices of tableting performance (hereinafter termed "ITP") are used for predicting the tableting performance of pharmaceutical compacts (Hiestand, E. N., Smith, D. P. Powder Tech., 38: 146–159, 1984; Hiestand, E. N., Smith, D. P. Adv. Ceram., 9: 47–57, 1984). These indices are derived from critical measurements made to assess the mechanical response of the compacts (measurements are not made during the process of compaction). By measuring and calculating these mechanical properties a person skilled in the art can understand the fundamental properties of the pharmaceutical powder. This understanding allows the skilled person to determine whether a tablet dosage form can be manufactured. Measurement and calculation of the ITP mechanical properties such as tensile strength, indentation modulus and hardness of the compressed compact is accomplished according to procedures described by Hiestand (J. Pharm. Sci., 60: 758–763, 1971; J. Pharm. Sci, 63: 605–612, 1974; J. Pharm. Sci., 74: 768–770, 1985; Pharmaceutical Technology, 8: 54–66, 1989; Int. J. Pharm., 67: 217–229, 1991; Int. J. Pharm., 67: 231–246, 1991).

The measurements of mechanical properties can be routinely accomplished using square compacts of the pure drug substance, in this case sertraline acetate and sertraline L-lactate. The measurements are made in triplicate and the compacts are prepared by uniaxial compression and triaxial decompression.

The most critical material properties that influence powder compaction are its ductility, elasticity and tensile strength. Ductility is determined by pendulum impact and is a dynamic indentation test to determine the hardness of the compact. The hardness of the compound is inversely related to its ductility. Since plastic deformation enhances interparticle bonding, high ductility or low hardness is most desirable. Typically, dynamic indentation hardness values below 100 Mpa are high; values in the 100–200 MPa range are marginal and values greater than 200 MPa are low.

The elastic modulus (also known as Young's modulus) of the compact is determined by measuring the amount of dent recovery after a prolonged (quasielastic) indentation hardness test. It is desirable to have low elastic response of the material during decompression which implies that the material should exhibit low elastic modulus. Elasticity values of greater than 8 GPa are high, values between 1–8 GPa are moderate and values less than 1 GPa are low.

Tensile strength is measured by transverse compression of the compacts until it results in tensile fracture. It is desirable to have high tensile strength. Tensile strength of greater than 2 MPa is high, values in the range of 0.8–2.0 Mpa are moderate and values less than 0.8 MPa are low.

Hiestand's ITP is comprised of the following characteristics: brittle fracture index (herein termed BFI), best case bonding index (herein termed bBI), worst case bonding index (herein termed wBI) and strain index (herein termed SI).

The BFI is a measure of the propensity of a compact to break or fragment under stress from existing cracks and holes in the compact. BFI is used by the skilled person to indicate the propensity of a tablet to break or fragment during processing (i.e. failure) such as during ejection from a tablet press or during film coating. A brittle fracture index value of 0 is excellent, values in the range of 0.01–0.09 are good; values in the range of 0.1–0.19 are marginal and values of 0.2–1.0 are poor.

Bonding index is an estimate of the capacity of a compact to retain interparticulate bonds during elastic recovery. Hiestand has attributed the process of plastic deformation as the principal mechanism for formation of tablet bonds when a pharmaceutical powder is subjected to stress under a load. The estimate of plastic deformation is used in calculating the bonding index. The estimation of bonding index is important since decompression is a major step in the manufacture of tablets. The worst case bonding index (wBI) and best case bonding index (bBI) assess the ability of the interparticulate bonds that have been formed during compression to survive the release of strain energy during compression. Under conditions of high speed manufacture of tablets wBI is more applicable than bBI. Bonding index values of greater than or equal 2 are excellent; values between 0.8–1.9 are good; values between 0.3–0.7 are marginal and values less than 0.3 are poor.

The strain index is a measure of the elastic recovery of the compact. It can also be stated to be a measure of be extent of elastic recovery during the unloading phase. Elastic recovery from an indentation process can be utilized as an estimate of the elastic modulus.

Samples for the test of mechanical properties are prepared according to standard procedures. To generate reliable data, such samples must be free of mechanical flaws, such as microcracks. Therefore, a specialized tablet press, prepared as described in U.S. Pat. No. 4,880,373, is utilized. This press compresses the powder uniaxially (i.e., in one dimension) and then slowly decompresses the powder triaxially (i.e., in three dimensions). The samples are compressed to a given degree of compaction, termed the reference state. This allows the mechanical property data to be compared to other materials which have been compressed to the same reference state. The standard compaction procedure is to compact powders to a solid fraction of 0.85. Solid fraction, or relative density, is the apparent density of the compact divided by the true (absolute) density of the compact. The apparent density of the compact is determined by measuring the volume thereof and dividing by the mass. This measurement is usually made in cubic centimeters per gram. The true density of the powder is determined by helium pycnometry. Ordinarily, to achieve the desired solid fraction, trial compactions of carefully weighed powder samples must be performed and the solid fraction of the resultant compact is measured. Adjustments to solid fraction are achieved by increasing or decreasing the powder weight.

The square compacts which serve as the test specimens are prepared using the triaxial decompression tablet press, prepared as described in U.S. Pat. No. 4,880,373, with a square split die and 1.9 cm square upper and lower punches. The prelubricated die and lower punch are mounted in the tablet press and the die is filled with the preweighed powder. The powder surface is smoothed with a spatula and the upper punch is placed in the die on top of the powder. To ensure a high level of precision, the process is ordinarily computerized. The die hydraulic ram is brought to full extension, pressing the die halves tightly together. Next, the punch ram is brought to full extension, compressing the powder uniaxially. Once the ram reaches full extension, it remains so for a five minute dwell period. During this dwell, the punch and die forces relax due to stress relaxation in the sample. At the end of the dwell, the computer bleeds off the metal-to-metal forces on the punch and die hydraulic cylinders and then begins the triaxial decompression for 15 minutes. During this phase the punch and die forces are simultaneously slowly backed off, keeping the pressures at a 1-to-1 ratio, until reaching the minimum forces attainable by the hydraulic system. The finished compact is then retrieved and the process repeated. Center hole compacts are prepared in the same manner except that the lower punch has a spring-loaded pin installed in it. Usually the center hole passes through about 75% of the compact. A micro drill press, fitted with a bit the same diameter as the punch pin, is used complete the hole. All samples are allowed to relax for an 18 to 24 hour period prior to testing.

The relaxed compacts are used as the test specimens for the mechanical measurements. The following table summarizes the testing techniques, the key measurements, and the properties determined by the tests.

TABLE 2

Mechanical Property Testing Techniques and Measurements

| Technique | Key Measurements | Measured Properties | Derived Properties |
|---|---|---|---|
| Indentation Hardness | Initial Height, $h_i$ 2 Rebound Height, $h_r$ 3 Chordal Radius, a | Dynamic Hardness, $H_0$ | 1 Reduced Elastic Modulus, E' 2 Viscoelastic Constant, VE 3 Worst Case Bonding Index, $BI_W$ 4 Brittle/Viscoelastic Bonding Index, $bBI_V$ |
| Indentation Hardness | 1 Relaxed Force, F 2 Chordal Radius, a | 1 Quasi-Static Hardness, $H_{10}$ 2 Shear Modulus, G | 1 Best Case Bonding Index, $BI_b$ 2 Viscoelastic Constant, VE 3 Elastic Modulus, E |
| Fracture | 1 Force, F 2 Compact Thickness, T | 1 Tensile Strength, $\sigma_T$ | 1 Worst Case Bonding Index, $BI_W$ 2 Best Case Bonding Index, $BI_b$ 3 Brittle Fracture Index, BFI 4 Brittle/Viscoelastic Bonding Index, $bBI_V$ |
| Fracture | 1 Force, F 2 Compact Thickness, T | 1 Compromised Tensile Strength, $\sigma_{T0}$ | 1 Brittle Fracture Index, BFI |
| Powder Flow | 1. Shear Strength, | 1 Effective Angle of Internal Friction, | 1 Uniform Flow Number, UFN |

Dynamic indentation hardness, $H_0$, of the compacts is measured with a pendulum impact apparatus, prepared as described in U.S. Pat. No. 4,885,933. The compact is mounted in pneumatically-powered clamps with a solid backing behind the compact. The spherical pendulum has a known mass and diameter and is poised at a predetermined initial angle before release. The pendulum is released toward the compact, strikes the compact and rebounds. The time required for the pendulum to pass between two photocells of given distance apart is measured and the pendulum rebound height, $h_r$ is automatically calculated. These measurements and calculations are conveniently made by a computer. The dented compact is removed from its clamps and it is mounted on a surface profilometer (Surfanalyzer 5000, Federal Products, Inc., Providence, R.I.). This instrument's probe is carefully positioned and then it scans the dent surface by traversing across it. Three parallel scans are performed on each dent. The first is performed across the dent center, and the second and third equidistant are performed on either side of the first scan. The profile data of all three scans are saved and analyzed by performing circular curve fitting to determine the dent's chordal radius and to calculate $H_0$ according to equation (1), $$H_0 = ((4mgrh_r)/\pi a^4)*((h_i/h_r)-0.375) \qquad (1),$$

where m and r are the indentor's mass and radius, g is the gravitational constant, a is the dent's chordal radius and $h_i$ and $h_r$ are the initial and rebound heights of the indentor.

Quasistatic indentation hardness, $H_{10}$, is determined by slowly pushing a motor-driven spherical indentor, prepared as described in U.S. Pat. No. 4,957,003, into the surface of a compact to a predetermined distance and holding it in that position for a fixed period of time. This is termed the dwell period. The indentor is generally held in position for about five to twenty minutes and preferably for ten minutes. At the end of the dwell period, the force on the indentor is recorded. The compact is removed, its dent scanned and analyzed as described above for the pendulum test and $H_{10}$ is calculated according to equation (2), $$H_{10}=F_r/(\pi a^2) \qquad (2),$$

where $F_r$ is the relaxed force on the indentor after the dwell time and a is the dent's chordal radius. The compact is held in place by pneumatically powered clamps. The indentor diameter is the same as the pendulum's diameter (2.54 cm). The penetration depth of the quasistatic indentor is such that the chordal radius of the dent would match that produced in the impact test.

The tensile strength of regular compacts, $\sigma_T$, is determined by the transverse compression of the compact to fracture between a stationary platen and a motor-driven platen of given width. The force on the platens is monitored continuously and a force-time profile is displayed on the computer screen after the test. The profile is analyzed by identifying the point of fracture which usually exhibits a sharp drop in force. An event marker is also used to help identify the break when the sample visibly cracks. The tensile strength is then calculated according to equation (3), $$\sigma_T=F_{break}/(W_p*T)*PTF \qquad (3)$$

where $W_p$ is the platen width, T is the thickness of the compact and PTF is the perpendicular tensile force which is 0.16 when the platen width is 40% of the compact width. The rate of compression in the test is monitored by calculating a time constant and adjusting the platen speed such that the time constant lies between ten and twenty seconds. With equivalent time constants; material viscoelastic effects are avoided. The time constant is defined as the time in seconds on the force-time profile between $F_{break}$ and $F_{break}/e$, where $F_{break}$ is the force at which the compact fractures and $F_{break}/e$ is an exponent. The time difference between $F_{break}$ and $F_{break}/e$ is defined as the "time constant". This normalization of time constant is incorporated into the calculations to eliminate the contributions from viscoelasticity of the material towards its fracture.

The compromised tensile strength, $\sigma_{TO}$, is measured on center-hole compacts using the same apparatus and motor speed settings as in the regular tensile strength test. It is calculated according to equation (3) above.

Powder flow evaluations are performed using a simplified plate-type shear cell on the non-compacted powders after they have equilibrated at least 18 hours to a given relative humidity (RH), usually 50%, at ambient temperature. Shear cells are prepared as described in Hiestand and Wilcox, J. Pharm. Sci., 1969, 58, 1403–10; Hiestand et al., J. Pharm. Sci., 1973, 62, 1513–1517; and Hiestand and Wells, Proceedings International Powder and Bulk Solids Handling and Processing Conference, Rosemnont, Ill., May 10–12 (1977). A circular bed of powder, 4 to 6 mm thick and 63.5 to 82.5 mm in diameter, is formed on a coarse sandpaper surface using a template. The template is removed and a sled, which is attached to a load cell by a tow line, is placed on the powder. A weight is placed on the sled and the machine's motor is started which pulls the weighted sled across the powder. The pulling force is continuously measured by the load cell. The force rapidly increases to a maximum until the sled begins to move across the powder in a shearing action at which point a force reduction is observed. The motor's direction is then reversed until the tow line goes slack. The motor then pulls again to a maximum force and the motor direction again reversed. The process is repeated several times more until the force maxima is reproducible. The powder bed is then manipulated to its previous shape. The sled, carrying identical weight, is placed back on top of the powder. The above process is repeated until the plateau force is obtained. The powder bed is reformed and the entire process repeated with a different weight on the sled. The effective angle of internal friction is calculated as the arc tangent of the slope of the plot of plateau shear stress versus consolidation stress. This parameter is used to calculate the Uniform Flow Number, UFN, as shown in equation (4), $$UFN=0.667*(42-\delta) \qquad (4),$$

where $\delta$ is the effective angle of internal friction.

Sertraline acetate does not possess any deficiencies that impede the formation and preservation of particle bonds during compression and decompression. Specifically, sertraline acetate was found to have high ductility and relatively low elastic modulus. Overall, sertraline acetate has exceptional mechanical properties and particle bonding ability and thus is an excellent candidate for tablet manufacture.

The values for the intrinsic mechanical properties of the lactate salt indicate that it possesses no weaknesses which would impede particle bond formation and preservation during compression and decompression. The tensile strength of sertraline L-lactate was found to be very high. Further, the compression stress of the lactate salt of sertraline was greater than its hardness. Values for the tabletting indices of the lactate salt of sertraline suggest it is an excellent candidate for tablet manufacture. Overall, sertraline L-lactate has exceptional mechanical properties, particle bonding ability and tabletting index values. Thus, sertraline L-lactate is an excellent candidate for tablet manufacture.

Crystallinity of sertraline acetate, sertraline L-lactate and sertraline L-aspartate are determined by polarized light microscopy and powder X-ray diffraction. The powder X-ray diffraction pattern is determined at ambient temperature using an X-ray diffractometer (Diffraktometer 5000, Siemens Analytical X-ray Systems, Inc., 6300 Enterprise Lane, Madison, Wis. 53719-1173). Typically samples are placed in an aluminum holder and are scanned with the diffraction angle, 2θ, increasing from 5° to 35°, with a step size of 0.02° and a counting time of one second. The thermal characteristics, melting point, heat of fusion and loss in weight during heating were determined using two instruments: Differential Scanning Calorimeter (DSC 4, Perkin Elmer, USA) and Thermogravimetric Analyzer (SSC 5200, Seiko, Japan).

To determine the solubility of sertraline acetate, sertraline L-lactate and sertraline L-aspartate, an aliquot of sertraline acetate, sertraline L-lactate or sertraline L-aspartate is added to a measured amount of water in a screw cap vial. To accelerate the attainment of equilibrium the saturated solution can be prepared at a temperature higher than ambient temperature. The vial is placed on a rotator that is immersed in a water bath at 40° C. At this temperature enough sertraline salt is added until excess solid is present in the vial. The vial is maintained at 40° C. for 6 hours at which time the temperature is lowered to 15° C. for two hours. The temperature of the vial is then adjusted to 25° C. and is maintained at this temperature for up to two days. At the end of the equilibration time, the solution is filtered, the pH of the filtrate is measured and an aliquot of the filtrate is assayed by reverse phase HPLC to determine the concentration of sertraline in solution. The HPLC assay is performed using a Waters Symmetry C-18, 250×4.6 mm column, eluted at 1.0 mL/min. with a mobile phase solution. The column can be purchased from Waters Corp., 34 Maple Street, Milford, Mass. 01757. The mobile phase solution is prepared by mixing 270 mL of tetrahydrofuran, 230 mL of methanol and 400 mL of buffer. The buffer is prepared by adding 1.7 mL of phosphoric acid and 3.5 mL of triethylamine to one liter of water. The excess solid in the vial is collected, dried and then investigated for its crystallinity using microscopy and thermal analysis. The instant acetate salt of this invention has a water solubility of 84 mg/ml. The instant L-lactate salt of sertraline of this invention has a water solubility of 125 mg/mL. The instant L-aspartate salt of sertraline of this invention has a water solubility of 28.6 mgA/mL. This high degree of water solubility permits more sertraline to be delivered over a shorter period of time, which is particularly useful for acute indications. Furthermore, a high solubility is advantageous in osmotic oral controlled release dosage forms which deliver a solution of sertraline in a controlled fashion.

The chemical stabilities of sertraline acetate, sertraline L-lactate and sertraline L-aspartate are determined using reverse phase high performance liquid chromatography (reverse phase HPLC, same conditions as above) assay of samples that have been subjected to accelerated stability challenge. In an accelerated stability challenge, samples of sertraline acetate are subjected to varying combinations of humidity and temperature conditions for varying lengths of time. The following combinations of humidity and temperature are particularly useful in evaluating the chemical stability of sertraline and various salt forms thereof. The activity of sertraline acetate as well as the presence of impurities and decomposition products is quantitated in these investigations. Generally a drug is considered stable if the amount of new impurities detected is less than 0.1% of the amount of the drug used. The stability of sertraline acetate, sertraline L-lactate and sertraline L-aspartate in the solid state as well as in solution was determined.

Accelerated stability testing is conducted by subjecting sertraline acetate, sertraline L-lactate or sertraline L-aspartate to standard test conditions of temperature and humidity as defined by the ICH (International Conference on Harmonization of Technical Requirements for the Registration of Pharmaceuticals for Human Use) Guidelines. Generally, a sample of sertraline acetate, sertraline L-lactate or sertraline L-aspartate is evaluated at 40° C.±2° C./75% RH±5% for a period of 24 weeks. In addition samples are placed under the following conditions: 50° C.±2° C./20% RH for 24 weeks; 70° C.±2° C./RH≦10% for 3 weeks. Stability of sertraline acetate, sertraline L-lactate or sertraline L-aspartate is also evaluated by placing it in 0.01 N hydrochloric acid solution for 6 weeks at 50° C. and in 0.01 N sodium hydroxide solution for 6 weeks at 50° C. All of the samples subjected to stability testing are evaluated for purity and decomposition by performing a reverse phase HPLC analysis, using the same conditions as described above. When the above experiments are performed on sertraline acetate, sertraline L-lactate or sertraline L-aspartate, no new decomposition products were observed at levels greater than 0.1% of the parent compound. The purity of each of the sertraline acetate, sertraline L-lactate and sertraline L-aspartate samples was greater than 99%.

In the treatment of the diseases and conditions disclosed herein and claimed in the appendant claims, sertraline acetate, sertraline L-lactate or sertraline L-aspartate may be formulated as immediate release dosage forms as disclosed, for example, in U.S. Pat. No. 4,536,518. Alternatively, sertraline acetate, sertraline L-lactate or sertraline L-aspartate may be formulated in a controlled release dosage form, such as a sustained release dosage form, an encapsulate solution dosage form or a delayed release dosage form. The manner of making and using such sustained release, encapsulated solution and delayed release dosage formulations is disclosed in commonly-assigned copending U.S. applications entitled "Encapsulated Solution Dosage Forms of Sertraline", and "Delayed Release Dosage Forms of Sertraline", respectively, and having Pfizer docket numbers PC9838JTJ and PC9824JTJ, respectively, each of which are PCT applications designating the United States and each of which is incorporated herein by reference.

In general, sertraline acetate, sertraline L-lactate and sertraline L-aspartate are normally administered in dosages ranging from about 0.2 mgA/kg of body weight per day to about 10 mgA/kg of body weight per day, although variations will necessarily occur depending upon the conditions of the subject being treated and the particular route of administration chosen. Typically, a preferred range of dosages is about 15 mgA of sertraline acetate, sertraline L-lactate or sertraline L-aspartate per day to about 200 mgA of sertraline acetate, sertraline L-lactate or sertraline L-aspartate per day for average adult subjects having a body weight of about 70 kg. However, the preferred dosage amount will depend upon the dosage form in which sertraline acetate, sertraline L-lactate or sertraline L-aspartate is administered as well as other factors which will be readily apparent to a person skilled in the art, such as a physician.

Where used herein, the abbreviation "Mpa" means megaPascals and the abbreviation "Gpa" means gigaPascals.

Where used herein, the term "osmotic tablets" defines a controlled release solid dosage form powered by osmotic pressure.

For convenience and consistency, reference to "sertraline" in terms of therapeutic amounts or in release rates in the claims is to active sertraline, abbreviated herein as "mgA", i.e., the non-salt, non-hydrated free base having a molecular weight of 306.2 g/mole. Amounts in mgA can conveniently be converted to equivalent weights for sertraline acetate, which has a molecular weight of 368.3 g/mole. The molecular weight of the ¼-hydrate form of sertraline acetate is 370.8 g/mole. The molecular weight of sertraline L-lactate is 396.3 g/mole. The molecular weight of sertraline L-aspartate is 439.3 g/mole.

The invention will now be illustrated by the following examples which are not to be taken as limiting. In general, the examples demonstrate the incidence of gastrointestinal side-effects upon oral and IV dosing of sertraline, the amelioration of these side effects by controlled release dosing, and the preparation of sustained-release dosage forms of sertraline within the scope of this invention, salts, processes for making same, and so forth.

In the examples that follow, the following definitions and tests have been employed:

1. "Q" is used to designate a quantity of sertraline either in mgA or in percent (%), as indicated. The Q is associated with a time or "pull point" at which an indicated aliquot of solution was removed for assay of sertraline, the time of removal or pull point being designated in hours as a subscript. Thus, a "$Q_1$" of 15% means that 15% of the sertraline dose was dissolved in 1 hour.

2. Specification of a quantity in percent (%) means percent by weight based on total weight, unless otherwise indicated.

3. "$t_{80\%}$" means the time, in hours, for 80% of sertraline dose to be released from the dosage form.

4. Release rate is defined by the following equation:

release rate=$0.8*(dose)/t_{80\%}$ or $Q_{24}/24$ if 80% of the sertraline is not released within 24 hours 5. "Surelease®" is the registered trademark of Colorcon Inc., West Point, Pa. for an aqueous, fully plasticized polymeric dispersion of ethylcellulose.

6. "Opadry®" is the registered trademark of Colorcon Inc., West Point, Pa. for a family of plasticized cellulose ethers which include hydroxypropyl methylcellulose, hydroxypropyl cellulose and methylcellulose that are supplied as powders for reconstitution in water.

7. "mgA" is an abbreviation for "milligrams of active sertraline". For example, "200 mgA" means 200 mg of active sertraline.

8. "X mgA of multiparticulate" (where X is a number) means the amount of multiparticulates containing X mgA. For example, "100 mgA of multiparticulates" means the weight of multiparticulates containing 100 mg active sertraline.

9. In Vitro Dissolution Test: The following in vitro test can be used to screen sustained release embodiments of this invention for in vivo suitability. If a particular dosage form satisfies the in vitro criteria or the in vivo criteria disclosed herein, it is within the scope of this invention.

Sustained release dosage forms of sertraline are tested in a standard USP rotating paddle apparatus as disclosed in United States Pharmacopoeia XXIII (USP) Dissolution Test Chapter 711, Apparatus 2. Paddles are rotated at 50 rpm (or 100 rpm if the dosage form is multiparticulate or disintegrates quickly into multiparticulates) and the dissolution is conducted in, as the test medium, 900 mL acetate buffer (0.13M acetic acid) with 0.075M sodium chloride using potassium hydroxide to adjust pH to 4.0, at 37° C. The dissolution vessels are covered to prevent evaporation. If gelatin capsules are used, then 0.1 mg/mL of the enzyme trypsin must be added to the buffer. At indicated times following test initiation (i.e. insertion of the dosage form into the apparatus), filtered aliquots (typically 2 or 10 mL) from the test medium are withdrawn and analyzed for sertraline by reverse-phase high performance liquid chromatography (HPLC) or other suitable quantifiable analysis method. Dissolution results are reported as mgA sertraline dissolved versus time or percent of active sertraline dissolved versus time. Sustained release dosage forms that meet the following criteria are within the scope of the invention: during the initial time over which 80% of drug loading is released (1) the sertraline release rate is between 1 mgA/hr and 40 mgA/hr, as defined above; and (2) the sertraline release rate cannot exceed 40 mgA/hr during any one hour period; and, (3) less than 70% of the incorporated sertraline is released during the first hour in the use environment.

For a delayed plus sustained release embodiment wherein the delay is temporal, the same test as described immediately above for pure sustained release embodiments is employed without any modification. The dosage form will release sertraline at a rate less than 1 mgA/hr for a period of up to three hours or less, corresponding to the delay period, followed by sustained sertraline release at a rate of from 1 mgA/hr to 40 mgA/hr thereafter.

A convenient test for a spatially delayed plus sustained release embodiment of the current invention is a modified version of a two part in vitro dissolution test, which is described in the 1995 US. Pharmacopoeia (USP 23), Section [724], Subsection "Delayed Release (Enteric-coated) Articles—General Drug Release Standard", which incorporates a 2 hr test of sertraline release in a simulated gastric fluid ("acid test"), followed by a test of drug release in a simulated intestinal fluid ("neutral test"). For tablets and capsules which do not contain multiparticulates or disintegrate rapidly into multiparticulates, stirring is effected using paddles at 50 rpm. For multiparticulates or dosage forms that disintegrate into multiparticulates, stirring is effecting using paddles at 100 rpm. If gelatin capsules are used, then 0.1 mg/mL of the enzyme trypsin must be added to the buffer. This two stage in vitro test is adjusted to be useful in evaluating spatially delayed plus sustained embodiments of this invention, as now described.

For pH-triggered spatially-delayed plus sustained release embodiments, the in vitro test is carried out as described in the USP "Enteric Test", with the requirements that dosage forms of the invention (a) release sertraline at a rate not exceeding 1 mgA/hr for at least one hour during the "acid" phase of the test (in 0.1 N HCl), and (b) release sertraline at a rate between 1 mgA/hr and 40 mgA/hr in the neutral phase of the test, provided that the dosage forms release no more than an additional 70% of the incorporated sertraline in the first hour of the neutral phase of the test. If desired, the acid phase portion of the test can be carried out for longer than 1 hour, i.e., under even more stringent conditions and such embodiments are also within the scope of the invention. Calculation of the sertraline release rate during the neutral phase of the test is as follows. The rate is calculated by noting the time following the 1 hour delay during which an additional 80% of the dose has been released into the neutral (pH 6.8) medium, then carrying out a division in which the numerator is 80% of the dose in mgA, and the denominator is the time at which an additional 80% of the dose is released into the neutral medium minus 1 hour (or other time period if the acid phase is longer than 1 hour). The acid portion of the test is carried out in 750 ml 0.1N HCl, for 1 hr. After 1 hr, 250 ml 0.2M tribasic sodium phosphate, containing 10 gm polysorbate-80, is added to the acid medium (containing the dosage form), and the pH is adjusted to pH 6.8, using either 2M hydrochloric acid or 2M sodium hydroxide. The solubility of sertraline is low in phosphate buffer (pH 6.8). Thus polysorbate-80 (1% w/v) is added to the neutral (pH 6.8) phosphate medium to increase the sertraline solubility to provide "sink conditions" for dissolution.

For enzyme-triggered spatially-delayed plus sustained release embodiments described in this disclosure, release of sertraline is "triggered" by the presence of pancreatic lipase, esterase, or protease in the small intestine. For in vitro evaluation of lipase-triggered delayed plus sustained release dosage forms, 5 mg/ml porcine pancreatic lipase (Sigma Chem., St. Louis, Mo.) is included in the dissolution medium for the second neutral stage of the dissolution test. For esterase- or protease-triggered delayed release systems, appropriate esterases or proteases (e.g. pancreatic esterase, trypsin, chymotrypsin, elastase) are included in the second stage of the in vitro test. Thus the test is conducted in the same manner as for pH-triggered spatially delayed forms, but the neutral phase is conducted in the presence of an enzyme suitable for triggering the onset of sustained release. If the esterase, protease, or lipase is denatured by polysorbate-80, then the first hour of the "neutral" phase is carried out in the presence of enzyme and absence of polysorbate-80. After one hour in the "neutral" phase, 10 g of polysorbate-80 is added.

EXAMPLE 1

This example demonstrates that sustained release dosing of sertraline (200 mg dose as sixteen 12.5 mg doses given at time zero and every hour for 15 hr) results in decreased side effect severity, relative to a single 200 mg bolus dose.

In a double-blind, randomized, placebo-controlled parallel group study, healthy male human subjects were divided into three groups. Group A, referred to as the "bolus dosing group", received a single 200 mg sertraline dose as two 100 mg sertraline immediate release tablets (ZOLOFT®). The tablets were administered with 50 ml water. The bolus dosing group also received a 50 ml placebo solution every hour for 15 hours. The placebo solution contained lactose, menthol, and polyvinylpyrrolidone to mimic the appearance and mouth feel of the sertraline solution, to assure blinding. Group B, referred to as the "divided dosing group", received the same total dose, administered as a solution of 125 mg sertraline solution in 50 ml of water at the rate of one 125 mg dose each hour for 15 hours. Group B also received two placebo tablets at the fist dosing time. Group C, referred to as the "placebo group", received placebo tablets and placebo solutions at the appropriate corresponding time points. All subjects were dosed after an overnight fast.

Blood samples were withdrawn prior to dosing, and at 0.5, 1, 2, 3, 4, 5, 6, 7, 8, 9, 10, 11, 12, 13, 14, 15, 16, 18, 20, 22, 24, 36, 48, 72, 96, 120, 144, 168, 192, and 240 hr post-dosing. Plasma sertraline concentrations were determined using capillary gas chromatography. Total systemic exposure to sertraline was determined by measuring the area under the plasma sertraline concentration vs. time curve (AUC) for each subject in a given group, and then by calculating a mean AUC for the group. $C_{max}$ is the maximum observed plasma sertraline concentration achieved in a subject. $T_{max}$ is the time at which $C_{max}$ is achieved. Plasma pharmacokinetic data for this example are presented in Table 1-1.

Prior to dosing and to each blood sampling time, each subject filled out a questionnaire, which consisted of a series of "Visual Analogue Scales" in which the subject was required to rate, on a scale of 0–10, the severity of certain potential side effects. The subjects were instructed that "0" indicated an absent effect and "10" indicated the worst possible effect.

A total of 45 subjects completed this study: 15 each in Groups A, B, and C. For eight side effects evaluated at 30 time points, a total of 10,800 individual visual-analogue-scale evaluations were obtained.

Table 1-1 demonstrates that the total systemic sertraline exposure of the two dosing groups, Groups A and B, as reflected in the AUC, was similar. For the divided dosing group, $C_{max}$ was lower and $T_{max}$ was longer, as expected, because the dosing took place over 15 hr, rather than a single bolus dose. Three subjects in the 200 mg bolus dose group had emesis at 4.25, 11.2, and 7.6 hr. Since the emesis occurred after substantial plasma concentrations were achieved in all three subjects and after $T_{max}$ in two, the data from these subjects were not treated differently than the data from other subjects. Subjects on the 15 hr divided dose regimen experienced no emetic episodes. Thus the 15 hr divided dose regimen exhibited a decreased incidence of emesis, relative to the bolus dose regimen.

Analysis of side effect visual-analogue-scale data was carried out as follows. For a particular side effect (e.g., abdominal pain) in a particular subject, visual-analogue-scale scores over the 24 hr post-dose period were summed to give a "cumulative score". "Cumulative scores" for all members of a treatment group were summed, and divided by the number of subjects in the group, to give a Mean Cumulative Score. The scale of this Mean Cumulative Score does not correspond to the original 0–10 scale, since it reflects the summation of all non-zero scores over the entire evaluation period. Table 1-2 presence Mean Cumulative Scores for a series of gastrointestinal side effects: abdominal pain, nausea, urgency to defecate, regurgitation, diarrhea, and abdominal cramping. The non-gastrointestinal side effects dizziness and tremor were also evaluated.

Table 1-2 demonstrates that the overall severity of sertraline-induced side effects was lower for the 15 hr divided dose treatment.

TABLE 1-1

Sertraline Pharmacokinetics For a 200 mg Dose given as a Single Dose, or as Sixteen 12.5 mg doses every Hour for 15 Hours (mean values).

| TREATMENT | $C_{max}$ (ng/ml) | $T_{max}$ (hr) | $AUC_{O\text{-}last}$ (ng.hr/ml) |
|---|---|---|---|
| 200 mg single dose (Group A) | 74 | 6 | 1646 |
| 12.5 mg per hr for 15 hr (Group B) | 32 | 16 | 1227 |

TABLE 1-2

Mean Cumulative Visual Analog Score Data for Various Side Effects, averaged over all 15 subjects in each group. See text for explanation of "mean cumulative score."

MEAN CUMULATIVE SCORE

| SIDE EFFECT | GROUP A (Bolus Dose) | GROUP B (16 Divided Doses) | GROUP C (Placebo) |
|---|---|---|---|
| Abdominal Pain | 2.7 | 0.1 | 1.7 |
| Nausea | 17.5 | 2.6 | 1.2 |
| Urgency to Defecate | 3.1 | 0.5 | 0.6 |
| Regurgitation | 4.0 | 0.3 | 0.3 |
| Abdominal Cramping | 3.1 | 0.1 | 0.9 |
| Diarrhea | 3.9 | 0.2 | 0.2 |
| Dizziness | 13.8 | 0.5 | 6.8 |
| Tremor | 7.9 | 1.7 | 0.5 |

Example 1 further demonstrates that (1) side effects may be ameliorated by controlling the rate at which sertraline is released into the gastrointestinal tract, (2) delivery at a rate of 200 mg/15 hr=13.3 mg/hr results in a decrease in gastrointestinal and systematic side effects compared to bolus dosing with the divided-dose side effect severity at or near placebo levels (Table 1-2), and (3) sustained release dosage forms which contain less than 200 mg sertraline also have an advantageous side effect profile. In the course of carrying out the first half of the 200 mg/15 hr divided dose study of this example, eight 12.5 mg doses were delivered over 7 hr, with low observed side effect intensity (total dose 100 mg). Likewise, during the first quarter of the 200 mg/15 hr divided dose study of this Example, four 12.5 mg doses were delivered over 3 hr, with low observed side effect intensity (total dose 50 mg).

From another perspective, side effects (particularly tremor and dizziness, which are systemically mediated, and not mediated by direct contact of sertraline with the gastrointestinal tract) may be ameliorated by controlling the maximum sertraline concentration in the systemic circulation after oral dosing. In this Example, the 16×12.5 mg divided dose gave a $C_{max}$ of 32 ng/ml, with very low side effect severity. On the other hand, the 200 mg bolus dose gave a $C_{max}$ of 74 ng/ml, and exhibited significant side effects.

EXAMPLE 2

This example demonstrates that sustained release dosing of sertraline (200 mg dose as eight 25 mg doses given at time zero and every hour for 7 hr) results in decreased side effect severity, relative to a single 200 mg bolus dose.

In a double-blind, randomized, placebo controlled parallel group study, healthy male human subjects were divided into three groups. Group A (n=14) received a single 200 mg sertraline dose as two 100 mg sertraline immediate release tablets (ZOLOFT®) ("bolus dosing" group). The tablets were administered with 50 ml water. Group A also received a 50 ml placebo solution every hr for 7 hr. The placebo solution contained lactose and menthol. Group B (n=16) received the same total dose, administered as a 25 mg sertraline solution (in 50 ml) at the rate of one 25 mg dose each hr for 7 hr ("divided dosing" group). Group B also received two placebo tablets at the fist dosing time. Group C (n=15) received placebo tablets and placebo solutions at the appropriate time points. All subjects were dosed after an overnight fast.

Blood samples were withdrawn prior to dosing, and at 0.5, 1, 2, 3, 4, 5, 6, 7, 8, 9, 11, 13, 15, 17, 24, 48, 72, 96, 120, and 144 hr post dosing. Plasma sertraline concentrations, $C_{max}$, $T_{max}$, and AUC were also determined in the same manner. Plasma pharmacokinetic data for this example are presented in Table 2-1.

Prior to dosing and each blood sampling time, each subject filled out a questionnaire, which consisted of a series of "Visual Analogue Scales" as described in Example 1. A total of 45 subjects completed this study. For three side effects evaluated at 30 time points, a total of 4,500 individual visual-analogue-scale evaluations were obtained.

Table 2-1 demonstrates that the total systemic sertraline exposure of the two dosing groups, reflected in the AUC, was similar. For the divided dosing group, $C_{max}$ was lower and $T_{max}$ was longer, as expected because the dosing took place over 7 hr rather than in a single bolus dose. Four subjects in the 200 mg bolus dose group had emesis at 2.6, 2.8, 2.8, and 3.8 hr. The pharmacokinetic data from these four subjects were not included in the averages presented in Table 2-1. One subject on the 7 hr divided dose regimen had emesis at 12.6 hr. Since this occurred 3.5 hr after $T_{max}$ for this individual, his data were included in the average analysis for the divided dosing group. The observation of 4 and 1 emetic events for the bolus dose and divided dose groups, respectively, indicates that 7 hr divided dosing gave a lower incidence of emesis, while providing a therapeutic sertraline dose as evidenced by pharmacokinetic AUC.

Analysis of side effect visual-analogue-scale data was carried out as described in Example 1. Table 2-2 demonstrates that the overall severity of sertraline-induced side effects was lower for the 8 divided dose treatments.

Thus side effects may be ameliorated by controlling the rate at which the sertraline is released into the gastrointestinal tract. Example 2 thus demonstrates that delivery at a rate of 200 mg/7 hr=28.6 mg/hr (or slower) results in a decrease in side effect severity (Table 2-2).

Example 2 also demonstrates that sustained release dosage forms which contain less than 200 mg sertraline have an advantageous side effect profile. In the course of carrying out the first half of the example, four 25 mg doses were delivered over 3 hr. with low observed side effect intensity (total dose 100 mg).

As for Example 1, this example also demonstrates that side effects, particularly tremor and dizziness, may be ameliorated by controlling the maximum sertraline concentration in the systemic circulation after oral dosing. In this Example, the 8×25 mg divided dose regimen gave a $C_{max}$ of 46 ng/ml, while the 200 mg bolus dose gave a $C_{max}$ of 75 ng/ml. The 8×25 mg divided dose regimen exhibited lower side-effect severity than the bolus dose regimen.

TABLE 2-1

Sertraline Pharmacokinetics For A 200 mg Dose given as a Single Dose, or as Eight 25 mg doses every Hour for 7 Hours (mean values).

| TREATMENT | $C_{max}$ (ng/ml) | $T_{max}$ (hr) | $AUC_{O-last}$ (ng.hr/ml) |
|---|---|---|---|
| 200 mg single dose | 75 | 5.4 | 1744 |
| 25 mg per hr for 7 hr | 46 | 10.4 | 1439 |

TABLE 2-2

Mean Cumulative Visual Analog Score Data for Various Side Effects, averaged over all 15 subjects in each group. See test for explanation of "mean cumulative score".

MEAN CUMULATIVE SCORE

| SIDE EFFECT | GROUP A (Bolus Dose) | GROUP B (8 Divided Doses) | GROUP C (Placebo) |
|---|---|---|---|
| Regurgitation | 3.9 | 0.1 | 0.1 |
| Dizziness | 10.4 | 4.8 | 2.1 |
| Tremor | 8.9 | 2.7 | 0.3 |

EXAMPLE 3

This example demonstrates that the absorption of sertraline differs when sertraline is dosed directly to various portions of the gastrointestinal tract. Dosage forms which deliver most of their sertraline load before reaching the transverse or descending colon give higher systemic sertraline exposure than dosage forms which deliver a significant portion of their sertraline load in the transverse or descending colon.

Two groups of 6 volunteers (Groups A and B) each were dosed with 200 mg sertraline or placebo by different four-way crossover regimens. Dosing was via (1) oral tablets, or (2) infusion of a solution through a nasoenteric tube into the stomach, duodenum, or ileocecal region of the small intestine, or (3) infusion into the transverse colon via anal intubation.

On four different occasions, Group A received (1) oral sertraline immediate release tablets plus placebo solution infused into the stomach, or (2) oral placebo tablets plus sertraline solution infused into the stomach, or (3) oral placebo tablets plus sertraline infused into the small intestine at the ileocecal junction, or (4) oral placebo tablets plus placebo solution infused into the small intestine at the ileocecal junction. On four different occasions, Group B received (1) oral sertraline immediate release tablets plus placebo solution infused into the duodenum, or (2) oral placebo tablets plus sertraline solution infused into the duodenum, or (3) oral placebo tablets plus sertraline infused into the transverse colon, or (4) oral placebo tablets plus placebo solution infused into the transverse colon.

The oral sertraline dose was administered as two 100 mg tablets. The infusions were administered as a 2 mg/ml solution at a rate of 20 ml/min for 5 min.

Blood samples were withdrawn prior to dosing, and at 0.5, 1, 1.5, 2, 4, 6, 8, 10, 12, 16, 24, 36, 48, 72, 96, 120, 144, 192 and 240 hr post-dosing. Plasma sertraline concentrations, $C_{max}$, $T_{max}$, and AUC were also determined as in Example 1. Plasma pharmacokinetic data for this example are presented in Table 3-1.

Table 3-1 presents the observed average $C_{max}$, $T_{max}$, and AUC for the various dosing regimens. Infusion into the stomach and duodenal regions gave an AUC (total systemic exposure) which was 79% and 110% of the AUC observed after dosing with oral tablets. Thus absorption from these regions of the gastrointestinal tract (in addition to more distal regions since the dosed material moved distally with time) was similar to that from oral tablets. Infusion into the ileocecal region of the small intestine resulted in an AUC which was 62% of that observed after dosing oral tablets. Thus the ileocecal region (in addition to more distal regions) has limited capacity for absorption of sertraline. Infusion into the transverse colon resulted in an AUC which was 16% of that observed after dosing oral tables. Thus the transverse (and more distal descending) colon has a more limited capacity for absorption of sertraline.

TABLE 3-1

Pharmacokinetics of 200 mg sertraline delivered to various portions of the gastrointestinal tract.

| Dosing Route | $C_{MAX}$ (ng/ml) | $T_{MAX}$ (hr) | $AUC_{O\text{-}LAST}$ (ng · hr/ml) |
|---|---|---|---|
| GROUP A | | | |
| Oral Tablet | 39.9 | 7.0 | 1174.5 |
| Stomach Infusion | 35.6 | 7.0 | 923.1 |
| Ileocecal Infusion | 27.3 | 5.0 | 727.1 |
| GROUP B | | | |
| Oral Tablet | 44.7 | 6.7 | 1153.4 |
| Duodenal Infusion | 48.8 | 3.7 | 1270.3 |
| Colonic Infusion | 10.9 | 4.4 | 179.4 |

EXAMPLE 4

This example illustrates making sustained release sertraline hydrophilic matrix tablets which release sertraline at different rates depending on their composition, size and shape. The processing comprised (1) blending all components, as designated in Tables 4-1, 4-2 and 4-3, except for magnesium stearate; (2) screening and reblending the same components; (3) adding and blending magnesium stearate; and (4) compressing the final blend into tablets.

In batch sizes of 200–350 grams, sertraline hydrochloride was blended in a suitable jar with all other components except magnesium stearate for 15 minutes using a Turbula shaker system (Basel, Switzerland). Next, the blend was passed through a 20 mesh screen and shaken again for 15 minutes. Then, magnesium stearate was added and the blend was shaken for 2 minutes. Using a conventional tabletting press (Manesty F-Press, Manesty Machines, Liverpool, England), the final blend was compressed into tablets using either ¼ inch by ¾ inch capsular tooling punches for Examples 4A–4M, 13/32 inch standard round concave (SRC) punches for Examples 4N and 4O, ¼ inch by ½ inch capsular tooling punches for Examples 4P–4X, or ¼ inch by 9/16 inch capsular tooling punches for Examples 4Y–4AD. A summary of the compositions manufactured by direct compression of the formulation blend at 200 mgA sertraline per tablet is shown in Table 4-1 for Examples 4A through 4O, at 100 mg sertraline per tablet is shown in Table 4-2 for Examples 4P through 4X, and at 50 mgA sertraline per tablet is shown in Table 4-3 for Examples 4Y through 4AD respectively.

TABLE 4-1

Sustained Release Hydrophilic Matrix Tablet Compositions Manufactured by Direct Compression on the F-Press with Dosage Strength of 200 mg A/tablet.

| Example | % Sertraline Compound* | % HPMC K100LV[1] | % HPMC K4M[2] | % Lactose | % DCP[3] | % MgSt[4] | Tablet Weight (mg) |
|---|---|---|---|---|---|---|---|
| 4A | 29.8 | 24.9 | 5.0 | — | 39.3 | 1.0 | 750 |
| 4B | 29.8 | 34.9 | 5.0 | — | 29.3 | 1.0 | 750 |
| 4C | 29.8 | 41.6 | 8.2 | — | 19.4 | 1.0 | 750 |
| 4D | 39.8 | 24.9 | 5.0 | — | 29.3 | 1.0 | 562 |
| 4E | 29.8 | 24.9 | 5.0 | 39.3 | — | 1.0 | 750 |
| 4F | 29.8 | 34.9 | 5.0 | 29.3 | — | 1.0 | 750 |
| 4G | 29.8 | 41.6 | 8.2 | 19.4 | — | 1.0 | 750 |
| 4H | 39.8 | 24.9 | 5.0 | 29.3 | — | 1.0 | 562 |
| 4I | 30.0 | 20.0 | 10.0 | 38.0 | — | 2.0 | 750 |
| 4J | 30.0 | 15.0 | 15.0 | 38.0 | — | 2.0 | 750 |
| 4K | 30.0 | 50.0 | 10.0 | 8.0 | — | 2.0 | 750 |
| 4L | 30.0 | 33.3 | 16.7 | 18.0 | — | 2.0 | 750 |
| 4M | 30.0 | 25.0 | 25.0 | 18.0 | — | 2.0 | 750 |
| 4N | 39.8 | 24.9 | 5.0 | — | 29.3 | 1.0 | 562 |
| 4O | 39.8 | 24.9 | 5.0 | 29.3 | — | 1.0 | 562 |

[1]HPMC means hydroxypropyl methylcellulose, Methocel K100LV (Dow Chemical, Midland, MI)
[2]HPMC means hydroxypropyl methylcellulose, Methocel K4M (Dow Chemical, Midland, MI)
[3]DCP means dibasic calcium phosphate dihydrate, Emcompress (Edward Mendell Co., Surrey, UK)
[4]MgSt means magnesium stearate
*% sertraline compound reflects quantity of sertraline salt needed to achieve 200 mg A.

TABLE 4-2

Sustained Release Hydrophilic Matrix Tablet Compositions
Manufactured by Direct Compression on the F-Press with
Dosage Strength of 100 mg A/tablet.

| Example | % Sertraline Compound* | % HPMC K100LV[1] | % HPMC K4M[2] | % Lactose | % MgSt[3] | Tablet Weight (mg) |
|---|---|---|---|---|---|---|
| 4P | 30.0 | 20.0 | 10.0 | 38.0 | 2.0 | 375 |
| 4Q | 15.0 | 24.4 | 12.2 | 46.4 | 2.0 | 750 |
| 4R | 30.0 | 15.0 | 15.0 | 38.0 | 2.0 | 375 |
| 4S | 15.0 | 18.3 | 18.3 | 46.4 | 2.0 | 750 |
| 4T | 30.0 | 33.3 | 16.7 | 18.0 | 2.0 | 375 |
| 4U | 15.0 | 40.6 | 20.4 | 22.0 | 2.0 | 750 |
| 4V | 30.0 | 26.6 | 13.4 | 28.0 | 2.0 | 375 |
| 4W | 15.0 | 32.5 | 16.3 | 34.2 | 2.0 | 750 |
| 4X | 15.0 | 30.5 | 6.1 | 46.4 | 2.0 | 750 |

[1]HPMC means hydroxypropyl methylcellulose, Methocel K100LV (Dow Chemical, Midland, MI)
[2]HPMC means hydroxypropyl methylcellulose, Methocel K4M (Dow Chemical, Midland, MI)
[3]MgSt means magnesium stearate
*% sertraline compound reflects quantity of sertraline salt needed to achieve 200 mg A.

TABLE 4-3

Sustained Release Hydrophilic Matrix Tablet Compositions
Manufactured by Direct Compression on the F-Press with
Dosage Strength of 50 mg A/tablet.

| Example | % Sertraline Compound* | % HPMC K100LV[1] | % HPMC K4M[2] | % Lactose | % MgSt[3] | Tablet Weight (mg) |
|---|---|---|---|---|---|---|
| 4Y | 30.0 | 20.0 | 10.0 | 38.0 | 2.0 | 187.5 |
| 4Z | 15.0 | 24.4 | 12.2 | 46.4 | 2.0 | 375 |
| 4AA | 15.0 | 18.3 | 18.3 | 46.4 | 2.0 | 375 |
| 4AB | 15.0 | 40.6 | 20.4 | 22.0 | 2.0 | 375 |
| 4AC | 15.0 | 32.5 | 16.3 | 34.2 | 2.0 | 375 |
| 4AD | 15.0 | 30.5 | 6.1 | 46.4 | 2.0 | 375 |

[1]HPMC means hydroxypropyl methylcellulose, Methocel K100LV (Dow Chemical, Midland, MI)
[2]HPMC means hydroxypropyl methylcellulose, Methocel K4M (Dow Chemical, Midland, MI)
[3]MgSt means magnesium stearate
*% sertraline compound reflects quantity of sertraline salt needed to achieve 200 mg A.

EXAMPLE 5

Selected sustained release matrix tablets from Example 4, as shown in Table 5-1, were tested using the in vitro sustained release dissolution test procedure with quantification by reverse-phase high performance liquid chromatography (HPLC) analysis for sertraline to determine sertraline released as a percentage of the total dose, as described below.

Sustained release dosage forms of sertraline were tested in a standard USP rotting paddle apparatus as disclosed in United States Pharmacopeia XXIII (USP) Dissolution Test Chapter 711, Apparatus 2. Paddle rotation was set at 50 rpm and the dissolution was conducted in, as the test medium, 900 mL acetate buffer (0.13M acetic acid) with 0.075M sodium chloride using potassium hydroxide to adjust pH to 4.0, at 37° C. The dissolution vessels were covered to prevent evaporation. At indicated times following test initiation (i.e. insertion of the dosage form into the apparatus vessel), filtered aliquots (typically 2 or 10 mL) from the test medium were withdrawn and analyzed for sertraline by reverse-phase HPLC as disclosed below.

Sertraline quantification was conducted by reverse-phase high performance liquid chromatography as follows. A fixed volume of 20 μL was injected onto the analytical column (150 mm length×3.9 mm diameter NovaPac C-18 column). The isocratic mobile phase consisted of an aqueous acetate buffer, methanol and acetonitrile in volume percentages of 40/15/45. The aqueous acetate buffer was prepared by the following: (1) 2.86 mL of glacial acetic acid was added to a 1000 mL Erlenmeyer flask with a magnetic stir bar in an ice bath; (2) while stirring, 3.48 mL of triethylamine was added to the flask; and (3) the flask was filled to volume and mixed well. To the aqueous acetate buffer (40%) was added HPLC-grade methanol (15% v/v) and HPLC-grade acetonitrile (45% v/v). After mixing well, the mobile phase was vacuum filtered and degassed using a 0.45 μm PTFE filter (Lid-X 305 disposable solid liquid separators). The mobile phase flow rate was 1.8 mL/min with sertraline UV detection at 254 nm.

Dissolution results reported as the percent of sertraline dissolved versus time are presented in Table 5-1 (n=3 tablets). Examples 4P, 4Q, 4V, 4X, 4Z, 4AB, 4AC, and 4AD satisfied the dissolution criteria and are sustained release embodiments of this invention. The other formations from Tables 4-1, 4-2 and 4-3 were not tested, but are also sustained release embodiments of this invention.

TABLE 5-1

In Vitro Sertraline Sustained Release from hydrophilic
Matrix Tablet Compositions Designated in Table 4-1, 4-2 and 4-3

| Example | $Q_1$ (%) | $Q_4$ (%) | $Q_8$ (%) | $Q_{12}$ (%) | $Q_{16}$ (%) | $Q_{24}$ (%) |
|---|---|---|---|---|---|---|
| 4P  | 13.2 | 26.6 | 41.4 | 56.1 | 70.0 | 89.7 |
| 4Q  | 9.6  | 20.4 | 32.4 | 47.8 | 60.2 | 75.2 |
| 4V  | 6.3  | 20.9 | 40.2 | 54.0 | 65.1 | 82.1 |
| 4X  | 8.9  | 24.8 | 44.1 | 61.3 | 73.7 | 92.2 |
| 4Z  | 11.3 | 25.8 | 43.0 | 59.0 | 73.3 | 88.4 |
| 4AB | 5.0  | 16.4 | 28.7 | 40.4 | 51.9 | 70.7 |
| 4AC | 5.7  | 19.6 | 37.3 | 54.9 | 70.4 | 92.2 |
| 4AD | 9.6  | 28.5 | 52.0 | 72.4 | 86.2 | 96.8 |

Q = reported values of % drug released represents the average of 3 tablets

EXAMPLE 6

This example demonstrates that certain sertraline side effects (e.g. nausea, regurgitation, and diarrhea) are partially or primarily mediated by direct contact of orally dosed sertraline with the upper gastrointestinal tract, rather than mediated by the presence of sertraline in the systemic circulation after absorption. Bypassing the stomach by dosing sertraline orally in a dosage form which exhibits delayed release before sustained release (i.e., a delayed plus sustained release dosage form) can thus further ameliorate the locally mediated side effects of sertraline.

In a subset of a larger double-blind, randomized, placebo-controlled parallel group study, healthy male human subjects were divided into two groups (Study I). Group A received a single 200 mg sertraline dose as two 100 mg sertraline tablets (Zoloft commercial 100 mg tablets) ("bolus dosing" group). The tablets were administered with 50 ml water. Group B received two placebo tablets. All subjects were dosed after an overnight fast.

Blood samples were withdrawn prior to dosing, and at 0.5, 1, 2, 3, 4, 5, 6, 7, 8, 9, 10, 11, 12, 13, 14, 15, 16, 18, 20, 22, 24, 36, 48, 72, 96, 120, 144, 168, 192, and 240 hr post-dosing. Plasma sertraline concentrations were determined using capillary gas chromatography. Total systemic exposure to sertraline was determined by measuring the area under the plasma sertraline concentration vs. time curve (AUC) for each subject in a given group, and then by calculating a mean AUC for the group. $C_{max}$ is the maximum observed plasma sertraline concentration achieved in a subject. $T_{max}$ is the time at which $C_{max}$ is achieved. After the 200 mg sertraline dose, average $C_{max}$ was 74 ng/ml, average $T_{max}$ was 6 hr, and average AUC was 1646 ng-hr/ml (averaged for 15 subjects).

A similar second study was carried out (Study II). After the 200 mg sertraline dose, average $C_{max}$ was 75 ng/ml, average $T_{max}$ was 5.4 hr, and average AUC was 1744 ng-hr/ml (averaged for 11 subjects). Four subjects in the 200 mg dose group had emesis at 2.6, 2.8, 2.8, and 3.8 hr. The data from these four subjects were not included in the pharmacokinetic averages.

Prior to dosing and each blood sampling time, each subject filled out a questionnaire, which consisted of a series of "Visual Analogue Scales" in which the subject was required to rate, on a scale of 0–10, the severity of certain potent side effects. The subjects were instructed that "0" indicated an absent effect and "10" indicated the worst possible effect. The subjects were instructed to interpolate between 0 and 10 for moderate side effects.

A total of 30 subjects completed Study I: 15 each in Groups A and B. For each side effect evaluated at 30 time points, a total of 900 individual visual-analogue-scale evaluations were obtained. A total of 29 subjects completed Study II: 14 in Group A and 15 in Group B. For each side effect evaluated at 30 time points, a total of 870 individual visual-analogue-scale evaluations were obtained.

Figure 6:
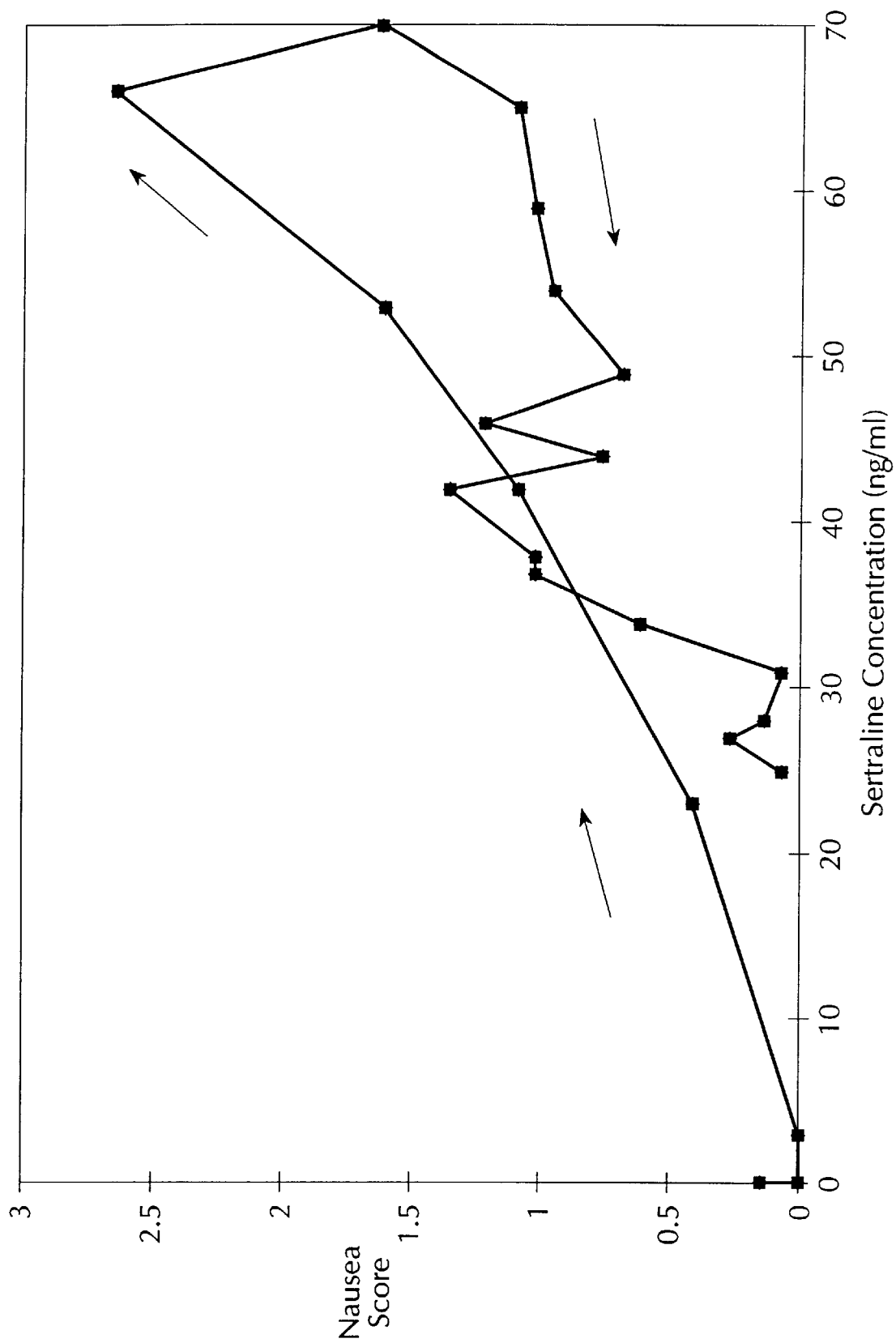
FIG. 6 is a PK/PD plot which presents the relationship between plasma sertraline concentration and average self-reported visual analogue scores for a nausea study presented in the Examples.

FIG. 6 presents the relationship between plasma sertraline concentration and average self-reported visual analogue score for nausea in Study I. This plot, known as a pharmacokinetic-pharmacodynamic relationship plot ("PK/PD Plot"), was obtained as follows. For the 15 subjects in Group A, plasma sertraline concentration was averaged at each blood collection timepoint, to give an average sertraline concentration for Group A at each time point. Likewise, for the 15 subjects in Group A, the visual analogue score for nausea was averaged at each time point. The average nausea scores at each time point (y-axis) were potted vs. sertraline plasma levels at the corresponding time point (x-axis). The arrow on the plot demonstrates the progression of the PK/PD relationship as time progressed. The PK/PD plot of FIG. 6 exhibits "clockwise hysteresis" for the 200 mg bolus dose. Thus as time progressed, the nausea score and the plasma sertraline concentration both increased until the nausea score reached a maximum value, at a plasma sertraline concentration which was below the maximum plasma sertraline concentration $C_{max}$. As $C_{max}$ was reached (at ~70 ng/ml), the nausea score fell to a lower value. As the subsequent plasma sertraline concentrations fell, the nausea score assumed values which were lower than the scores observed for the same plasma sertraline concentrations at earlier timepoints. This "clockwise hysteresis" (or "proteresis") is consistent with the interpretation that sertraline induced nausea is significantly mediated by direct contact of sertraline with the GI tract, and is not entirely mediated by the presence of sertraline in the systemic blood, since the average nausea score is not monotonically related to plasma sertraline concentration. At early time points after dosing (0–3 hr), orally dosed sertraline is primarily in contact with the stomach. Since nausea is not directly monotonically related to plasma sertraline concentration, and is apparently primarily mediated by contact with the gastrointestinal tract, releasing sertraline lower in the gastrointestinal tract, e.g. the duodenum or jejunum, will result in decreased contact time with the upper gastrointestinal wall, and thus less nausea.

In Study 1, diarrhea was also shown to exhibit clockwise hysteresis in its side effect score vs. plasma sertraline concentration curve. The maximum diarrhea score was reached at 3 hr post-dose, long before the observed average plasma $T_{max}$ of 6 hr in these subjects. Thus delaying the release of orally dosed sertraline until the stomach is passed may result in less diarrhea.

As described above, in Study 2, four subjects exhibited regurgitation. Individual PK/PD plots for these subjects, for the side effect regurgitation, exhibited clockwise hysteresis. Thus delaying the release of orally dosed sertraline until the stomach is passed may result in less regurgitation.

EXAMPLE 7

This example illustrates a process for making sustained release sertraline multiparticulates according to the invention. The process for making sustained release sertraline multiparticulates consisted of preparing uncoated sertraline multiparticulate cores by rotary granulating with microcrystalline cellulose as spheronizing agent and water as a granulating agent until a mean granule size of >1 mm was achieved.

Sertraline multiparticulates were prepared using a fluid bed processor with rotor insert (Glatt GPCG-1 by Glatt Air Techniques, Ramsey, N.J.). The rotor bowl was charged with 300 grams of sertraline drug and 300 grams of microcrystalline cellulose as spheronizing agent. Then, water was tangentially sprayed into the rotating bed of drug and microcrystalline cellulose until the agglomeration endpoint (defined by the mean granule size) was reached. After the granulation was completed, the multiparticulates were dried in the rotary fluid bed until their water content was less than 2% (measured by weight loss on drying or LOD). The composition and key process parameters of these multiparticulates are listed in Table 7-1.

Sertraline multiparticulates were prepared using a fluid bed processor with rotor insert (Glatt GPCG-1 by Glatt Air Techniques, Ramsey, N.J.). The rotor bowl was charged with 300–500 grams of sertraline drug and 0–500 grams of microcrystalline cellulose as spheronizing agent. Water, plasticized hydroxypropyl methylcellulose (Opadry™) or polyvinylpyrrolidone (Povidone C15) binder solution (10% solids concentration) was tangentially sprayed into the rotating bed until the agglomeration endpoint (defined by the mean granule size) was reached. The target mean granule size was varied from 100 to 1400 µm during the manufacturing of these formulations. After the granulation was completed, the final multiparticulates were dried in the rotary fluid bed until their moisture content was less than 2% (measured by loss on drying, LOD). A summary of the compositions of multiparticulates manufactured using water as the granulating agent are detailed in Table 8-1 for Examples 8A through 8F. A summary of the multiparticulate core compositions, manufacturing parameters and final mean granule size produced during the manufacture of the formulations that utilized a binder solution consisting of either an aqueous Opadry or Povidone solution as granulating agent are shown in Table 8-2 for Examples 8G–8S.

TABLE 7-1

Sustained Release Sertraline Multiparticulate Composition and Key Manufacturing Parameters Employed During Rotary Granulation Processing

| Example No. | Sertraline* (grams) | Avicel (grams) | Water (grams) | Rotor Speed (rpm) | Spray Rate (g/min) | Endpt LOD (% H2O) | Mean Granule Size (µm) |
|---|---|---|---|---|---|---|---|
| 7A | 300 | 300 | 1100 | 640 | 15–20 | 49 | 1200 |

*sertraline quantities in terms of hydrochloride salt form

EXAMPLE 8

This example illustrates a process for making sustained release sertraline multiparticulates according to the invention that release at different rates depending on the thickness of the sustained-release coating. The process comprises (1) preparing uncoated sertraline multiparticulate cores by rotary granulating with or without microcrystalline cellulose as a granulating agent and water or a binder solution; and (2) applying a rate-limiting coating over the cores. This example further evaluates the release profile of the sustained release multiparticulates.

TABLE 8-1

Sertraline Multiparticulate Core Compositions and Manufacturing Parameters Employed During Rotary Granulation Processing Using Water as Granulating Agent

| Example No | Sertraline (grams) | Avicel (grams) | Water (grams) | Rotor Speed (rpm) | Spray Rate (g/min) | Endpt LOD[b] (% H2O) | Mean Granule Size (µm) |
|---|---|---|---|---|---|---|---|
| 8A | 300 | 300 | 1340 | 640 | 13 | 39 | 320 |
| 8B | 300 | 300 | 1340 | 640 | 12 | 41 | 470 |
| 8C | 500 | 500 | 2950 | 640–585 | 13–15 | 42 | 465 |
| 8D | 335 | 165 | 630 | 630 | 14 | 36 | 510 |
| 8E | 300[a] | 300 | 700 | 630 | 13 | 37 | 370 |
| 8F | 300 | 300 | 1060 | 630 | 12 | 45 | 600 |

[a]jet milled sertraline hydrochloride <10 µm
[b]LOD - Loss on drying

TABLE 8-2

Sertraline Multiparticulate Core Compositions
and Manufacturing Parameters Employed During
Rotary Granulation Processing Using a Binder Solution as Granulating Agent.

| Example No | Sertraline (grams) | Avicel (grams) | Binder (10%) | Rotor Speed (rpm) | Spray Rate (g/min) | Outlet Temp (° C.) | Air Velocity (Pa) | Mean Granule Size ($\mu$m) |
|---|---|---|---|---|---|---|---|---|
| 8G | 500 | 0 | OC | 640 | 5–15 | 33 | 10–14 | 530 |
| 8H | 500 | 0 | OC | 640 | 5 | 34 | 10 | 130 |
| 8I | 500 | 0 | OC | 640 | 5 | 32 | 10 | 205 |
| 8J | 500 | 0 | OC | 640 | 10 | 27 | 12 | 270 |
| 8K | 400 | 100 | OC | 640 | 15 | 30 | 13 | 320 |
| 8L | 375 | 125 | OC | 800 | 26 | 31 | 20 | 680 |
| 8M | 375 | 125 | OC | 810 | 21 | 37 | 10 | 340 |
| 8N | 375 | 125 | PVP | 800 | 25 | 33 | 8 | n.d. |
| 8O | 375 | 125 | OC | 855 | 24 | 36 | 8 | 1400 |
| 8P | 375 | 125 | OC | 855 | 25 | 37 | 8 | 390 |
| 8Q | 375 | 125 | OC | 855 | 24 | 36 | 10 | 510 |
| 8R | 375 | 125 | OC | 855 | 24 | 37 | 12 | 360 |
| 8S | 375 | 125 | OC | 855 | 24 | 36 | 11 | 430 |

OC means Opadry ™ Clear, plasticized hydroxypropyl methylcellulose
PVP means Povidone C15, plasticized polyvinylpyrrolidone Next, the sertraline multiparticulate core granules (Example 8D) were spray coated with a rate-limiting coating in the rotary fluid bed (Glatt GPCG-1, Glatt Air Techniques, Ramsey, N.J.) until the desired end point (coating weight %) was achieved. In this example, the rate-limiting coating was composed of plasticized ethylcellulose (Surelease™) suspension diluted to 25% solids and hydroxypropyl methylcellulose (Opadry™, Colorcon, Inc.) in weight ratios of 85% Surelease™ to 15% Opadry™. This coating was applied to the multiparticulate core granules manufactured according to this Example to coating levels ranging from 5 wt % to 25 wt %.

EXAMPLE 9

This example illustrates the process for making a sustained release sertraline non-erodible matrix tablet. The processing comprises of (1) blending all components except for magnesium stearate; (2) screening and reblending the same components; (3) adding and blending magnesium stearate; and (4) compressing the final blend into tablets. This example further evaluates the in vito release profile of sertraline from the matrix tablets using the in vito test described in the specifications.

In a batch size of 100 grams, sertraline was blended in a suitable jar with all other components except magnesium stearate for 10 minutes us a Turbula shaker system (Base, Switzerland). Next, the blend was passed through a 40 mesh screen and reblended for 5 minutes. Then, magnesium stearate was added to the mixture and blended for 5 minutes. Using the Manesty F-Press (Manesty Machines, Liverpool, England), the final blend was compressed into tablets using conical tablet tooling punches with top-to-base diameter ratio of 1:3 and heigh-to-base ratio of 2:5. A summary of the composition manufactured by direct compression of the formulation blend at 127 mgA sertraline per tablet is shown in Table 9-1.

TABLE 9-1

Sustained Release Non-erodible Matrix Tablet
Composition Manufactured by Direct Compression
on the F-Press with Dosage Strength of 127 mgA/tablet

| % Sertraline Compound* | % Ethocel[1] | % Lactose | % MgSt | Tablet Weight (mg) |
|---|---|---|---|---|
| 33.7 | 40.0 | 24.3 | 2.0 | 420 |

[1]Ethocel ™, Ethylcellulose NF Standard Premium, viscosity 10, Dow Chemical
*sertraline compound quantities in terms of hydrochloride salt form Finished sustained release non-erodible matrix tablets were tested using the in vitro sustained release dosage test procedure described in Example 5. The results are presented in Table 2 (n=1 tablet). This non-erodible matrix tablet satisfies the dissolution criteria and is a sustained release embodiment of this invention.

TABLE 9-2

In Vitro Sertraline Sustained Release from
Non-erodible Matrix Tablet Composition Designated
in Table 9-1 into 900 mL 0.13 M acetate buffer with
0.075 M sodium chloride, pH 4.0 at 37° C. in USP Apparatus #2
with Paddle Speed Setting of 50 rpm

| $Q_1$ (%) | $Q_4$ (%) | $Q_8$ (%) | $Q_{12}$ (%) | $Q_{16}$ (%) | $Q_{24}$ (%) | Release Rate[†] (mgA/hr) |
|---|---|---|---|---|---|---|
| 6.2 | 13.9 | 23.1 | 28.5 | 33.8 | 41.2 | 2.2 |

Q = reported values of % drug released represents one tablet.
[†]means that sertraline release rate was calculated based on the 24 hr time-point because 80% release did not occur within the 24 hr testing period.

EXAMPLE 10

This example illustrates that organic acids have the ability to raise the solubility of the hydrochloride salt of sertraline. The acids were screened by dissolving the candidate add in water and then stirring excess sertraline hydrochloride in the acid solution for at least 8 hours. The concentration of sertraline in the supernatant was then measured by HPLC analysis. The results of this test are listed in Table 10-1, below. Most of the acids listed in the table successfully raised the solubility of sertraline hydrochloride (normal solubility 25 mg/ml).

TABLE 10-1

| Excipient | Approximate Excipient Concentration (mg/ml) | Sertraline Solubility (mg/ml) |
|---|---|---|
| D,L-malic acid | 900 | 21 |
| Citric acid | 600 | 20 |
| Erythorbic acid | 400 | 19 |
| Adipic acid | 14 | 12 |
| Maleic acid | 700 | 6.4 |
| L-aspartic acid | 10 | 5.5 |
| Tartaric acid | 1400 | 5.5 |
| L-glutamic acid | 12 | 5.4 |
| Fumaric acid | 11 | 3.1 |
| Tannic acid | 2000 | 2.8 |
| D,L-tyrosine | 600 | 2.2 |

Preferred acids, based on this screening test, are malic, citric, erythorbic, and adipic acids. Mateic, L-aspartic, tarlaric, and L-glutamic acids also significantly improved sertraline hydrochloride solubility. Some controlled-release dosage forms with such acids in the core will perform better than those without such acids. This is particularly true for osmotic-based formulations that deliver a solution of drug.

EXAMPLE 11

This example illustrates that organic acids have the ability to raise the solubility of the acetate salt of Sertraline by a method similar to that used for the hydrochloride salt described in Example 10. The excipient excipient concentration, and sertraline solubility are listed in Table 11-1 below. Based on these results, preferred acids to include in a dosage form where increased Sertraline acetate solubility is desired are ascorbic, erythorbic, citric, lactic, aspartic, glutamic, and aconitic acids.

TABLE 11-1

| Excipient | Excipient Concentration (mg/ml) | Sertraline Solubility (mg/ml) |
|---|---|---|
| Ascorbic acid | 400 | >425 |
| Erythorbic acid | 400 | >330 |
| Citric acid | 600 | 146 |
| Lactic acid | 213 | >294 |
| Aspartic acid | 7 | 110 |
| Glutamic acid | 12 | 108 |
| Aconitic acid | 500 | >92 |
| Itaconic acid | 150 | 72 |
| Succinic acid | 77 | 28 |
| None | — | 64 |

EXAMPLE 12

This example illustrates that organic acids and three calcium salts have the ability to raise the aqueous solubility of the lactate salt of sertraline using a method similar to that used for the hydrochloride salt described in Example 10. The excipient, the excipient concentration in the aqueous test solution, and the Sertraline lactate solubility in the test solution are listed in Table 12-1 below. Solubility of Sertraline lactate in water is approximately 125 mg/ml. The data below show that eight organic solutions had sertraline lactate solubilities of about the same or higher than 125 mg/ml; adipic, erythorbic, itaconic, citric, aspartic, glutamic, histidine, and ascorbic. Also, a solution of a mixture of two of these acids also had high solubility; ascorbic and aspartic Sertraline lactate solubility was also high in calcium salt solutions, either alone (calcium citrate) or mixed with ascorbic acid.

TABLE 12-1

| Excipient | Excipient Concentration (mg/ml) | Sertraline Lactate Solubility (mg/ml) |
|---|---|---|
| Adipic acid | 14 | 360 |
| Erythorbic acid | 400 | >217 |
| Itaconic acid | 150 | >202 |
| Citric acid | 600 | 162 |
| Aspartic acid | 7 | >155 |
| Glutamic acid | 12 | >125 |
| Histidine | 42 | >116 |
| Ascorbic/Aspartic | 400/7 | 116 |
| Ascorbic | 400 | 102 |
| Glycine | 250 | 66 |
| Aconitic acid | 200 | <59 |
| Tartaric acid | 1400 | 12 |
| Fumaric acid | 11 | <9 |
| Sorbic acid | 3 | <9 |
| Calcium lactate/ Ascorbic acid | 50/400 | 160 |
| Calcium citrate | 10 | 165 |
| Calcium carbonate/ Ascorbic acid | 50/400 | 176 |
| None | — | 125 |

EXAMPLE 13

The lower solubility of the sertraline chloride salt and of all sertraline lactate and sertraline acetate salts in the presence of high chloride concentrations suggest that core formulations are preferred for which sertraline stays in solution that is, it does not precipitate or form a gel-like material when chloride is present. Certain organic acids and salts were found to inhibit precipitation or gelation of Sertraline when chloride is present via the following screening test. Sertraline lactate was dissolved in water either alone (as a control) or with a candidate excipient. Sodium chloride was then added (as a concentrated solution) and the result observed. An excipient was considered beneficial if the solution remained clear and fluid. The more chloride that could be added to an excipient solution with the solution remaining clear, the more beneficial was the excipient. Table 13-1 below shows the results of this screening test, indicating that all the excipients tested increased sertraline concentration in the chloride solutions.

TABLE 13-1

| Excipient | Excipient Concentration (mg/ml) | Concentration NaCl (mM) | Final Sertraline Concentration (mg/ml) | Observation After NaCl Addition |
|---|---|---|---|---|
| None | — | 38 | 22 | gel/precipitate |
| Ascorbic/ Aspartic acids | 400/7 | 152 | 162 | solution |
| Aspartic acid | 7 | 114 | 162 | solution |
| | 7 | 152 | 100 | gel |
| Ascorbic acid | 400 | 100 | 102 | precipitate |
| Ascorbic acid/ calcium lactate | 400/50 | 150 | 165 | solution |
| Ascorbic acid/ calcium carbonate | 400/50 | 150 | 170 | slightly turbid |
| Citric acid/ calcium lactate | 600/50 | 150 | 162 | solution |
| Histidine | 42 | 150 | 110 | slight precipitate |

EXAMPLE 14

Organic compounds (solubilizers) were screened for their ability to enhance the solubility of sertraline lactate in aqueous with or without the presence of chloride. Excess sertraline lactate was added to an aqueous solution of the candidate solubilizer and, in most cases an organic acid. The organic acids were saturated in these solutions and the additional solubizing agents were at the concentration shown in Table 14-1. The equilibrium sertraline solubility was measured. Then, sodium chloride was added to the saturated solution and the final sertraline concentration was measured. The results of these screening tests are summarized in Table 14-1.

5 minutes in a microcentrifuge to pack the powder. 150 µl gastric buffer was added to the packed powder and the samples were gently agitated,then spun at 14K G in a microcentrifuge for 2 minutes. The samples were then removed from the microcentrifuge and allowed to stand undisturbed until the solution was removed. The solution was removed from the samples after a total of 10 minutes after gastric buffer was added to the powder pack, and analyzed by HPLC to determine the sertraline concentration.

TABLE 14-1

| | Solubilizer | Solubilizer Concentration (mg/ml) | Organic Acid | Sertraline Solubility (mg/ml) | NaCl Concentration (mM) | Sertraline Concentration (with NaCl) |
|---|---|---|---|---|---|---|
| 1 | None (control) | — | none | 125 | 150 | 5 |
| 27 | Monocaprylin | 10 | ascorbic | 160 | 150 | 160 |
| 3 | Triacetin | 100 | ascorbic | 170 | 150 | 170 |
| 4 | Monobutyrin | 50 | none | 120 | 150 | 120 |
| 5 | Diacetin | 50 | ascorbic | 120 | 150 | 120 |
| 6 | Imwitor ® 312 | 10 | ascorbic | 120 | 150 | 120 |
| 7 | Imwitor ® 375 | 10 | ascorbic | 120 | 150 | 120 |
| 8 | Imwitor ® 742 | 50 | none | 120 | 150 | 120 |
| 9 | Imwitor ® 988 | 50 | none | 140 | 100 | 140 |
| 10 | Triethyl citrate | 50 | ascorbic | 160 | 150 | 160 |
| 11 | Pluronic ® L31 | 50 | none | 120 | 100 | 120 |
| 12 | Cremophore EL | 50 | ascorbic | 120 | 150 | 120 |
| 13 | Sucrose acetate isobutyrate | 50 | ascorbic | 120* | 150 | 120 |
| 14 | Sodium capryl lactate | 50 | ascorbic | 120 | 150 | 120 |
| 15 | Sucrose monolaurate | 50 | none | 150 | 150 | 150 |
| 16 | Sodium lauryl lactate | 50 | ascorbic | 120 | 150 | 120 |
| 17 | Span ® 80 | 50 | ascorbic | 120 | 150 | 120 |

EXAMPLE 15

This example illustrates that solubilizers for sertraline also can increase the rate of dissolution of sertraline. The effect of a candidate excipient on sertraline dissolution rate was determined by adding solid drug, the candidate solubilizing excipient, and, in some cases, other excipients such as an organic acid and an osmagent (such as a sugar) to a 1.8 ml centrifuge tube. The sample tubes were spun at 14K G for The dissolution rate (mg sertraline/ml-min) was calculated from the measured concentration on of dissolved sertraline in the supernatant as a function of time over the first 10 minutes of dissolution. These dissolution rates and the excipient mixtures for which they were measured are summarized in Table 15-1 below. As shown, several excipient mixtures containing solubilizers significantly (about 3× or greater) increased the dissolution rate of sertraline, compared with sertraline alone and compared with sertraline and ascorbic acid.

TABLE 15-1

| Candidate Excipient | | Organic | | | | Other | | Sertraline | Sertraline Dissolution |
|---|---|---|---|---|---|---|---|---|---|
| Name | Concentration (wt %) | Organic Acid | Acid Conc. (wt %) | Osmagent | Osmagent Conc. (wt %) | Other Excipient | Excipient Conc. (wt %) | Salt Form Conc. (wt %) | Rate (mg/ml-min) |
| None | — | none | — | none | — | none | — | lactate 100 | 0.9 |
| None | — | ascorbic | 51.0 | lactose | 20 | none | — | lactate 14 | 3.5 |
| Imwitor ® 312 | 5.0 | ascorbic | 49.5 | lactose | 12.5 | CaCO₃ | 5 | lactate 14 | 20.9 |
| Lecithin | 5.0 | ascorbic | 51.0 | lactose | 15 | none | — | lactate 14 | 10 |
| PEG 3550 | 5.0 | ascorbic | 51.0 | lactose | 15 | none | — | lactate 14 | 9.3 |
| Capmul ® MCM | 5.0 | ascorbic | 71.0 | none | — | none | — | lactate 24 | 14.5 |
| Capmul ® MCM | 4.7 | none | none | lactose | 17 | CaCO₃ Ca citrate | 4.7 47 | lactate 13.1 | 4.3 |
| Imwitor ® 191 | 5.0 | ascorbic | 49.5 | lactose | 12.5 | CaCO₃ | 1.0 | lactate 14 | 8.0 |
| Myrerol ® (18–99) | 5.0 | ascorbic | 49.5 | lactose | 12.5 | none | — | lactate | 6.4 |

TABLE 15-1-continued

| Candidate Excipient | | Organic | | | | Other | Sertraline | Sertraline Dissolution |
|---|---|---|---|---|---|---|---|---|
| Name | Concentration (wt %) | Organic Acid | Acid Conc. (wt %) | Osmagent | Osmagent Conc. (wt %) | Other Excipient | Excipient Conc. (wt %) | Salt Form Conc. (wt %) | Rate (mg/ml-min) |
| Span ® 60 | 5.0 | ascorbic | 51.0 | lactose | 15 | none | — | 14 lactate | 9.5 |
| Ascorbyl palmitate | 6.8 | none | none | lactose | 74.2 | none | — | 14 lactate | 4.3 |
| Methyl paraben/ propyl paraben/ propyl gallate | 0.5/0.5/1.0 | ascorbic | 50.0 | lactose | 17.5 | none | — | 19 lactate | 11.5 |
| Imwitor ® 312 | 6.8 | aspartic | 74.2 | none | — | none | — | 14 lactate 19 | 5.3 |

EXAMPLE 16

This examples illustrates a method for making osmotic tablets comprising a tablet core containing sertraline surrounded by a semipermeable asymmetric membrane coating. Sertraline-hydrochloride was triturated by hand for 10 minutes with citric acid and microcrystalline cellulose (Avicel PH 102, FMC) using a 6½ inch diameter mortar and pestle. Magnesium stearate was then blended in as a lubricant by sting with a spatula for 60 seconds. The weight ratio of Sertraline-hydrochloride to citric acid to microcrystaline cellulose to magnesium stearate was 8.5:63.8:23.7:4; with a total weight of 10 grams. The blended mixture was pressed into 470 mg tablets in a modified hydraulic jack (manufactured by Dayton) fitted with a pressure gauge and ⅜ inch concave punch under 2500 PSI pressure for 2 seconds. The dimensions of the resulting tablets were ⅜ inch in diameter and ¼ inch thick. A semipermeable membrane coating (as described in U.S. patent application No. 397,974, allowed Oct. 6, 1996, entitled The Use of Asymmetric Membranes in Delivery Devices) was applied to these tablets using a LDCS-20 pan coater (Vector Corp.) at a spray rate of 20 grams per minute, an inlet temperature of 40C and air flow of 40 cfm. The coating solution contained by weight 10% Cellulose acetate, (Eastman Chemical, CA398-10), 2.5% polyethylene glycol (BASF, PEG 3350), 15% water and 72.5% acetone. The coated tablets were dried 1 hour at 50C before testing. After drying, the weight of applied coating material was 15.4% of the total weight. These tablets contained a sertraline dose of 50 mgA/tablet.

EXAMPLE 17

Osmotic delivery tablets were prepared by using essentially the same procedure for making the tablet cores and applying the asymmetric membrane coating to the cores described in Example 16. The composition of the cores and coating solution varied from that used in Example 16 as shown in Table 17-1. Example 16 is listed in Table 17-1 for comparison. Significant core compositional changes shown include: the Sertraline salt form, the type and amount of solubilizer, and the type and amount of osmagent. The amount of binder (Avicel) lubricant (magnesium stearate), and solubilizer were varied as necessary to obtain good tableting and wetting properties. These tablets contained a sertraline dose of 50 mgA/tablet.

TABLE 17-1

| Example No. | Core Weight (mg) | Drug Salt Form | Wt % | Acid Type | Wt % | Solubilizer Type | Wt % | Osmogent Type | Wt % | Avicel wt % | Mg St. wt % | Other | Polymer Type | Polymer wt % | PEG wt % | Water wt % | Coating Weight (dry wt %) |
|---|---|---|---|---|---|---|---|---|---|---|---|---|---|---|---|---|---|
| 16 | 470 | chloride | 12 | none | | none | | lactose | 66 | 20 | 2 | none | CA | 10 | 2.5 | 15 | 15.4 |
| 17a | 470 | lactate | 14 | none | | none | | lactose | 65.4 | 19.3 | 1.33 | none | EC | 6 | 4 | 8 | 1 |
| 17b | 470 | acetate | 14 | ascorbic | 50 | none | | lactose | 20 | 15 | none | Myrj | EC | 6 | 4 | 10 | 10.1 |
| 17c | 470 | lactate | 14 | ascorbic | 50 | none | | lactose | 15 | 21 | none | none | EC | 6 | 4 | 10 | 10.1 |
| 17d | 470 | lactate | 14 | citric | 50 | none | | lactose | 20 | 15 | none | Tween | EC | 6 | 4 | 10 | 9.9 |
| 17e | 470 | lactate | 14 | aspartic | 11 | none | | fructose | 38 | 29.5 | 2.5 | Ca Acetate | CA | 10 | 2.5 | 15 | 11 |
| 17f | 470 | lactate | 14 | none | | Im | 5 | lactose | 58.4 | 20 | 2.6 | none | EC | 6 | 4 | 10 | 10 |
| 17g | 470 | lactate | 14 | none | | Im | 5 | xylitol | 53.5 | 25 | 2.5 | none | CA | 10 | 2.5 | 15 | 15.5 |
| 17h | 470 | lactate | 14 | ascorbic | 50 | MC | 5 | lactose | 12.5 | 12.5 | none | Myrj | EC | 6 | 4 | 10 | 10.5 |
| 17i | 470 | lactate | 14 | glutamic | 10 | MC | 5 | sucrose | 50 | 15 | none | Ca lactate, Myrj | EC | 6 | 4 | 10 | 10.5 |

TABLE 17-1-continued

| Example No. | Core Composition | | | | | | | | | | | Osmotic Coating Solution | | | | Coating Weight (dry wt %) |
|---|---|---|---|---|---|---|---|---|---|---|---|---|---|---|---|---|
| | Core Weight (mg) | Drug Salt Form | Acid Type | Wt % | Solubilizer Type | Wt % | Osmogent Type | Wt % | Avicel wt % | Mg St. wt % | Other | Polymer Type | Polymer wt % | PEG wt % | Water wt % | |
| 17j | 470 | lactate | 14 | aspartic | 11 | MC | 5 | sucrose | 53 | 15 | | Myrj | EC | 6 | 4 | 10 | 10.1 |
| 17k | 470 | lactate | 14 | ascorbic | 32 | Im | 5 | lactose | 12 | 29 | 3 | CaCO₃ | EC | 7 | 3 | 6 | 15.1 |
| 17l | 470 | lactate | 14 | ascorbic | 32 | Im | 5 | lactose | 12 | 29.5 | 2.6 | CaCO₃ | EC | 6 | 4 | 10 | 10.1 |
| 17m | 470 | lactate | 14 | aspartic | 11 | Im | 5 | fructose | 36 | 27 | 2.5 | Ca acetate | CA | 10 | 2.5 | 15 | 10.3 |
| 17n | 470 | lactate | 14 | glycine | 25 | Im | 5 | fructose | 28.6 | 25 | 2.5 | none | CA | 10 | 2.5 | 15 | 15.9 |
| 17o | 560 | lactate | 11.2 | ascorbic | 36.5 | Triacetin | 4.2 | lactose | 16.2 | 31.1 | none | Myrj | EC | 6 | 4 | 10 | 10 |
| 17p | 470.5 | lactate | 13.9 | succinic | 37.2 | PEG | 15.9 | lactose | 37.9 | none | none | Klucel, SLS | EC | 6 | 4 | 10 | 10 |
| 17q | 536 | lactate | 12.1 | ascorbic | 44 | Capmul | 4.4 | lactose | 12 | 22.1 | 1.5 | CaCO₃ | EC | 6 | 4 | 10 | 9.9 |
| 17r | 470 | lactate | 14 | ascorbic | 37 | Span 60 | 5 | lactose | 11.4 | 25 | 2.6 | CaCO₃ | EC | 6 | 4 | 10 | 9.5 |
| 17s | 470 | lactate | 14 | ascorbic | 37 | Lecithin | 5 | lactose | 11.4 | 25 | 2.6 | CaCO₃ | EC | 6 | 4 | 10 | 9.9 |
| 17t | 470 | lactate | 14 | ascorbic | 32 | Im | 5 | lactose | 12 | 29.5 | 2.7 | CaCO₃ | EC | 7 | 3 | 6 | 17 |
| 17u | 470 | lactate | 14 | ascorbic | 32 | Im | 5 | lactose | 12 | 29.5 | 2.7 | CaCO₃ | EC | 6 | 4 | 8 | 15 |
| 17v | 470 | lactate | 14 | aspartic | 11 | Im | 5 | fructose | 35 | 27 | 2.5 | Ca acetate | CA | 10 | 2.5 | 15 | 20 |
| 17w | 470 | lactate | 14 | aspartic | 11 | none | | fructose | 38 | 29.5 | 2.5 | Ca acetate | CA | 10 | 2.5 | 15 | 10 |

IM = Imwitor 312
Capmul = Capmul MCM
Tween = Tween 80
CA = cellulose acetate 398-10
MC = monocaprylin
Mg St. = magnesium stearate
Klucel = Klucel EF
EC = Ethocel S-100
PEG = polyethylene glycol 3350
Myrj = Myrj 52
SLS = sodium lauryl sulfate

EXAMPLE 18

The rates of release of Sertraline from selected formulations described in Examples 16 and 17 were determined according to the procedures described in Example 5 with the exceptions that 750 ml of solution was used in the dissolution apparatus and the stirring speed was 100 rpm. Analysis of Sertraline released was determined by reverse-phase high-performance liquid chromatography (RP HPLC).

The results of release-rate tests performed using these procedures are listed in Table 18-1. The first two formulations listed, 18a and 18b (formulations 16 and 17a), show release rates lower than claimed in this invention and are included as comparison examples. Both of these formulations contain a sertraline salt (hydrochloride or lactate) and only lactose as the osmagent and no solubilizing excipients. Formulations 18c, 18e, and 18h listed in Table 18-1 all contain a solubilizing excipient and all demonstrate sustained release of sertraline and are embodiments of this invention. Formulations 18d, 18f, and 18g are delayed plus sustained release embodiments of this invention. Likewise the remaining formulations in example 17 (17 b-w) are also sertraline formulations that are embodiments of this invention.

TABLE 18-1

| Sertraline Release Test No | Tablets of Example No | Fraction of Drug Released (%) At Specified Time | | | | | | |
|---|---|---|---|---|---|---|---|---|
| | | 0 Hr | 1 Hr | 2 Hr | 4 Hr | 8 Hr | 12 Hr | 20 Hr |
| 18a | 16 | 0 | 0 | 0 | 0 | 0 | 0 | 0 |
| 18b | 17a | 0 | 0 | 1 | 2 | — | 10 (17 hr) | 12 |
| 18c | 17e | 0 | 6 | 15 | 35 | 62 | 76 | 78 |
| 18d | 17j | 0 | 0 | 0 | 4 | 19 | 28 | 44 |
| 18e | 17m | 0 | 8 | 19 | 37 | 60 | 73 | 83 |
| 18f | 17n | 0 | 0.7 | 6 | 17 | 37 | 54 | 78 |
| 18g | 17v | 0 | 0.4 | 4 | 13 | 31 | 41 | 53 |
| 18h | 17w | 0 | 8 | 18 | 38 | 56 | 64 | 66 |

EXAMPLE 19

This example illustrates osmotic-based sertraline tablets that consist of an inner core containing an osmagent and solubilizing excipient surrounded by a sertraline and excipient layer and then surrounded by a semipermeable coating. The tablets of this example varied from the other examples in that an inner core containing acid, binder and solubilizer was made, tableted, and placed inside a larger drug containing tablet. Citric acid and microcrystalline cellulose (Avicel, PH 102, FMC) were triturated by for 5 minutes using a 4½ inch diameter mortar and pestle. Polyoxyethylene 40 monostearate (Myrj 52, BASF) was then added and triturated for 1 minute. The weight ratio of citric acid to microcrystalline cellulose to Myrj was 86.1:9.8:4.1, with a total weight of 4 grams. The blended mixture was pressed into 232 mg tablets as in Example 16 except that the tablet punch was ¼ inch. The resulting tablet core was ¼ inch in diameter and ¼-inch thick. The blend for the outer tablet was prepared like Example 17. It contained sertraline lactate, citric acid, lactose. Avicel, and polyoxyethylene sorbitan (Tween 80, ICI) in a weight ratio of 14:50:20:15:1. The final tablet was made by placing 200 mg of the drug containing blend into the bottom of the standard ⅜-inch die then the 232-mg citric add tablet was placed on top of this and an additional 270 mg of the drug containing blend poured onto the top. The tablet was then pressed using the same conditions as in Example 16. The dimensions of the resulting tablet were ⅜ inch in diameter by ½-inch thick. A semipermeable membrane coating was applied to the tablets using the same method as in Example 16. Results from release rate tests similar to those described in Example 5 indicate that this osmotic formulation of sertraline is an embodiment of this invention.

EXAMPLE 20

This example illustrates a method for making an osmotic tablet consisting of a bilayer tablet core surrounded by a semipermeable coating. To form the drug containing granulation the following materials are blended and wet granulated in a mixer: 50 to 200 g sertraline and its pharmaceutically acceptable salts; from 250 to 325 g of polyethylene oxide having a molecular weight of about 100,000 and from 0 to 275 g of a polyethylene oxide having a molecular weight of about 200,000, from 10 to 30 g of a hydroxypropylmethylcellulose having an average molecular weight of about 11,300; and from 0 to 10 mg of a magnesium stearate. The second granulation to make the second layer in the tablet core comprises from about 110 to 140 g of a polyethylene oxides having an average molecular weight ranging from about 5,000,000 to 7,500,000; from 5 to 25 g of a hydroxypropylmethylcellulose having an average molecular weight of about 11,300; from 40 to 70 g of sucrose; and, from 0 to 10 g of magnesium stearate. These granulations are used to make a bilayer tablet core with one layer containing sertraline and the second layer mostly swellable hydrophilic materials. These bilayer tablets are then coated with a semipermeable coating comprising 70% to 98% cellulose acetate having an acetyl content of 32% to 39.8%, and from 2 to 30% of polyethylene glycol having an average molecular weight of about 3350. In the coating at least one exit passageway is formed on the sertraline-containing side of the tablet.

EXAMPLE 21

Osmotic delivery tablets were prepared with a water permeable outer coating through which were drilled delivery ports for the passage of sertraline dissolved in the aqueous solution containing the tablet core. Tablet cores composed of 14.0 wt % sertraline lactate, 11.0 wt % aspartic acid, 47.4 wt % sucrose, 25.0 wt % Avicel PH 101, and 2.6 wt% magnesium stearate (total core weight was 470 mg) were prepared by essentially the same method given in Example 17. These tablet cores were then coated with a solution composed of 6% ethylcellulose (Ethocel S-100, Dow Chemical), 4 wt % polyethylene glycol (PEG 3350, BASF) and 8 wt % water in acetone using the method described in Example 17 such that the coming weight was 70.4 mg per tablet (total coated tablet weight was 540.4 mg). For some of the tablets, 3 holes, each 340 μm in diameter, were drilled in each face of each tablet (total of 6 holes per tablet). For a second set of tablets, 18 holes, each 340 μm in diameter, were drilled in each face of each tablet (total of 36 holes per tablet).

A tablet of each type was each tested for sertraline release using 0.75 L of acetate/saline buffer as described in Example 5. The percent sertraline released to the receptor solution as a function of time for each type of tablet is shown in Table 21-1, below. Both types of tablets showed similar release profiles, indicating that release of drug is predominately osmoically driven, (if rlease was predominately diffusional, the tablets with 36 holes should release drug approximately 6 times faster than the tablets with 6 holes).

TABLE 21-1

| Time (hr) |سertraline Released (%) | |
|---|---|---|
| | 6-Hole Tablet | 36-Hole Tablet |
| 0 | 0 | 0 |
| 1 | 3 | 7 |
| 2 | 12 | 17 |
| 4 | 26 | 32 |
| 8 | 44 | 44 |
| 12 | 47 | 46 |

EXAMPLE 22

This example describes swelling hydrogel controlled release sertraline tablets. Sertraline hydrochloride or acetate or lactate or aspartate (50 mgA sertraline) is blended with 20K molecular weight polyethylene oxide (PEO-20K) (350 mg) with other solubilizers and excipients, and the blend is tabletted on a Manesty Type-F3-press. The tablets are spray-coated with a solution of cellulose acetate in acetone/ethanol, to a final dry weight coating of 14% of the total coated tablet weight A 2 mm diameter hole is drilled (via mechanical, laser or other means) through the coating on one face of a portion of the tablets. A 2 mm diameter hole is drilled through the entire center of the tablet for another portion of the tablet.

EXAMPLE 23

This example describes swelling hydrogel controlled release sertraline tablets. Sertraline hydrochloride or acetate or lactate or aspartate (50 mgA sertraline) is blended with 20K molecular weight polyethylene oxide (PEO-20K) (350 mg) with other solubilizers and excipients, and the blend is tabletted on a Manesty Type-F3-press. The tablets are spray-coated with a solution of cellulose acetate/hydroxypropylcellulose (1:1) in a 9:1 acetone/methanol solution, to a final coating weight of 15% of the total coated tablet weight.

EXAMPLE 24

This example describes swelling hydrogel controlled release sertraline tablets. Sertraline hydrochloride or acetate or lactate or aspartate (50 mgA sertraline) is blended with 100K molecular weight polyethylene oxide (PE-100K) (350 mg) with other solubilizers and excipients, and the blend is tabletted on a Manesty Type-F3-press. The tablets are spray-coated wish a solution of cellulose acetate in acetone/ethanol, to a final dry weight coating of 14% of the total coated tablet weight A 2 mm diameter hole is drilled (via mechanical, laser or other means) through the coating on one face of a portion of the tablets. A 2 mm diameter hole is drilled through the entire center of the tablet for another portion of the tablets.

EXAMPLE 25

This example describes swelling hydrogel controlled release sertraline tablets. Sertraline hydrochloride or acetate or lactate or aspartate (50 mgA sertraline) is blended with 20K molecular weight polyethylene oxide (PEO-20K) (350 mg) with other solubilizers and excipients, and the blend is tabletted on a Manesty Type-F3-press. The tablets are spray-coated with a suspension of sucrose (50/60 mesh) in an acetone solution of cellulose acetate (2.5%) and PEG-600 (2.5%). The weight ratio of cellulose acetate to PEG-600 to sucrose in the coating is 1:1:2. The final coating is 15% of the total coating tablet weight.

EXAMPLE 26

This example describes swelling hydrogel controlled release sertraline tablets. Sertraline hydrochloride or acetate or lactate or aspartate (50 mgA sertraline) is blended with 20K molecular weight polyethylene oxide (PEO-20K) (350 mg) with other solubilizers and excipients, and the blend is tabletted on a Manesty Type-F3-press. The tablets are spray-coated with a 9/1 acetone/methanol solution of cellulose acetate (2.2%) and hydroxypropylcellulose (HPC) (2.2%). The weight ratio of cellulose acetate to HPC in the coating is 1:1, and the final coating is 15% of the total coated tablet weight.

EXAMPLE 27

This example describes a perforated coated sustained release sertraline tablet formulation which releases sertraline through a central hole. Sertraline hydrochloride or acetate or lactate or aspartate (50 mgA sertraline) is blended with lactose, magnesium stearate, and optionally ethylcellulose and other excipients, and the blend is tabletted on a Manesty Type-F3-press. The tablets are coated with a solution of ethylene vinyl acetate in methanol. After drying, the coating weight is 15% of the total weight of the uncoated tablets. A 2 mm diameter hole is drilled (via mechanical, laser or other means) though the coating on one face of a portion of the tablets. A 2 mm diameter hole is drilled through the entire center of the tablet for another portion of the tablets. The sertraline release rate is varied by varying the ethylcellulose content of the tablet.

EXAMPLE 28

This example describes preparation of a pH-triggered (enteric-coated) spatially delayed plus sustained release sertraline tablet. Sertraline sustained release matrix or osmotic or coated hydrogel tablets tablets are prepared as in Examples 4, 9, 16, 17, 19, 20, 21, 22, 23, 24, 25, 26 and 27.

A coating formulation is prepared according to the formulation in Table 28-1.

TABLE 28-1

| Coating Formulation | | |
|---|---|---|
| COMPONENT | FUNCTION | 6 WT % |
| Eudragit L30D-55 | enteric polymer | 16.0 |
| triethyl citrate | plasticizer | 1.6 |
| Talc | detackifying agent | 4.0 |
| water | solvent | 78.4 |

The coating solution is sprayed onto sertraline sustained release tablets using a Freund HCT-30 Hi-Coated. Coats [Eudragit polymer+triethyl citrate+talc] are applied ranging from 5–25% of the uncoated tablet weight. These coated tablets release little or no sertraline at the pH of the stomach, and release sertraline in a sustained manner (1 mgA/hr to 40 mgA/hr) after moving into the duodenum.

EXAMPLE 29

This example illustrates a process for making pH-triggered spatially delayed plus sustained release sertraline multiparticulates.

Sustained release sertraline multiparticulates are prepared as described in Examples 7 and 8. A Wurster bottom spray fluid bed processor (Glatt GPCG-1) is used to apply a delayed release coating. Typical delayed release coating levels are ~5% to ~50%. The delayed-release coating is a suspension containing 12.3% metacrylic acid copolymers (Eudragit® L 30 D-55), 6.2% talc, 1.5% triethyl citrate and 8% water.

Because the delayed release coating is soluble in environments where the pH is greater than 5.5, the multiparticulates thus prepared prevent release of sertraline from the coated particle cores in the stomach, where the pH is low, and permit release of sertraline from the coated particle cores in the small intestine and color, where the pH is greater than 5.5.

EXAMPLE 30

This example illustrates a process for making pH-triggered spatially-delayed plus sustained release sertraline multiparticulates, with a protective layer between the sustained release multiparticualate core and the pH-triggering delayed release membrane. This dosage form design ameliorates any physical or chemical incompatibilities between the sustained release core and the delayed-release membrane. The process comprises (1) preparing sustained release sertraline multiparticulate cores; (2) applying a protective coat over the core particles; and (3) applying a second, pH-sensitive, delayed release coating over the first coat.

Sustained release sertraline multiparticulate cores are prepared as described in Examples 7 and 8. Using a fluid bed processor, onto the sustained release core particles a solution containing 5% plasticied hydroxypropyl methylcellulose (Opadry®) solution is sprayed until a coating of 10% is applied.

A delayed release coating (typically 5% to 50% of the final weight of the coated multiparticulates) is applied using the same fluid bed processor as above. The delayed-release coating is a suspension containing 12.3% methacrylic acid copolymers (Eudragit® L 30 D-55), 62% talc, 1.5% triethyl citrate and 80% water.

EXAMPLE 31

This example illustrates the preparation of a pH-triggered spatially delayed plus sustained release sertraline coated tablet with a Cellulose Acetate Phthalate Coat.

Sertraline sustained release tablets are manufactured as in Examples 4, 9, 16, 17, 19, 20, 21, 22, 23, 24, 25, 26 and 27. The sustained release tablets are then spray-coated with an acetone solution of cellulose acetate phthalate (CAP) in a HCT-60 Hi-Coater® spray-coating apparatus (Freund Ind. Corp., Tokyo). The CAP is plasticized with 25% (by weight) diethylphtalate (DEP). Sufficient CAP is sprayed onto the tablets to result in a final coating polymer weight, after drying, of 5–50 wt %, relative to the weight of the uncoated tablet bed.

EXAMPLE 32

This example illustrates the preparation of a pH-triggered spatially delayed CAP-coated sustained release sertraline tablet with a barrier coat.

Sustained release sertraline tablets are manufactured as described in Examples 4, 9, 16, 17, 19, 20, 21, 22, 23, 24, 25, 26 and 27. Tablets are spray coated with a solution of hydroxypropylmethylcellulose (HPMC; Colorcon, Inc.) in water, using a HCT-60 Hi-Coater. In this manner, tablets are coated with a 5 wt % barrier coat of HPMC, relative to the initial sustained release tablet weight. Tablets are then further spray-coated with cellulose acetate phthalate (CAP) and DEP plasticizer (as described in Example 31, in the HCT-60 Hi-Coater. Sufficient CAP is sprayed onto the tablets to result in a final coating polymer weight, after drying, of 5–50 wt %, relative to the weight of the uncoated tablet. The HPMC coat serves as a barrier between the sustained release sertraline tablet and the pH-sensitive CAP coat. This barrier coat prevents premature dissolution (or weakening) of the CAP coat, e.g., in the low pH environment of the stomach, potentially caused by a locally higher pH in the tablet interior due to the presence of sertraline.

EXAMPLE 33

This example if illustrates the preparation of a pH-triggered spatially-delay (acrylic resin-coated) plus sustained release sertraline tablet with a barrier coat.

Sustianed release sertraline tablets are manufactured as described in Examples4, 9, 16, 17, 19, 20, 21, 22, 23, 24, 25, 26 and 27. Sustained release sertraline tablets are spray coated with a solution of hydroxypropylmethylcellulose (HPMC) (Colorcon, Inc.) in water, using a HCT-60 HI-Coater. In this manner, tablets are coated with a 5 wt % barrier coat of HPMC, relative to the initial tablet weight.

A coating formulation is prepared according to the formulation in Table 28-1.

The coating solution is sprayed onto HPMC-coated sustained release sertraline tablets using a Freund HCT-30 Hi-Coater.

The total acrylic resin polymer weight applied is 5–50% of the weight of the sertraline sustained release tablet bed. The HPMC undercoat serves as a barrier between sertraline and the pH-sensitive acrylic resin coal. This barrier coat prevents premature dissolution (or weakening) of the acrylic resin coat, e.g., in the low pH environment of the stomach, potentially caused by a locally higher pH in the tablet interior due to the presence of sertraline.

EXAMPLE 34

This example illustrates preparation of a temporally-delayed (water-activated) plus sustained release sertraline tablet dosage form.

Sustained release sertraline tablets are manufactured as described in Examples 4, 9, 16, 17, 19, 20, 21, 22, 23, 24, 25, 26 and 27. These tablets are then coated with a water-soluble and/or water-disintergrable delay layer, in a tablet coating apparatus such as an HCT-30, HCT-60, or HCT-130 Coater (Freund Inc). The tablet are coated with an aqueous solution of HPMC to a final coating weight of 5–50% of the final weight of the coated tablet. Heavier coating weights give longer delays before initiation of sertraline release into the use environment (the gastrointestinal lumen). The delay time may also be increased by incorporating small to moderate quantities of poorly water-soluble polymers (including but not limited to ethylcellulose (EC), cellulose acetate (CA), cellulose acetate butyrate) into the coating formulation. For example, the coating formulation may consist of 95:5 HPMC/EC to 50:50 HPMC/EC, or 95:5 HPMC/CA to 50:50 HPMC/CA. In the case of such mixed polymer coating systems, it may be necessary to adjust the solvent composition to dissolve the mixture of water-soluble and poorty water-soluble polymers. For example, mixtures of acetone ethanol and water may be used as needed.

In the environment of use, the dosage forms of this example exhibit a delay in sertraline release, during which time the coating polymer dissolves from the sertraline delayed plus sustained release tablet surface. After the delay, the sertraline sustained release tablet releases its incorporated sertraline at a rate between 1 mg/hr and 40 mg/hr.

EXAMPLE 35

This example illustrates a method for making osmotic tablets comprising a tablet core containing sertraline-lactate surrounded by a semipermeable asymmetric membrane coating. Tablet cores were made using equipment standard in the pharmaceutical industry. Tablet core components comprising 13.8 wt % sertraline-lactate, 11 wt % L-aspartic acid, 5 wt % calcium acetate 29.5 wt % microcrystalline cellulose, and 38.2 wt % fructose were blended, then run through a roller compactor and milled. This milled material was then blended with 2.5 wt % magnesium stearate to form the final blended material that was used to make tablets having a total weight of 470 mg on a conventional tablet press (Kilian T-100). Semipermeable asymmetric membrane coatings (as described in U.S. pat. No. 5,612,059) were applied to the tablets using a side-vented pan coater (LDCS-20, Vector Corp.). The coating solution, comprising 10 wt % cellulose acetate 398-10, 25 wt % polyethylene glycol 3350, 15 wt % water, and 72.5 wt % acetone, was spray-coated onto the tablets at a rate of 20 g/min until a 10 wt % coating level on the tablets had been achieved.

EXAMPLE 36

This example illustrates a method for making osmotic tablets comprising a tablet core containing sertraline-lactate surrounded by a semipermeable asymmetric membrane coating. Tablet cores were made using equipment standard in the pharmaceutical industry. Tablet core components comprising 13.8 wt % sertraline-lactate, 5 wt % glyceryl monolaurate, 11 wt % L-aspartic acid, 5 wt % calcium acetate, 27 wt % microcrystalline cellulose, and 35.7 wt % fructose were used to make the tablet cores. Initially the glycerol monolaurate was wet granulated with 14 wt % microcrystalline cellulose using ethanol (95%) as the wet granulation solvent. After drying and milling, the wet granulate was blended with the components listed above (including the balance of microcrystalline cellulose), then run through a roller compactor and milled. This milled material was then blended with 2.5 wt % magnesium stearate to form the final blended material that was used to make tablets having a total weight of 470 mg on a conventional tablet press (Kilian T-100). Semipermeable asymmetric membrane coatings (as described in U.S. Pat. No. 5,612, 059) were applied to the tablets using a side-vented pan coater (LDCS-20, Vector Corp.). The coating solution, comprising 10 wt % cellulose acetate 398-10, 2.5 wt % polyethylene glycol 3350, 15wt % water, and 72.5 wt % acetone; was spray-coated onto the tablets at a rate of 20 g/min. One batch of tablets was made with a 10 wt % coating and a second batch of tablets was made having a 20 wt % coating.

EXAMPLE 37

Sertraline acetate. Sertraline base (the compound of Preparation AA, 200.2 mg) was dissolved in ethyl acetate (200 μL) in a 5 ml reaction vial. Glacial acetic acid (41.2 μL) was added to the sertraline base solution with stirring. An additional 500 μL of ethyl acetate was added to facilitate stirring. The reaction mixture was allowed to granulate at room temperature for five hours. The solids were filtered, washed with 10 mL of ethyl acetate and then dried in a vacuum oven at 40° C. for 20 hour. The yield was determined to be 16%. mp 126° C.

EXAMPLE 38

Sertraline acetate. Sertraline base, (the compound of Preparation AA, 200 mg) was dissolved in hexane (1.5 mL) in a 10 mL reaction vial. The solution was heated to 40° C. Glacial acetic acid (41.2 μL) was added to the sertraline base solution. The reaction mixture was allowed to cool to room temperature and then granulate for one hour. The solids were filtered and dried in a vacuum oven at 40° C. for 72 hours. The yield was determined to be 90%. mp 126° C.

EXAMPLE 39

Sertraline acetate. Sertraline hydrochloride (125 g) was slurried in a mixture of water (1 L) and (2.5 L). NaOH (25% aqueous, 35 mL) was added. Sertraline base partitioned into the hexane phase. The hexane layer was separated. The aqueous layer was extracted a second time with hexane (500 mL). The hexane layers were combined. The solution of sertraline base in hexane was heated to 50° C. Glacial acetic acid (23 ml) was added to the solution of sertraline base. The reaction mixture was stirred at 50° C. for 30minutes. The reaction mixture was allowed to cool to room temperature and stirred at room temperature overnight. The crystals were filtered and washed five times with a total of 250 mL of hexane. The solids were dried at 40° C. in a vacuum oven for 48 hours. The yield was 89%. mp 126° C.

EXAMPLE 40

Single Crystal X-ray Analysis. A representative was surveyed and a 1 Å data set (maximum sin θ/λ0.5) was collected on a Siemens R3RA/v diffractometer, Siemens Analytical X-ray Systems, Inc., 6300 Enterprise Lane, Madison, Wis. 53719-1173. Atomic scattering factors were taken from the International Tables for X-ray Crystallography. International Tables for X-ray Crystallography, Vol. IV, pp. 55, 99, 149 Birmingham: Kynoch Press, 1974. All crystallographic calculations were facilitated by the SHELXTL system. G. M. Sheldrick SHELXTL User Manual, Nicolet Instrument Corp., 5225 Verona Rd, Madison, Wis. 53711, 1981). All diffractometer data were collected at room temperature. Pertinent crystal, data collection, and refinement parameters are summarized in Table 40-1 below.

A trial structure was obtained by direct methods. This trial structure refined routinely. A difference map revealed a small amount of water located on a two-fold axis. Refinement indicated that the population of this water was 0.25. Hydrogen positions were calculated wherever possible. The methyl hydrogens and the hydrogens on nitrogen were located by difference Fourier techniques. The hydrogens on the water were not located. The hydrogen parameters were added to the structure factor calculations but were not refined. The shifts calculated in the final cycle of least squares refinement were all less than 0.1 of their corresponding standard deviations. The final R-index was 8.97%. A final difference Fourier revealed no missing or misplaced electron density.

The refined structure, shown in FIG. 1, was plotted using the SHELXTL plotting package described in said SHELXTL User Manual. The absolute configuration was not established.

TABLE 40-1

Crystal Parameters of Sertraline-Acetate

| | |
|---|---|
| Formula | $C_{17}H_{18}NCl_2^+ C_2H_3O_2^- - 0.25\ H_2O$ (371.3) |
| Crystallization Medium | water |
| Crystal size (mm) | 0.10 × 0.16 × 0.22 |
| Cell dimensions | a = 15.629(8) Å |
| | b = 8.695(3) Å |
| | c = 15.048(3) Å |
| | α = 90.0° |
| | β = 110.45(3)° |
| | γ = 90.0° |
| | V = 1916(1) Å |
| Space Group | C2 |
| Molecules/unit cell | 4 |
| Density, calculated, $g/cm^3$ | 1.287 |
| Linear Absorption Factor, $mm^{-1}$ | 3.144 |

TABLE 40-2

Atomic Coordinates (× $10^4$) and equivalent isotropic displacement coefficients ($Å^2 × 10^3$)

| | x | y | z | U (eq)* |
|---|---|---|---|---|
| C(1) | 8321 (14) | 10711 (22) | −3626 (12) | 79 (2) |
| C(2) | 7559 (13) | 10583 (20) | −3227 (12) | 66 (2) |
| C(3) | 7581 (14) | 8997 | −2770 (12) | 83 (2) |
| C(4) | 8453 (11) | 8847 (21) | −1902 (11) | 67 (2) |
| C(5) | 9260 (11) | 9344 (22) | −2182 (12) | 66 (2) |
| C(6) | 9268 (14) | 10390 (22) | −2917 (12) | 87 (2) |
| C(7) | 10033 (16) | 10928 (24) | −3028 (14) | 103 (2) |
| C(8) | 10898 (14) | 10516 (24) | −2347 (14) | 91 (2) |
| C(9) | 10883 (16) | 9557 (24) | −1637 (14) | 97 (2) |
| C(10) | 10115 (12) | 9074 (21) | −1513 (12) | 67 (2) |
| C(11) | 8555 (14) | 7256 (22) | −1473 (14) | 79 (2) |
| C(12) | 8418 (12) | 6975 (22) | −625 (12) | 66 (2) |
| C(13) | 8514 (14) | 5542 (25) | −215 (12) | 89 (2) |
| C(14) | 8760 (12) | 4314 (21) | −708 (18) | 90 (2) |
| C(15) | 8861 (18) | 4526 (27) | −1587 (15) | 132 (2) |
| C(16) | 8763 (14) | 6002 (22) | −1905 (13) | 88 (2) |
| N(17) | 8112 (9) | 9728 (19) | −4522 (10) | 65 (2) |
| C(18) | 8616 (14) | 10130 (25) | −5161 (13) | 98 (2) |
| Cl(19) | 8377 (5) | 5313 (12) | 862 (4) | 127 (2) |
| Cl(20) | 8816 (6) | 2473 (13) | −178 (6) | 144 (2) |
| C(1A) | 9993 (16) | 5929 (28) | −3685 (16) | 157 (3) |
| C(2A) | 9026 (12) | 5594 (27) | −4223 (12) | 83 (2) |
| O(3A) | 8771 (11) | 4331 (19) | −4476 (12) | 119 (2) |
| O(4A) | 8464 (12) | 6651 (19) | −4306 (11) | 116 (2) |
| O(1W) | 10000 (37) | 2700 (33) | −5000 (37) | 132 (4) |

*Equivalent isotropic U defined as one third of the trace of the orthogonalized $U_{ij}$ tensor.

EXAMPLE 41

Osmotic Tablets of Sertraline Acetate. This example illustrates a method for making osmotic tablets comprising a tablet core containing sertraline acetate surrounded by a semipermeable asymmetric membrane coating. Tablet cores were made using equipment standard in the pharmaceutical industry. Tablet core components comprising sertraline acetate (14 wt %), ascorbic acid (50 wt %), lactose (20 wt %), microcrystalline cellulose (15 wt %) and polyethylene glycol stearyl ether (1 wt %, Myrj 52, Sigma Chemical, St. Louis, Mo.) were blended by hand using a mortar and pestle. The blended material was used to make tablets having a total weight of 470 mg on a single-station tablet press (F-press). Semipermeable asymmetric membrane coatings (as described in U.S. Pat. No. 5,612,069, the teachings of which are incorporated herein by reference) were applied to the tablets using a side-vented pan coater (LDCS-20, Vector Corp., 675 44th St, Marion, Iowa 52302). The coating solution, comprising ethyl cellulose S-100 (6 wt %), polyethylene glycol 3350 (4 wt %), water (10 wt %), and acetone (80 wt %), was spray-coated onto the tablets at a rate of 20 g/minute until a 10 wt % coating level on the tablets had been achieved.

EXAMPLE 42

This example illustrates a process for making multiparticulates for use in making delayed-release dosage forms designed to release sertraline predominantly below the stomach. The process comprises (1) preparing uncoated sertraline acetate multiparticulate cores; (2) applying a protective coat over the core particles; and (3) applying a second, pH-sensitive, delayed release coating over the first coat.

Multiparticulate cores containing drug are prepared using a fluid bed processor with rotor insert (Model GPCG-1, Glatt Air Techniques, Ramsey, N.J. 07446). The rotor bowl is initially charged with 400 gA of sertraline drug (as sertraline acetate, sertraline lactate or sertraline aspartate) and a binder solution containing 5% poly(ethyl acrylate, methyl acrylate) (Eudragit® NE-30-D), 5% plasticized hydroxypropyl methylcellulose (Opadry®, Colorcon, West Point, Pa. 19486) and 90% water is sprayed into the rotating bed until an average core granule size of about 250 μm is achieved.

Onto the uncoated core particles in the same fluid bed processor with rotor insert, a binder solution containing 5% plasticized hydroxypropyl methylcellulose (Opadry®) solution is sprayed until a coating of 10% is applied. This intermediate coating enhances the adhesion to the core particles of the final delayed release coating.

A delayed release coating (typically 5% to 50% is required to meet the delayed release criterion) is applied using the same fluid bed processor as above. The delayed-release coating is a suspension containing 12.3% methacrylic acid copolymers (Eudragit® L 30 D-55, Rohm GMBH, Darmstadt, Germany; U.S. Office: Somerset, N.J.) 6.2% talc, 1.5% triethyl citrate and 80% water. The final product is a delayed-release multiparticulate with particles having an average size of about 300 μm.

EXAMPLE 43

Sertraline L-lactate. Sertraline base (the compound of Preparation AA, 200 mg) was dissolved in ethyl acetate (200 μL) in a 10 mL conical reaction vial. L-Lactic acid (solid, 68.5 mg) was separately dissolved in ethyl acetate(100 μL). The L-lactic acid solution was added to the sertraline base solution under constant stirring with a magnetic stirrer. A precipitate was observed within about 2 minutes after complete addition of the L-lactic acid solution to the sertraline base solution. The reaction mixture was allowed to granulate overnight (18 hour) at room temperature. The precipitate was filtered and the solid was rinsed with 1 mL of ethyl acetate. The solid was dried in a vacuum oven at 40° C. for 20 hours. The dried sold was characterized and identified as the L-lactate salt of sertraline. The yield was determined to be 72%. mp 153° C.

EXAMPLE 44

Sertraline L-lactate. Sertraline base (the compound of Preparation AA, 1.0 g) was dissolved in ethyl acetate (20 mL) in a 50 mL round bottom flask and the solution was heated to 40° C. L-Lactic acid (342.5 mg) was separately dissolved in ethyl acetate (5 mL). The L-latic acid solution was added in small portions to the solution in the round bottom flask which was constantly stirred with a magnetic stirred. The reaction mixture was stirred at 40° C. for 2 hours after the addition of the L-lactic acid solution was complete. The reaction mixture was then allowed to cool to room temperature and the solids were filtered. The solids were washed with 5 mL of ethyl acetate and then dried under vacuum at 40° C. for 24 hours. The dried solid was identified as the L-lactate salt of sertraline. The yield was calculated to be 86%. mp 153° C.

EXAMPLE 45

Sertraline L-lactate. Sertraline base (10 g)was dissolved in isopropanol (150 mL) in a 500 mL round bottom flask and the solution was heated to 40° C. L-Lactic acid (3.4 g) was separately dissolved in ethyl acetate (25 mL). The L-lactic acid solution was added in small portions to the solution in the round bottom flask which was constantly stirred with a magnetic stirrer. The reaction mixture was stirred at 40° C. for 4 hours after the addition of the L-lactic acid solution was complete. The reaction mixture was then allowed to cool to room temperature and the solids were filtered. The solids were washed with 50 mL of hexane and then dried under vacuum at 40° C. for 48 hours. The dried solid was identified as the L-lactate salt of sertraline. The yield was calculated to be 94%. mp 153° C.

EXAMPLE 46

Sertraline L-lactate. Sertraline mandelate (750 grams) was slurried in a mixture of water (3.9 L) and ethyl acetate (3.9 L). The slurry was cooled to 15° C. NaOH (25% aqueous, 250 mL) was added, resulting in a solution with pH 9.6. The free base of sertraline was partitioned into the ethyl acetate layer which was separated. The aqueous layer was extracted with an additional 3.4 liters of ethyl acetate. The combined ethyl acetate layers were washed with 3.9 liters of water. The ethyl acetate layer containing sertraline base was concentrated under vacuum and filtered to clarify the solution. To this solution was added L-lactic acid (155 g). The reaction mixture was granulated hr 20 hours at room temperature. The solids were filtered, washed 4 times with ethyl acetate(400 mL each time). The crystals were dried overnight under vacuum at 40° C. The yield was calculated to be 84%. mp 153° C.

EXAMPLE 47

Sertraline L-lactate. Sertraline hydrochloride (300 g) was slurried in a 3:1 mixture of water (3 liters) and ethyl acetate (1 liter). The pH of the slurry was adjusted to 8.0 by the addition approximately 1 liter of 1N sodium hydroxide solution. The free base of sertraline partitioned into the ethyl acetate phase. The two phases were allowed to separate completely by allowing the biphasic solution to stand overnight without agitation. The ethyl acetate layer was then separated and washed twice with 3 liters of deionized water to remove chloride ions. The final ethyl acetate layer containing sertraline base was concentrated to 300 mL under vacuum to remove residual water. The ethyl acetate solution containing sertraline base was heated to 40° C. L-lactic acid was dissolved in ethyl acetate to form a 7.5 M solution. The lactic acid solution was added to the sertraline base solution in small portions with constant agitation. The mixture was allowed to stir and granulate overnight (16–20 hours). The crystals were filtered and washed 4 times with an equal volume (200 mL each) of ethyl acetate. The crystals were dried overnight in a vacuum oven at 40° C. The yield was 97%. mp 153° C.

EXAMPLE 48

Single Crystal X-Ray Analysis. A representative crystal was surveyed and a 1 Å data set (maximum $\sin \theta/\lambda = 0.5$) was collected on a Siemens R3RA/v diffractometer. Atomic scattering factors were taken from the International Tables for X-ray Crystallography, Vol. IV, Kynoch Press, Birmingham, 1974, pp. 55, 99 and 149. All crystallographic calculations were facilitated by the SHELTXL (see G. M. Sheldrick, SHELTXL. User Manual, Nicolet Instrument Corp., 5225 Verona Rd, Madison, Wis. 53711, 1981) system. All diffractometer data were collected at room temperature. Pertinent crystal, data collection, and refinement parameters are summarized in Table 48-1.

TABLE 48-1

Crystal Parameters of Sertraline L-lactate

| | |
|---|---|
| Formula | $C_{17}H_{18}NCl_2^+C_3H_5O_3^-$ (396.3) |
| Crystallization Medium | ethyl acetate |
| Crystal size (mm) | 0.07 × 0.07 × 0.11 |
| Cell dimensions | a = 8.660(5) Å |
| | b = 24.43(1) Å |
| | c = 9.382(3) Å |
| | α = 90.0° |
| | β = 91.94(3)° |
| | γ = 90.0° |
| | V = 1984(2) Å³ |
| Space Group | $P2_1$ |
| Molecules/unit cell | 4 |
| Density, calculated, g/cm³ | 1.327 |
| Linear Absorption Factor, mm⁻¹ | 3.101 |

A trial structure was obtained by direct methods. This trial structure refined routinely. Hydrogen positions were calculated wherever possible. The methyl hydrogens and the hydrogens on nitrogen and oxygen were located by difference Fourier techniques. The hydrogen parameters were added to the structure factor calculations but were not refined. The shifts calculated in the final cycle of least squares refinement were all less than 0.1 of their corresponding standard deviations. The final R-index was 5.49%. A final difference Fourier revealed no missing or misplaced electron density.

Figure 3:
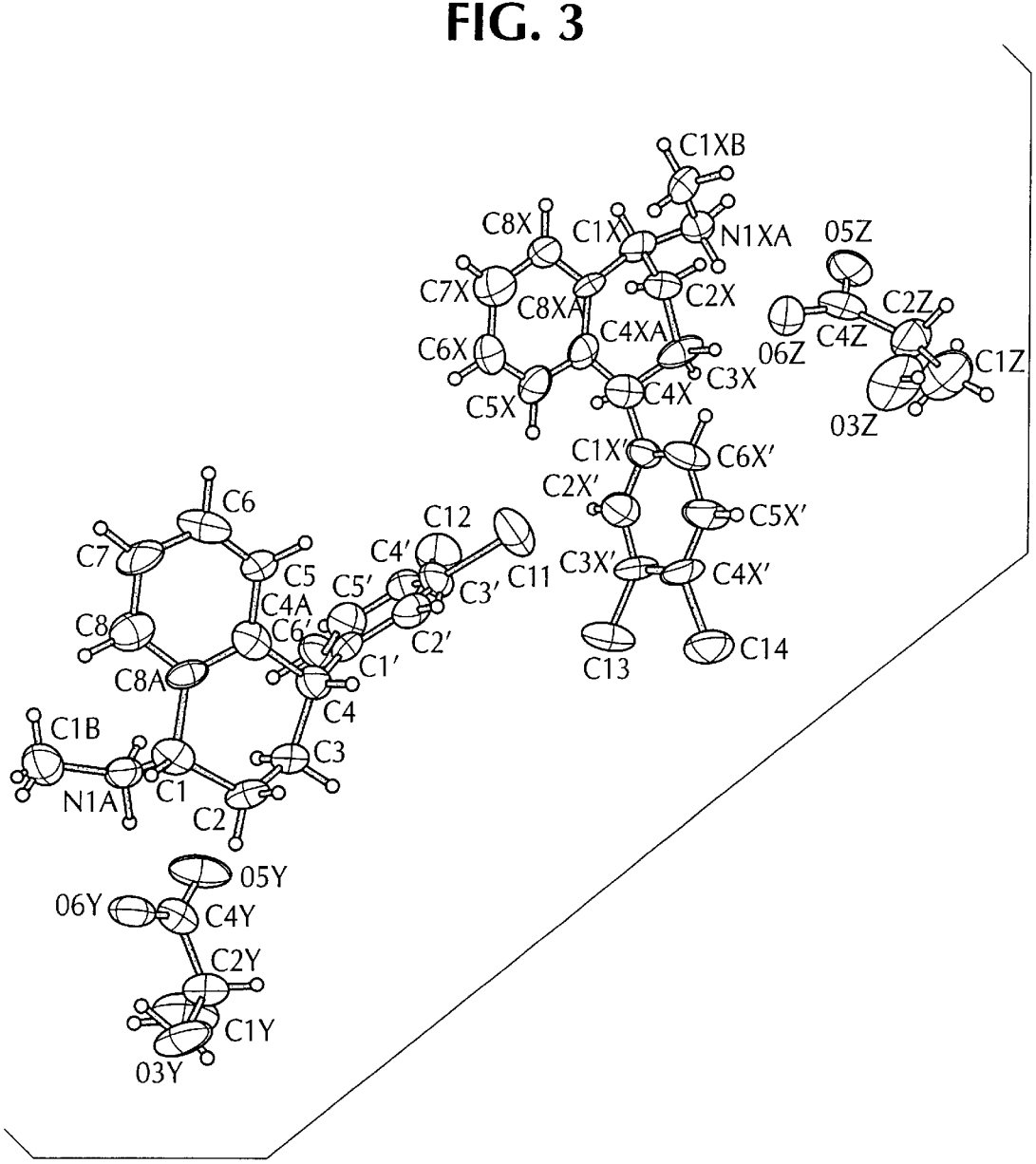
FIG. 3 is an X-ray crystal structure of sertraline L-lactate as derived from single crystal X-ray crystallography. (Atomic coordinates).
Figure 4:
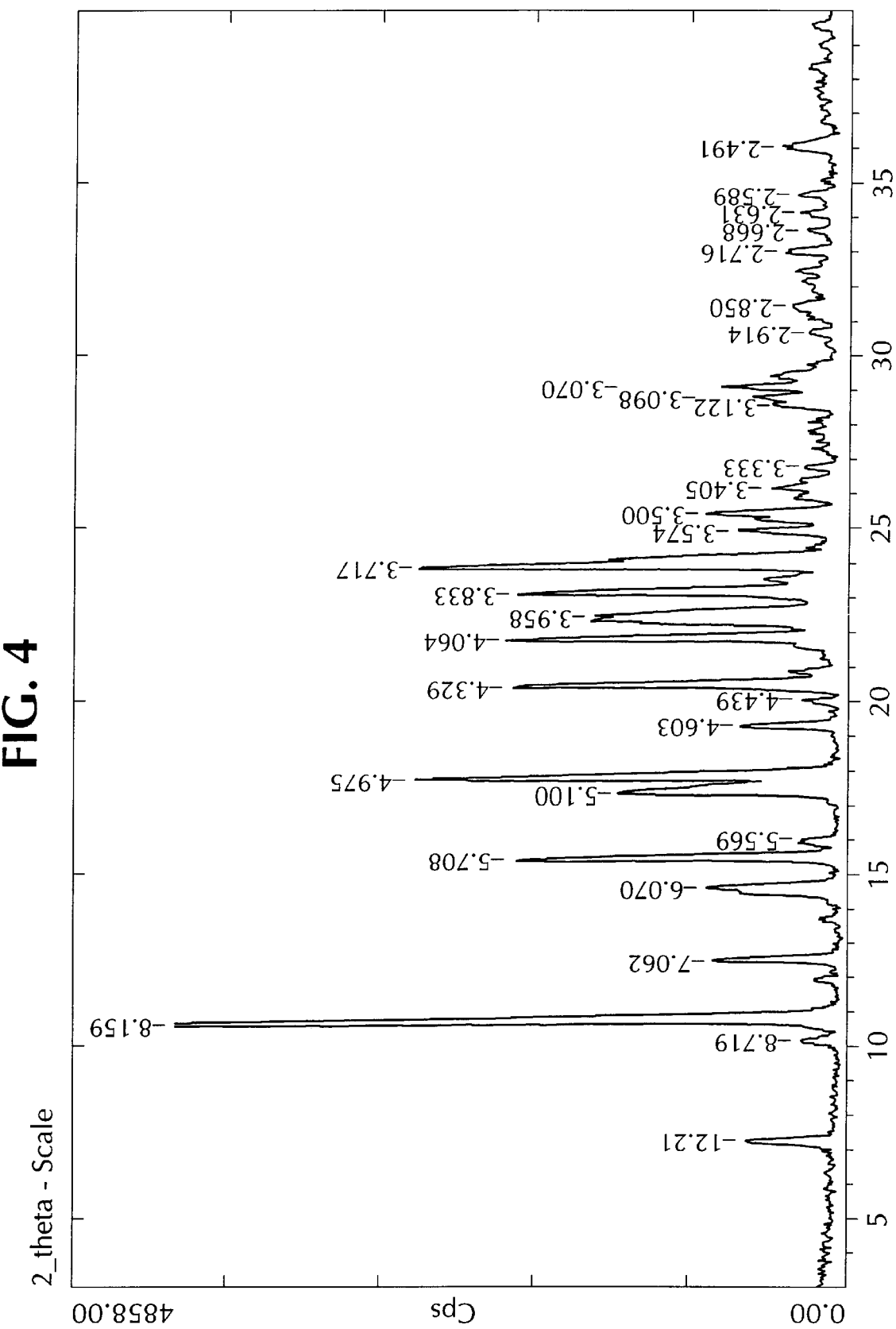
FIG. 4 is a characteristic X-Ray diffraction pattern showing that sertraline L-lactate is crystalline. (Vertical Axis: Intensity (CPS); Horizontal Axis: Two theta (degrees)).
Figure 5:
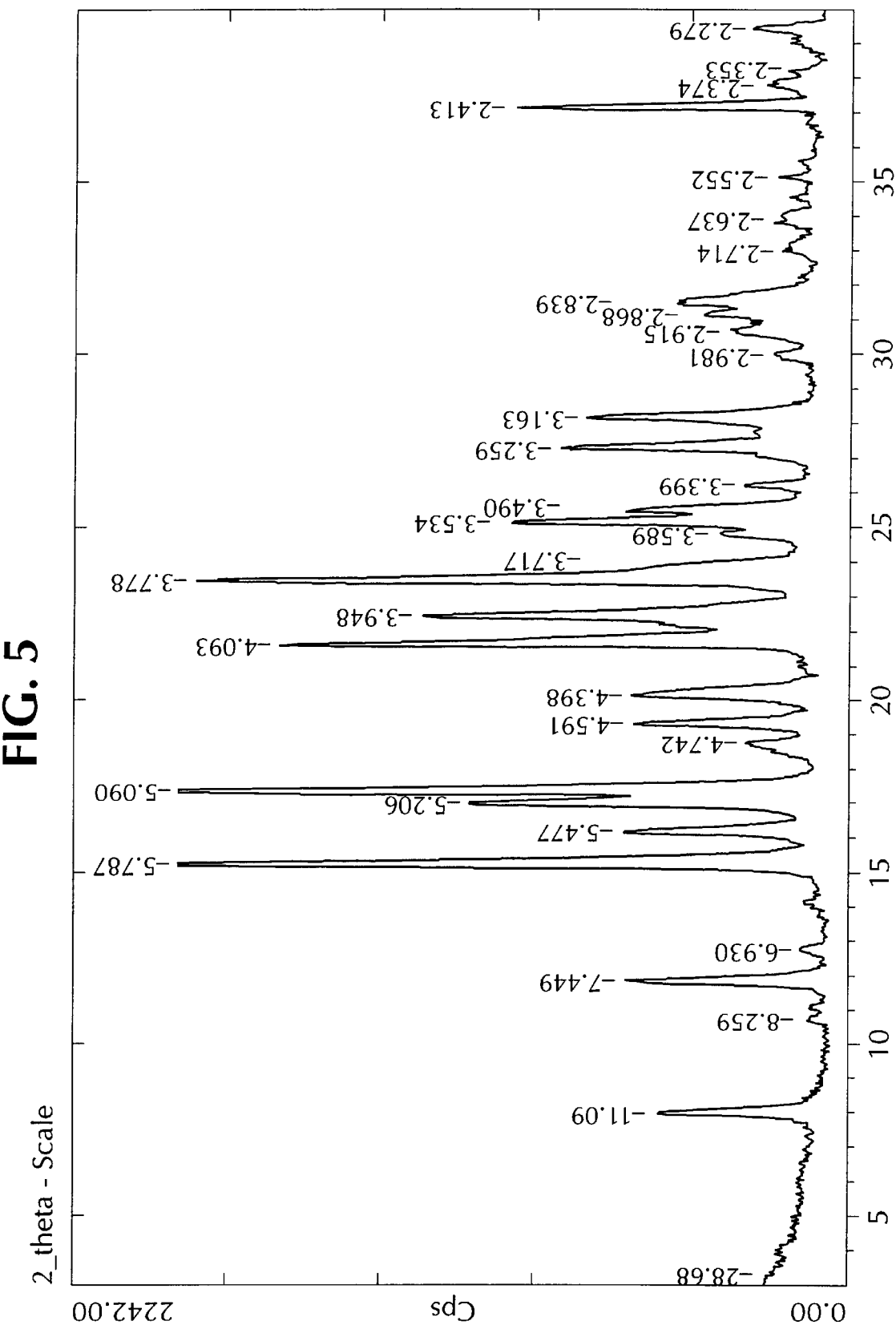
FIG. 5 is a characteristic X-Ray diffraction pattern showing, that sertraline L-aspartate is crystalline. (Vertical Axis: Intensity (CPS); Horizontal Axis: Two theta (degrees)).

The refined structure, shown as FIG. 3, was plotted using the SHELTXL plotting package. The absolute configuration was determined by the method of Ibers and Hamilton (Hamilton, Acta Cryst, 1965, 18, 502–510 and Ibers et al., Acta Cryst., 1964, 17, 781–782). The X-Ray absolute configuration was in agreement with the L-laclate configuration. The atomic coordinates are set forth in Table 48-2.

TABLE 48-2

Atomic Coordinates (× 10⁴) and equivalent isotropic displacement coefficients (Å² × 10³)

| | x | y | z | U (eq)* |
|---|---|---|---|---|
| C(1) | −4173(13) | 4373(5) | 7866(10) | 44(2) |
| N(1A) | −4127(10) | 3773(4) | 7483(9) | 47(2) |
| C(1B) | −5542(14) | 3455(6) | 7614(12) | 69(2) |
| C(2) | −2556(12) | 4576(6) | 8220(10) | 54(2) |
| C(3) | −1658(12) | 4605(5) | 6877(11) | 55(2) |
| C(4) | −2328(12) | 5027(5) | 5834(10) | 44(2) |
| C(4A) | −4064(12) | 4979(5) | 5658(10) | 45(2) |
| C(5) | −4860(13) | 5273(5) | 4565(11) | 49(2) |
| C(6) | −6411(15) | 5250(6) | 4430(12) | 68(2) |
| C(7) | −7291(13) | 4981(6) | 5430(13) | 68(2) |
| C(8) | −6563(13) | 4705(5) | 6491(12) | 56(2) |
| C(8A) | −4955(12) | 4700(5) | 6662(10) | 39(2) |

TABLE 48-2-continued

Atomic Coordinates (× 10⁴) and equivalent isotropic displacement coefficients (Å² × 10³)

| | x | y | z | U (eq)* |
|---|---|---|---|---|
| C(1') | −1539(12) | 5015(5) | 4411(10) | 46(2) |
| C(2') | −1022(12) | 5517(5) | 3816(10) | 52(2) |
| C(3') | −308(13) | 5493(5) | 2508(11) | 52(2) |
| Cl(1) | 243(5) | 6117(2) | 1757(4) | 91(1) |
| C(4') | −9(13) | 5024(6) | 1820(11) | 54(2) |
| Cl(2) | 972(4) | 4996 | 258(3) | 81(1) |
| C(5') | −486(14) | 4545(5) | 2414(11) | 56(2) |
| C(6') | −1219(14) | 4538(5) | 3694(11) | 52(2) |
| C(1X) | 495(13) | 7219(5) | −5303(11) | 47(2) |
| N(1XA) | 648(11) | 7826(4) | −4926(9) | 50(2) |
| C(1XB) | −814(13) | 8109(5) | −4598(12) | 58(2) |
| C(2X) | 2126(14) | 7016(5) | −5601(12) | 67(2) |
| C(3X) | 3130(13) | 6938(6) | −4263(11) | 64(2) |
| C(4X) | 2437(13) | 6525(5) | −3240(10) | 53(2) |
| C(4XA) | 702(12) | 6586(5) | −3183(11) | 46(2) |
| C(5X) | −45(14) | 6304(5) | −2112(12) | 55(2) |
| C(6X) | −1610(15) | 6299(5) | −1995(13) | 65(2) |
| C(7X) | −2501(16) | 6604(6) | −2945(14) | 80(2) |
| C(8X) | −1807(13) | 6890(5) | −4024(12) | 56(2) |
| C(8XA) | −206(12) | 6900(5) | −4117(10) | 39(2) |
| C(1X') | 3233(13) | 6545(5) | −1796(10) | 49(2) |
| C(2X') | 3944(14) | 6083(5) | −1250(11) | 58(2) |
| C(3X') | 4642(13) | 6084(5) | 101(11) | 52(2) |
| Cl(3) | 5554(5) | 5501(2) | 743(3) | 85(1) |
| C(4X') | 4732(14) | 6569(6) | 875(11) | 62(2) |
| Cl(4) | 5695(4) | 6600(2) | 2528(3) | 78(1) |
| C(5X') | 3978(14) | 7023(5) | 350(11) | 62(2) |
| C(6X') | 3293(15) | 7006(5) | −982(11) | 63(2) |
| C(1Y) | 1318(16) | 2575(6) | 9581(14) | 106(2) |
| C(2Y) | 540(13) | 3113(5) | 9839(11) | 57(2) |
| O(3Y) | 103(10) | 3150(5) | 11268(8) | 87(2) |
| C(4Y) | −786(14) | 3217(5) | 8778(12) | 49(2) |
| O(5Y) | −479(11) | 3255(5) | 7509(8) | 86(2) |
| O(6Y) | −2081(10) | 3239(4) | 9294(8) | 65(2) |
| C(1Z) | 6352(15) | 8746(8) | −2633(15) | 110(2) |
| C(2Z) | 4677(13) | 8843(6) | −2407(12) | 66(2) |
| O(3Z) | 4349(11) | 8757(5) | −1000(8) | 101(2) |
| C(4Z) | 3602(14) | 8483(5) | −3343(11) | 50(2) |
| O(5Z) | 3800(10) | 8497(4) | −4676(7) | 66(2) |
| O(6Z) | 2594(10) | 8209(4) | −2782(7) | 60(2) |

*Equivalent isotropic U is defined as one third of the trace of the orthogonalized $U_{ij}$ tensor.

EXAMPLE 49

Osmotic Tablets of Sertraline L-Lactate. This example illustrates a method for making osmotic tablets comprising a tablet core containing sertraline L-lactate surrounded by a semipermeable asymmetric membrane coating. Tablet cores were made using equipment standard in the pharmaceutical industry. Tablet core components comprising sertraline L-lactate (13.8 wt %), L-aspartic acid (11 wt %), calcium acetate (5 wt %), microcrystalline cellulose (29.5 wt %), and fructose (38.2 wt %) were blended, then run through a roller compactor and milled. This milled material was then blended wish 2.5 wt % magnesium stearate to form the final blended material that was used to make tablets having a total weight of 470 mg on a conventional tablet press (Kilian T-100). Semipermeable asymmetric membrane coatings (as described in U.S. Pat. No. 5,612,059, the teachings of which are incorporated herein by reference) were applied to the tablets using a side-vented pan coater (LDCS-20, Vector Corp., 675 44th St, Marion, Iowa 52302). The coating solution, comprising 10 wt % cellulose acetate 398-10, 2.5 wt % polyethylene glycol 3350, 15 wt % water, and 72.5 wt % acetone, was spray-coated onto the tablets at a rate of 20 g/minute until a 10 wt % coating level on the tablets had been achieved.

EXAMPLE 50

Osmotic Tablets of Sertraline L-Lactate. This example illustrates a method for making osmotic tablets comprising a tablet core containing sertraline L-lactate surrounded by a semipermeable asymmetric membrane coating. Tablet cores were made using equipment standard in the pharmaceutical industry. The tablet cores were prepared as follows: Glycerol monolaurate (5 wt %) was wet granulated with microcrystalline cellulose (14 wt %) using ethanol (95%) as the wet granulation solvent. After drying and milling, the wet granulate was blended with sertraline L-lactate (13.8 wt %), L-aspartic acid (11 wt %), calcium acetate (5 wt %), microcrystalline cellulose (an additional 13 wt %), and fructose (35.7 wt %). After all of the components were added, the granulate was run through a roller compactor and milled. The milled material was blended with magnesium stearate (2.5 wt %) to form the final blended material that was used to make tablets having a total weight of 470 mg on a conventional tablet press (Killan T-100, Kilian & Co., 415 Sargon Way Unit 1, Horsham, Pa. 19044). Semipermeable asymmetric membrane coatings (as described in U.S. Pat. No. 5,612,059) were applied to the tables using a side-vented pan coater LDCS-20, Vector Corp.). The coating solution, comprising 10 wt % cellulose acetate 395-10, 2.5 wt % polyethylene glycol 3350, 15 wt % water, and 72.5 wt % acetone, was spray-coated onto the tablets at a rate of 20 g/minute. One batch of tablets was made with a 10 wt % coating and a second batch of tablets was made having a 20 wt % coating.

EXAMPLE 51

Encapsulated Solution Dosage Form of Sertraline L-Lactate. Solutions of sertraline L-lactate are prepared in Capmul MCM™ (mono- and di-glycerides of caprylic and capric acids, Abitec Corporation, Columbus, Ohio 43219) at a concentration of 75 mgA/mL. The solutions are encapsulated in soft gelatin at a fill volume of 0.67 mL, yielding a unit dose of 50 mgA.

EXAMPLE 52

Sertraline L-aspartate. Sertraline free base (the compound of Preparation AA, 200.3 mg) was dissolved in ethyl acetate (800 µL, which had previous been saturated with water). L-aspartic acid (95.53 mg) was suspended in ethyl acetate (3 mL, which had previously been saturated with water). The aspartic acid suspension was added to the sertraline free base solution. The reaction mixture was stirred for 24 hours. The solids were filtered, washed with ethyl acetate saturated with water and then dried at 40° C. in a vacuum oven for 48 hours. The yield of sertraline L-aspartate was 96.4%. mp 247° C.

Preparation AA

Sertraline free base. Sertraline hydrochloride (5 grams) was dissolved in water (one liter). To this solution the required amount of 1N NaOH was added until the pH of the solution was adjusted to 8.0. The resulting solids were filtered and washed with deionized water (50 mL per gram of solid). The solids were dried at 40° C. in a vacuum oven for 48 hours. The yield was 98%. mp 67° C.

Preparation BB

Sertraline free base. Sertraline hydrochloride (300 g) was slurried in a 3.1 mixture of water (3 liters) and ethyl acetate (1 liter). The pH of the slurry was adjusted to 8.0 by the addition of approximately 1 liter of 1N sodium hydroxide solution. The free base of sertraline partitioned into the ethyl acetate phase. The two phases were allowed to separate completely by allowing the biphasic solution to stand overnight without agitation. The ethyl acetate layer was then separated and washed twice with 3 liters of deionized water to remove chloride ions. The final ethyl acetate layer containing sertraline base was concentrated to 300 mL under vacuum to remove residual water.

What is claimed is:

1. A sustained-release dosage form suitable for oral administration to a mammal, comprising sertraline, or a pharmaceutically acceptable salt thereof, and a pharmaceutically acceptable carrier, which dosage form releases sertraline into a use environment at a rate not exceeding 0.8 mgA/hr/kg, provided said dosage form (1) releases not more than 70% of the sertraline contained therein within the first hour following entry into said use environment and (2) releases sertraline at a rate of at least 0.02 mgA/hr/kg.

2. A dosage form as defined in claim 1, wherein said sertraline is present as sertraline free base, sertraline hydrochloride, sertraline aspartate, sertraline acetate or sertraline lactate.

3. A dosage form as defined in claim 1, wherein said mammal is a human.

4. A dosage form as defined in claim 1, in the form of a matrix tablet which remains substantially intact during the period of sustained release.

5. A dosage form as defined in claim 1, in the form of a disintegrating martix tablet.

6. A dosage form as defined in claim 1, in the form of a matrix tablet partially coated with a polymer which impedes the release of sertraline.

7. A dosage form as defined in claim 1, in the form of an osmotic tablet.

8. A dosage form as defined in claim 1, in the form of a membrane-coated hydrogel tablet.

9. A dosage form as defined in claim 1, which is multi-particulate.

10. A dosage form as defined in claim 1, in the from of a membrane-coated diffusion-based, capsule, tablet or multi-particulate.

11. A sustained-release dosage form suitable for administration to a mammal, comprising sertraline, or a pharmaceutically acceptable salt thereof, and a pharmaceutically acceptable carrier, which dosage form releases sertraline into a use environment at a rate not exceeding 40 mgA/hr, provided said dosage form (1) releases not more than 70% of the sertraline contained therein within the first hour following entry into said use environment and (2) releases sertraline at a rate of at least 1 mgA/hr.

12. A dosage form as defined in claim 11 wherein said sertraline is present as sertraline free base, sertraline hydrochloride, sertraline aspartate, sertraline acetate or sertraline lactate.

13. A dosage form as defined in claim 11, wherein said mammal is a human.

14. A dosage form as defined in claim 11, in the form of a matrix tablet which remains substantially intact during the period of sustained release.

15. A dosage form as defined in claim 11, in the form of a disintegrating matrix tablet.

16. A dosage form as defined in claim 11, in the form of a matrix tablet partially coated with a polymer which impedes the release of sertraline.

17. A dosage form as defined in claim 11, in the form of an osmotic tablet.

18. A dosage form as defined in claim 11, in the form of a membrane-coated hydrogel tablet.

19. A dosage form as defined in claim 11, which multiparticulate.

20. A dosage form as defined in claim 11, in the form of a membrane-coated fiffusion-based tablet or multiparticulate.

21. A sustained release dosage form suitable for oral administration to a mammal, comprising sertraline or a pharmaceutically acceptable salt thereof and a pharmaceutically acceptable carrier, which dosage form releases sertraline at a rate less than 40 mgA/hr in vitro when dissolution tested in a USP-2 apparatus containing 900 ml of acetate buffer, pH 4.0, which is 0.075 M in NaCl as follows:
(1) if said dosage form is a sustained release tablet or a non-disintegrating sustained release capsule, said USP-2 apparatus is equipped with a paddle stirring at 50 rpm;
(2) if said dosage form is a multiparticulate, said USP-2 apparatus is equipped with a paddle stirring at 100 rpm; provided said dosage form (a) releases not more than 70% of the sertraline contained therein within the first hour following initiation of testing and (b) releases sertraline at a rate of at least 1 mgA/hr.

22. A dosage form as defined in claim 21, wherein said sertraline is present as sertraline free base, sertraline hydrochloride, sertraline aspartate, sertraline acetate or sertraline lactate.

23. A dosage form as defined in claim 21, wherein said mammal is a human.

24. A dosage form as defined in claim 21, in the form of a matrix tablet which remains substantially intact during the period of sustained release.

25. A dosage form as defined in claim 21, in the form of a disintegrating matrix tablet.

26. A dosage form as defined in claim 21, in the form of a matrix tablet partially coated with a polymer which impedes the release of sertraline.

27. A dosage form as defined in claim 21, in the form of an osmotic tablet.

28. A dosage form as defined in claim 21, in the form of a membrane-coated hydrogel tablet.

29. A dosage form as defined in claim 21, which is multiparticulate.

30. A dosage form as defined in claim 21, in the form of a membrane-coated diffusion-based tablet or multiparticulate.

31. A temporally delayed plus sustained release dosage form suitable for oral administration to a mammal, comprising sertraline or a pharmaceutically acceptable salt thereof and a pharmaceutically acceptable carrier,
which dosage form, following ingestion by said mammal, releases sertraline into said mammal's GI tract at a rate less than 1 mgA/hr for an initial delay period of up to 3 hours,
and which thereafter release sertraline at a rate of from 1 mgA/hr to 40 mgA/hr, provided said dosage form releases not more tan 70% of the sertraline contained therein within the first hour after said delay period.

32. A dosage form as defined in claim 31, wherein said delay period is up to two hours.

33. A dosage form as defined in claim 31, wherein the rate of release following said delay period is from 1 mgA/hr to 30 mgA/hr.

34. A dosage form as defined in claim 31, wherein said sertraline is present as sertraline free base, sertraline hydrochloride, sertraline aspartate, sertraline acetate or sertraline lactate.

35. A dosage form as defined in claim 31, wherein said mammal is a human.

36. A temporally delayed plus sustained release dosage form suitable for administration to a mammal, said dosage form having an initial temporal delay period of up to 3 hours, comprising sertraline or a pharmaceutically acceptable salt thereof and a pharmaceutically acceptable carrier, which dosage form, when dissolution tested in vitro in a USP-2 apparatus containing 900 ml of acetate buffer, pH 4.0, which is 0.075 M in NaCl,
releases sertraline at a rate less than 1 mgA/hr for a period corresponding to said delay period and, thereafter,
releases sertraline at a rate of from 1 mgA/hr to 40 mgA/hr, provided the dosage form releases not more than 70% of the remaining sertraline contained therein within the first hour following said delay.

37. A dosage form as defined in claim 36, wherein said delay period is up to two hours.

38. A dosage form as defined in claim 36, wherein the rate of release following said delay period is from 1 mgA/hr to 30 mgA/hr.

39. A dosage form as defined in claim 36, wherein said sertraline is present as sertraline free base, sertraline hydrochloride, sertraline aspartate, sertraline acetate or sertraline lactate.

40. A dosage form as defined in claim 36, wherein said mammal is a human.

41. A dosage form as defined in claim 36, in he form of a tablet.

42. A dosage form as defined in claim 36, which is multiparticulate.

43. A spatially delayed plus sustained release dosage form suitable for oral administration to a mammal, comprising sertraline or a pharmaceutically acceptable salt thereof and a pharmaceutically acceptable carrier,
which dosage form, following ingestion by said mammal, releases sertraline into said mammal's stomach at a rate less than 1 mgA/hr,
and which, after having passed into said mammal's small intestine, effects sustained release at a rate of from 1 mgA/hr to 40 mgA/hr,
provided said dosage form releases not more than 70% of the sertraline contained therein with the first hour after passing into said mammal's small intestine.

44. A dosage form as defined in claim 43, wherein the onset of sustained release is pH-triggered.

45. A dosage form as defined in claim 44, comprising a sustained release dosage form coated with a polymer that prevents release of sertraline at the pH of the stomach, but which is permeable to sertraline at the pH of the small intestine.

46. A dosage form as defined in claim 44, wherein said sustained release dosage form is multiparticulate.

47. A dosage form as defined in claim 44 wherein said sustained release dosage form is a tablet.

48. A dosage form as defined in claim 43, which is enzyme-triggered.

49. A dosage form as defined in claim 48, comprising a sustained release dosage form coated with a membrane having a hydrophobic liquid entrained within the pores thereof, said hydrophobic liquid being substantially impermeable to water and sertraline, but capable of changing, through enzymatic degradation, so that said membrane becomes substantially permeable to water and sertraline when said dosage form moves into the environment of the small intestinal lumen.

50. A dosage form as defined in claim 48, wherein said sustained release dosage form is mutliparticulate.

51. A dosage form as defined in claim 48, wherein said sustained release dosage form is a matrix.

52. A dosage form as defined in claim 43, wherein said sertraline is present as sertraline free base, sertraline hydrochloride, sertraline aspartate, sertraline acetate or sertraline lactate.

53. A dosage form as defined in claim 43, wherein said mammal is a human.

54. A sustained release pH-triggered dosage form suitable for oral administration to a mammal, said dosage form having an initial delay period prior to the onset of sustained release, comprising sertraline or a pharmaceutically acceptable salt thereof and a pharmaceutically acceptable carrier, which dosage form, when tested in vitro in a USP-2 apparatus,
    releases sertraline into 0.1 N HCl at a rate less than 1 mgA/hr for 1 hour and, thereafter,
    releases sertraline into phosphate buffer, pH 6.8 containing 1% polysorbate 80 at a me of from 1 mgA/hr to 40 mgA/hr, provided the dosage form releases not more than 70% of the remaining sertraline contained therein within the first hour following said delay.

55. A dosage form as defined in claim 54, comprising a sustained release dosage form coated with a coating comprising a polymer that prevents release of sertraline in said HCl at a rate exceeding 1 mgA/hr, but which is permeable to and allows sustained release of sertraline in said phosphate buffer.

56. A dosage form as defined in claim 55, wherein said sustained release dosage form is multiparticulate.

57. A dosage form as defined in claim 55, wherein said sustained release dosage form is a tablet.

58. A dosage form as defined in claim 54, wherein said sertraline is present as sertraline free base, sertraline hydrochloride, sertraline aspartate, sertraline acetate or sertraline lactate.

59. A dosage form as defined in claim 54, wherein said mammal is a human.

60. A sustained release enzyme-triggered dosage form suitable for oral administration to a mammal, said dosage form having an initial delay period prior to the onset of sustained release, comprising sertraline or a pharmaceutically acceptable salt thereof and a pharmaceutically acceptable carrier, which dosage form, when tested in vitro in a USP apparatus
    releases sertraline into 0.1 N HCl at a rate less than 1 mgA/hr for a period of 1 hour and, thereafter,
    releases sertraline at a rate of from 1 mgA/hr to 40 mgA/hr into phosphate buffer, pH 6.8, containing 1% polysorbate 80 and in the presence of an enzyme suitable for triggering the onset of said sustained release, provided the dosage form releases not more than 70% of the remaining sertraline contained therein within the first hour following said delay.

61. A dosage form as defined in claim 60, comprising a sustained release dosage form coated with a membrane having a hydrophobic liquid entrained within the pores thereof, said hydrophobic liquid being substantially impermeable to water and sertraline in said acid, but capable of changing in said buffer, though enzymatic degradation in the presence of said enzyme, so that said membrane becomes substantially permeable to water and sertraline.

62. A dosage form as defined in claim 60, wherein said sustained release dosage form is multiparticulate.

63. A dosage form as defined in claim 60, wherein said sustained release dosage form is a tablet.

64. A dosage form as defined in claim 60, wherein said sertraline is present as sertraline free base, sertraline hydrochloride, sertraline aspartate, sertraline acetate or sertraline lactate.

65. A dosage form as defined in claim 60, wherein said mammal is a human.

66. A sustained release dosage form suitable for oral administration to a mammal, comprising sertraline, or a pharmaceutically acceptable salt thereof, and a pharmaceutically acceptable carrier, which dosage form, when orally dosed to said mammal, results in a maximum sertraline plasma concentration, $C_{max}$, which is less than 80% of the $C_{max}$ determined ween an equal dose of sertraline is orally administered in the form of an immediate release bolus provided said sustained release dosage form (1) releases not more than 70% of the sertraline contained therein within the first hour following ingestion and (2) releases sertraline at a rate of at least 1 mgA/hr.

67. A dosage form as defined in claim 66, which provides a total blood drug exposure that is not proportionately decreased as much as $C_{max}$.

68. A dosage form as defined claim 66, wherein said sertraline is present as sertraline free base, sertraline hydrochloride, sertraline aspartate, sertraline acetate or sertraline lactate.

69. A dosage form as defined in claim 66, wherein said mammal is a human.

70. A dosage form as defined in claim 66, in the form of a tablet.

71. A dosage form as defined in claim 66, which is multiparticulate.

72. A dosage form as defined in claim 66, which is a delayed plus sustained release form exhibiting a delay period of up to three hours prior to the onset of sustained release, said dosage form releasing sertraline at a rate of not more than 1 mgA/hr during said delay period.

73. A dosage form as defined in claim 72, wherein said delay is temporal.

74. A dosage form as defined in claim 72, wherein said delay is spatial.

75. A method for treating a psychiatric illness, premature ejaculation, chemical dependency, premenstrual dysphoric disorder, or obesity, comprising administering to a mammal in need of such treatment, a therapeutically effective amount of sertraline in a sustained-release oral dosage form as defined in claim 1.

76. A method for treating a psychiatric illness, premature ejaculation, chemical dependency, premenstrual dysphoric disorder, or obesity, comprising administering to a mammal in need of such treatment, a therapeutically effective amount of sertraline in a sustained-release oral dosage form as defined in claim 1.

77. A method for treating a psychiatric illness, premature ejaculation, chemical dependency, premenstrual dysphoric disorder, or obesity, comprising administering to a mammal in need of such treatment, a therapeutically effective amount of sertraline in a sustained-release oral dosage form as defined in claim 21.

78. A method for treating a psychiatric illness, premature ejaculation, chemical dependency, premenstrual dysphoric disorder, or obesity, comprising administering to a mammal in need d such treatment, a therapeutically effective amount of sertraline in a delayed plus sustained-release oral dosage form as defined in claim 31.

79. A method for treating a psychiatric illness, premature ejaculation, chemical dependency, premenstrual dysphoric disorder, or obesity, comprising administering to a mammal in need of such treatment, a therapeutically effective amount of sertraline in a delayed plus sustained-release oral dosage form as defined in claim 36.

80. A method for treating a psychiatric illness, premature ejaculation, chemical dependency, premenstrual dysphoric disorder, or obesity, comprising administering to a mammal in need of such treatment, a therapeutically effective amount of sertraline in a delayed plus sustained-release oral dosage form as defined in claim 43.

81. A method for treating a psychiatric illness, premature ejaculation, chemical dependency, premenstrual dysphoric disorder, or obesity, comprising administering to a mammal in need of such treatment, a therapeutically effective amount of sertraline in a delayed plus sustained-release oral dosage form as defined in claim 54.

82. A method for treating a psychiatric illness, premature ejaculation, chemical dependency, premenstrual dysphoric disorder, or obesity, comprising administering to a mammal in need of such treatment, a therapeutically effective amount of sertraline in a delayed plus sustained-release oral dosage form as defined in claim 60.

83. A method for treating a psychiatic illness, premature ejaculation, chemical dependency, premenstrual dysphoric disorder, or obesity, comprising administering to a mammal in need of such treatment, a therapeutically effective amount of sertraline in a delayed plus sustained-release oral dosage form as defined in claim 66.

84. Sertraline acetate.

85. Sertraline acetate of claim 84 having the X-ray crystal structure of FIG. 1.

86. Sertraline acetate·¼ hydrate.

87. A pharmaceutical composition comprising sertraline acetate of claim 84 and a pharmaceutically acceptable carrier or diluent.

88. A pharmaceutical composition comprising sertraline acetate of claim 85 and a pharmaceutically acceptable carrier or diluent.

89. A pharmaceutical composition comprising sertraline acetate·¼ hydrate of claim 86 and a pharmaceutically acceptable carrier or diluent.

90. Sertraline L-lactate.

91. Sertraline L-lactate of claim 90 having the X-ray crystal structure of FIG. 3.

92. A pharmaceutical composition comprising sertraline L-lactate of claim 90 and a pharmaceutically acceptable carrier or diluent.

93. A pharmaceutical composition comprising sertraline L-lactate of claim 91 and a pharmaceutically acceptable carrier or diluent.

94. Sertraline L-aspartate.

95. A pharmaceutical composition comprising sertraline of claim 11, wherein said sertraline is sertraline L-aspartate and a pharmaceutically acceptable carrier or diluent.

96. A method for treating a disease or condition selected from anorexia, impulse disorders, onychophagia, premenstrual syndrome, psychotic disorders schizophrenia inflammatory disorders, hyperactive immune system disorders, and chemical dependency in a subject suffering from one or more of said diseases or conditions comprising administering to said subject an effective amount of sertraline acetate, sertraline L-lactate or sertraline L-aspartate.

97. A method of claim 96 wherein sertraline acetate is administered.

98. A method of claim 96 wherein sertraline L-lactate is administered.

99. A method for treating mental depression in a mentally-depressed subject comprising administering to said subject an effective amount of sertraline acetate, sertraline L-lactate or sertraline L-aspartate.

100. A method of claim 99 wherein sertraline acetate is administered.

101. A method of claim 99 wherein sertraline L-lactate is administered.

102. A method for treating an anxiety-related disorder in a subject suffering therefrom comprising administering to said subject an effective amount of sertraline acetate, sertraline L-lactate or sertraline L-aspartate.

103. A method of claim 102 wherein said anxiety-related disorder is obsessive-compulsive disorder.

104. A method of claim 103 wherein sertraline acetate is administered.

105. A method of claim 103 wherein sertraline L-lactate is administered.

106. A process for preparing sertraline acetate comprising reacting a salt of sertraline with a base in the presence of a suitable organic solvent to form sertraline free base, partitioning said sertraline free base into an organic solvent and reacting said sertraline free base with acetic acid in the presence of a suitable organic solvent.

107. A process of claim 106 wherein said salt of sertraline is sertraline hydrochloride and said solvent is hexane.

108. A process for preparing sertraline acetate comprising reacting sertraline free base with acetic acid in the presence of a suitable organic solvent.

109. A process for preparing sertraline L-lactate comprising reacting a salt of sertraline with a base in the presence of a suitable organic solvent to form sertraline free base, partitioning said sertraline free base into an organic solvent and reacting said sertraline free base with L-lactic acid in the presence of a suitable organic solvent.

110. A process of claim 109 wherein said salt of sertraline is sertraline hydrochloride and said solvent is ethyl acetate.

111. A process of claim 109 wherein said salt of sertraline is sertraline mandelate and said solvent is ethyl acetate.

112. A process for sertraline L-lactate comprising reacting sertraline free base with L-lactic acid in the presence of a suitable organic solvent.

113. A process for preparing sertraline L-aspartate comprising reacting a salt of sertraline with a base in the presence of a suitable organic solvent to form sertraline free base, partitioning said sertraline free base into an organic solvent and reacting said sertraline free base with aspartic acid in the presence of a suitable organic solvent.

114. A process of claim 113 wherein said salt of sertraline is sertraline hydrochloride and said solvent is ethyl acetate saturated with water.

115. A process for preparing sertraline L-aspartate comprising reacting sertraline free base with L-aspartic acid in the presence of a suitable organic solvent.

116. The method according to any one of claims 75–83 wherein said mammal is a human patient.

\* \* \* \* \*